US 8,124,603 B2

(12) United States Patent
Hanna et al.

(10) Patent No.: US 8,124,603 B2
(45) Date of Patent: Feb. 28, 2012

(54) IN VIVO STUDIES OF CRYSTALLINE FORMS OF MELOXICAM

(75) Inventors: Mazen Hanna, Bradford (GB); Ning Shan, Tampa, FL (US); Miranda L. Cheney, Tampa, FL (US); David R. Weyna, Tampa, FL (US)

(73) Assignee: Thar Pharmaceuticals, Pittsburgh, PA (US)

( * ) Notice: Subject to any disclaimer, the term of this patent is extended or adjusted under 35 U.S.C. 154(b) by 434 days.

(21) Appl. No.: 12/321,525

(22) Filed: Jan. 22, 2009

(65) Prior Publication Data
US 2009/0203680 A1 Aug. 13, 2009

Related U.S. Application Data

(60) Provisional application No. 61/011,902, filed on Jan. 22, 2008, provisional application No. 61/127,631, filed on May 14, 2008, provisional application No. 61/196,860, filed on Oct. 21, 2008.

(51) Int. Cl.
*C07D 279/02* (2006.01)
*C07D 417/12* (2006.01)
*A61K 31/5415* (2006.01)

(52) U.S. Cl. ...................... 514/226.5; 544/49

(58) Field of Classification Search .............. 544/49; 514/226.5
See application file for complete search history.

(56) References Cited

U.S. PATENT DOCUMENTS

| 4,233,299 | A  | * | 11/1980 | Trummlitz et al. | 514/226.5 |
| 6,869,948 | B1 | * | 3/2005 | Bock et al. | 514/226.5 |
| 6,967,248 | B2 |   | 11/2005 | Coppi et al. |   |
| 2004/0171611 | A1 |   | 9/2004 | Trummlitz et al. |   |
| 2006/0025408 | A1 |   | 2/2006 | Venkataraman et al. |   |

FOREIGN PATENT DOCUMENTS

| WO | WO 99/09988 | 3/1999 |
| WO | WO 2004/078163 | 9/2004 |
| WO | WO 2007/144323 | 12/2007 |

OTHER PUBLICATIONS

Hyo-Kyung Han and Hoo-Kyun Choi, "Improved absorption of meloxicam via salt formation with ethanolamines," 65 European J. Pharmaceutics and Biopharmaceutics 99 (2007).

* cited by examiner

*Primary Examiner* — Kahsay T Habte
(74) *Attorney, Agent, or Firm* — Dawn Gardner Krosnick; Rakoczy Molino; Mazzochi Siwik LLP

(57) ABSTRACT

The invention is directed to novel crystalline forms of meloxicam. These novel crystalline forms of meloxicam have improved bioavailability, an enhanced rate of dissolution and shorter time to $C_{max}$ in blood, as compared to pure meloxicam.

25 Claims, 70 Drawing Sheets

IN VIVO STUDIES OF CRYSTALLINE FORMS OF MELOXICAM

CROSS-REFERENCE TO RELATED APPLICATIONS

Figure 1:
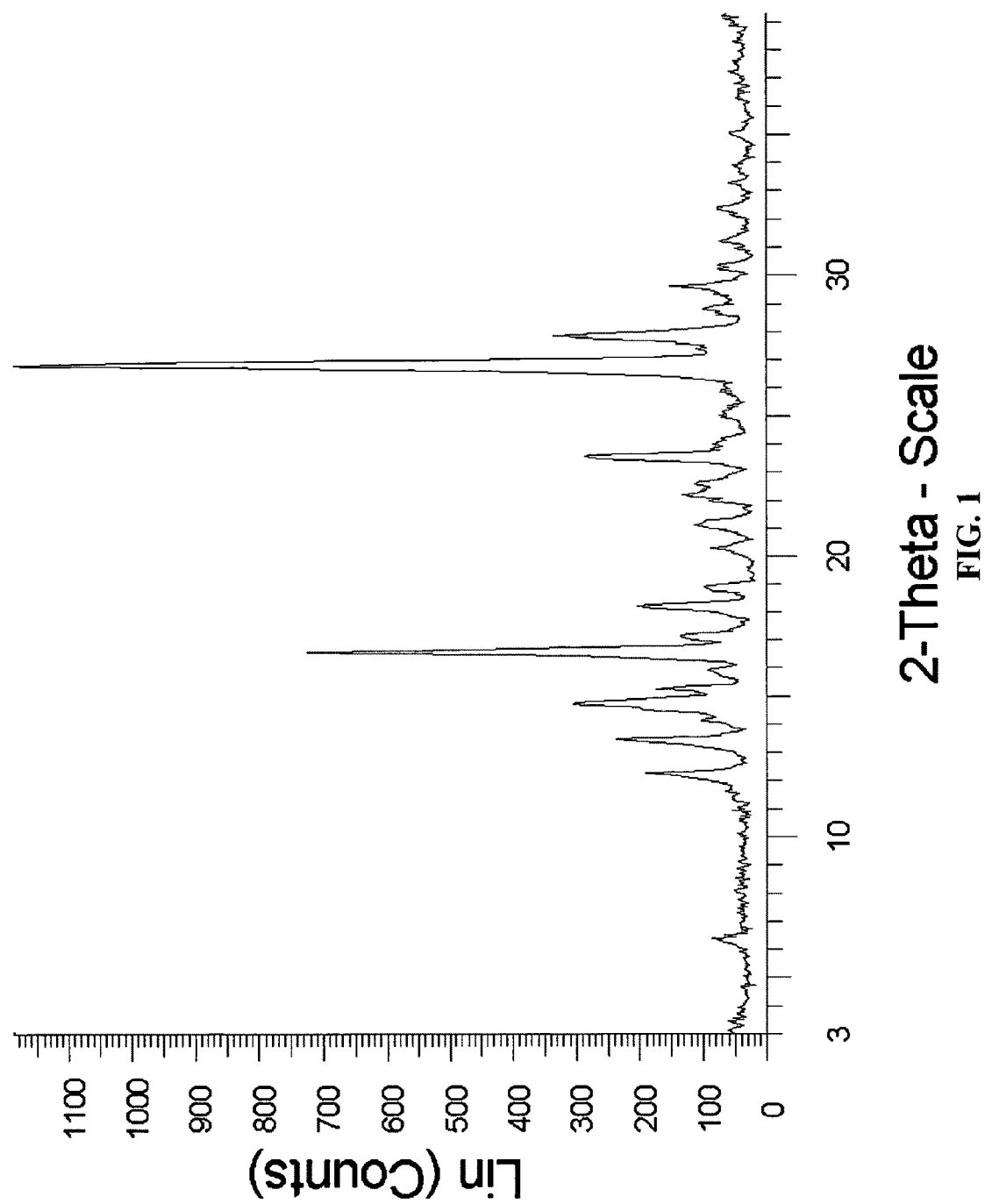

The application claims the benefit under 35 U.S.C. §1.119 (e) of U.S. provisional application No. 61/011,902, filed on Jan. 22, 2008; of U.S. provisional application No. 60/127, 631, filed May 14, 2008; and of U.S. provisional application No. 61/196,860, filed Oct. 21, 2008, each of which are incorporated herein by reference in its entirety.

FIELD OF THE INVENTION

The disclosure pertains to new forms of meloxicam, which include meloxicam cocrystals, salts, hydrous forms, solvates, hydrates and solvates of salts, mixtures thereof, as well as methods for their preparation and pharmaceutical compositions that include one or more of these new forms. In addition, results of 24 hour in-vivo study in a rat model where pharmacokinetic profiles of such cocrystals of meloxicam are disclosed.

BACKGROUND OF THE INVENTION

Meloxicam is known as (8E)-8-[hydroxy-[(5-methyl-1,3-thiazol-2-yl)amino]methylidene]-9-methyl-10,10-dioxo-10$\lambda^6$-thia-9-azabicyclo[4.4.0]deca-1,3,5-trien-7-one, it can also be expressed as (4-hydroxy-2-methyl-N-(5-methyl-2-thiazolyl)-2H-1,2-benzothiazine-3-carboxamide-1,1-dioxide). Meloxicam is depicted by the following chemical structure:

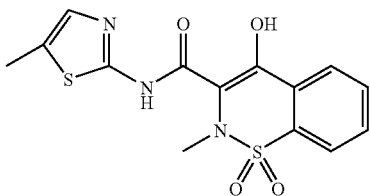

Meloxicam is a non steroidal, anti-inflammatory (NSAID) and anti-pyretic drug used to relieve symptoms of arthritis, fever, and can be used as an analgesic for conditions of inflammatory component. It has been developed originally by Boehringer Ingelheim and marketed in Europe as Melox/Movalis or Recoxa brand names for the treatment of rheumatoid arthritis, short term use in osteoarthritis and ankylosing spondylitis. In the United States its marketed as Mobic® for the treatment of osteoarthritis. Meloxicam is manufactured either as a tablet (7.5 and 15 mg dose) or as an oral suspension (7.5 mg/5 ml dose). The form of meloxicam used in the marketed product, Mobic® is the pure form of meloxicam.

Meloxicam has also been used to treat animal target species (dogs, cats, horses, cattle, and pigs) and is marketed worldwide in three forms; injectable solution, oral suspension, and chewable tablets. In the US, meloxicam is licensed for use in dogs as injectable and oral forms, but is only licensed as injectable solution for cats. The Food and Drug Administration (FDA) has specifically approved the use of meloxicam in dogs to reduce the inflammation and pain of joint diseases and muscle injuries.

Meloxicam is a pastel yellow solid, practically insoluble in water, with higher solubility observed in strong acids and bases. It is very slightly soluble in methanol. Meloxicam has an apparent partition coefficient (log P)$_{app}$=0.1 in n-octanol/buffer pH 7.4. Meloxicam has pKa values of 1.1 and 4.2.

Enhancement of meloxicam's low aqueous solubility has been the subject of many publications, by using different solvents (see Seedhar et al, AAPS Pharma Sci. Tech. 2003; 4(3) or salt formation (Choi et al, EU J. Pharm and Biopharm. 65 (2007) 99-103) or complexing with metals (Cini et al, J. Chem. Soc. Dalton Trans, 2002, 1888-1897) Preparation of different crystalline ploymorphic forms of meloxicam are disclosed in the literature, see for example U.S. Pat. No. 6,967,248 and application 2006/0025408 A1. In addition, dissolution improvements of meloxicam are also disclosed in U.S. Pat. No. 6,869,948 and WO 99/09988.

Generally, these approaches have involved different polymorphic and salt forms as well as some solid state formulations which sometimes involve generation of certain salt forms, or complexing with metal ions. Such approaches might not be desirable for particular uses, such as parenteral, owing to their inherent lack of stability, acidity and possible toxicity.

Because of the limitations related to the low aqueous solubility of pure meloxicam, there is a need to develop novel forms of meloxicam that have improved physico-chemical properties including aqueous solubility, which can be formulated for use in various delivery routes, including parenteral and oral administration.

Another limitation for the pain relief drug, meloxicam is that it takes a long time to achieve the desired plasma concentration and start reliving pain. The mean peak plasma concentration $C_{max}$ for meloxicam is achieved within four to five hours under fasted conditions, indicating prolonged drug absorption which might be influenced by the rate of dissolution. Therefore enhancing the rate of dissolution could lead to shortening $C_{max}$ and a quicker onset of pain relief. This is a clear clinical benefit for patients.

These limitations have been tackled by generating novel crystalline forms of meloxicam that includes cocrystals, salts, and solvates (e.g. hydrates and mixed solvates as well as solvates of salts), and mixtures of thereof. The rate of dissolution has been improved and more rapid onset achieved in a rat model.

SUMMARY OF THE INVENTION

The present disclosure is directed towards generating new crystalline forms of meloxicam that have improved aqueous solubility, rate of dissolution and achieved faster onset. One aspect of the present disclosure includes novel molecular complexes of meloxicam that includes cocrystals, salts, and solvates (e.g. hydrates and mixed solvates as well as solvates of salts), and mixtures containing such materials. In addition, the disclosure further includes methods for the preparation of such complexes. The disclosure further includes compositions of molecular complexes of meloxicam suitable for pharmaceutical application. Specific molecular complexes pertaining to the disclosure include, but are not limited to, cocrystals of meloxicam with adipic, benzoic, fumaric, glutaric, 4-hydroxybenzoic acid, malic, maleic, succinic, saliycylic, acetylsalicylic, 1-hydroxy 2-naphthoic, malonic, glycolic, 2,5-dihydroxybenzoic, camphoric and hydrocinnamic acid as well as maltol and ethyl maltol, Obvious variants of the disclosed meloxicam forms in the text, including those described by the drawings and examples will be readily apparent to the person of ordinary skill in the art having the present disclosure, and such variants are considered to be a part of the current invention.

According to one aspect of the invention, a crystalline form of meloxicam is provided which when administered to a subject has improved bioavailability, an enhanced rate of dissolution and shorter time to $C_{max}$ in blood of meloxicam as compared to pure meloxicam. Pure meloxicam refers to the crystalline, non formulated form of meloxicam used in Mobic® as marketed by Boehringer Ingelheim and also supplied by fine chemical/bulk pharmaceutical manufacturers. Administration includes, but is not limited to, oral, parenteral, buccal, nasal and any other suitable route where the drug is intended for systemic delivery. It can also be administered locally (e.g. topical, ocular) to treat different symptoms that NSAIDs are prescribed for.

According to another aspect of the invention, crystalline forms of meloxicam selected from the group consisting of co-crystal meloxicam:fumaric acid, co-crystal meloxicam:succinic acid, co-crystal meloxicam:adipic acid; co-crystal meloxicam:benzoic acid, co-crystal meloxicam:DL-malic acid, co-crystal meloxicam:L-malic acid, co-crystal meloxicam:glutaric acid, co-crystal meloxicam:acetylsalicylic acid, co-crystal meloxicam:salicylic acid form I, co-crystal meloxicam:salicylic acid form II, co-crystal meloxicam:salicylic acid form III, co-crystal meloxicam: 1-hydroxy-2-naphthoic acid, co-crystal meloxicam:maleic acid, co-crystal meloxicam:4-hydroxybenzoic acid, co-crystal meloxicam: malonic acid, co-crystal meloxicam:glycolic acid, co-crystal meloxicam:2,5-dihydroxybenzoic acid form I, co-crystal meloxicam:2,5-dihydroxybenzoic acid form II, co-crystal meloxicam:camphoric acid form I, co-crystal meloxicam:camphoric acid form II, co-crystal meloxicarn:maltol, co-crystal meloxicam:ethyl maltol, and co-crystal meloxicam:hydrocinnamic acid, are provided.

According to yet another aspect of the invention, there is provided a crystalline form of meloxicam wherein said crystalline form is co-crystal meloxicam:fumaric acid which: a) has a PXRD diffraction pattern with peaks at about 12.13, 14.75, 16.52, 18.14, 22.21, 23.53 and 26.86+/–0.2 degrees two-theta; and/or b) has a PXRD diffraction pattern substantially as depicted in FIG. 1.

Figure 3:
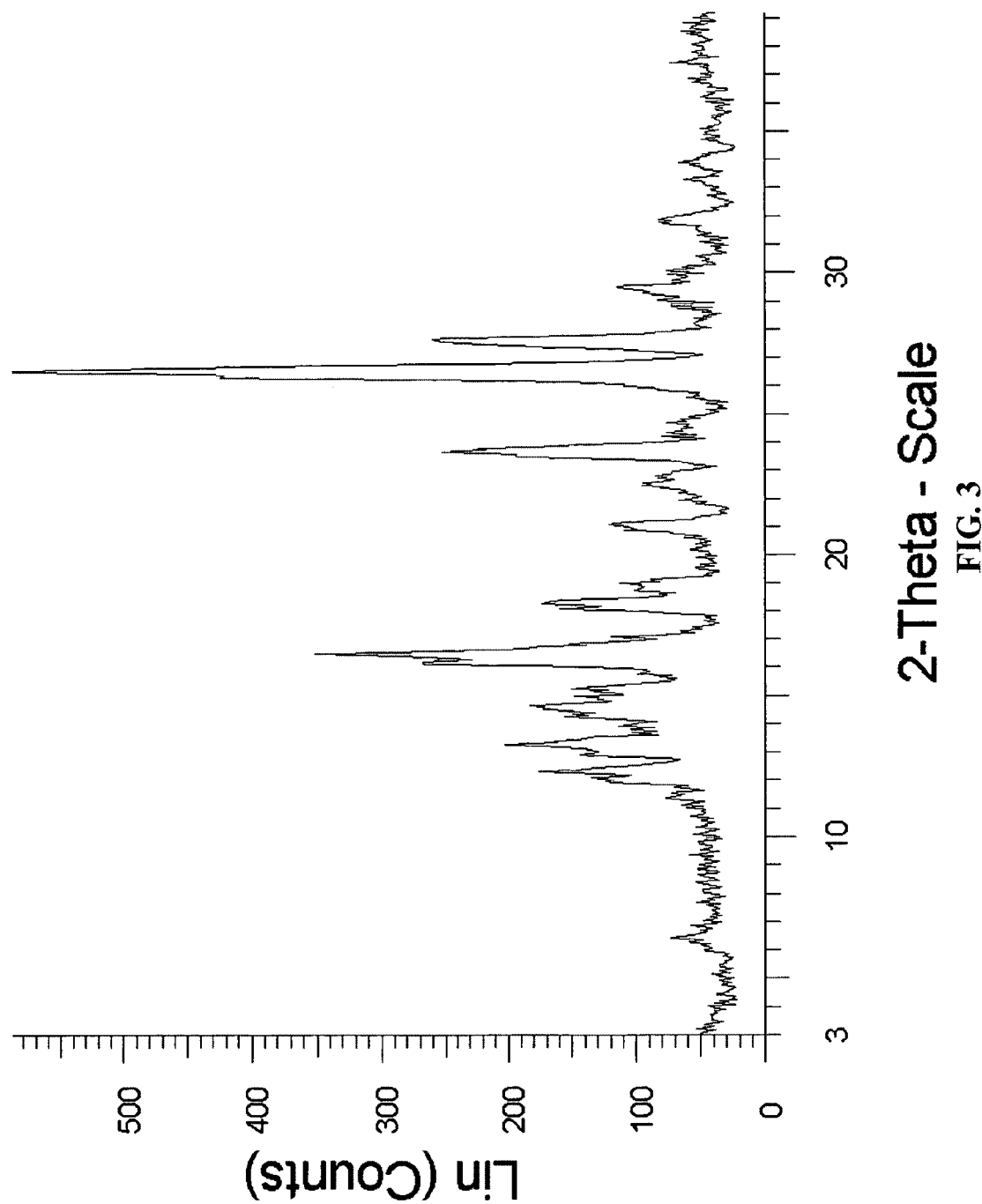

According to yet another aspect of the invention, there is provided a crystalline form of meloxicam wherein said crystalline form is co-crystal meloxicam:succinic acid which: a) has a PXRD diffraction pattern with peaks at about 13.22, 14.50, 16.41, 18.30, 23.68, 26.59 and 27.67+/–0.2 degrees two-theta; and/or b) has a PXRD diffraction pattern substantially as depicted in FIG. 3.

Figure 5:
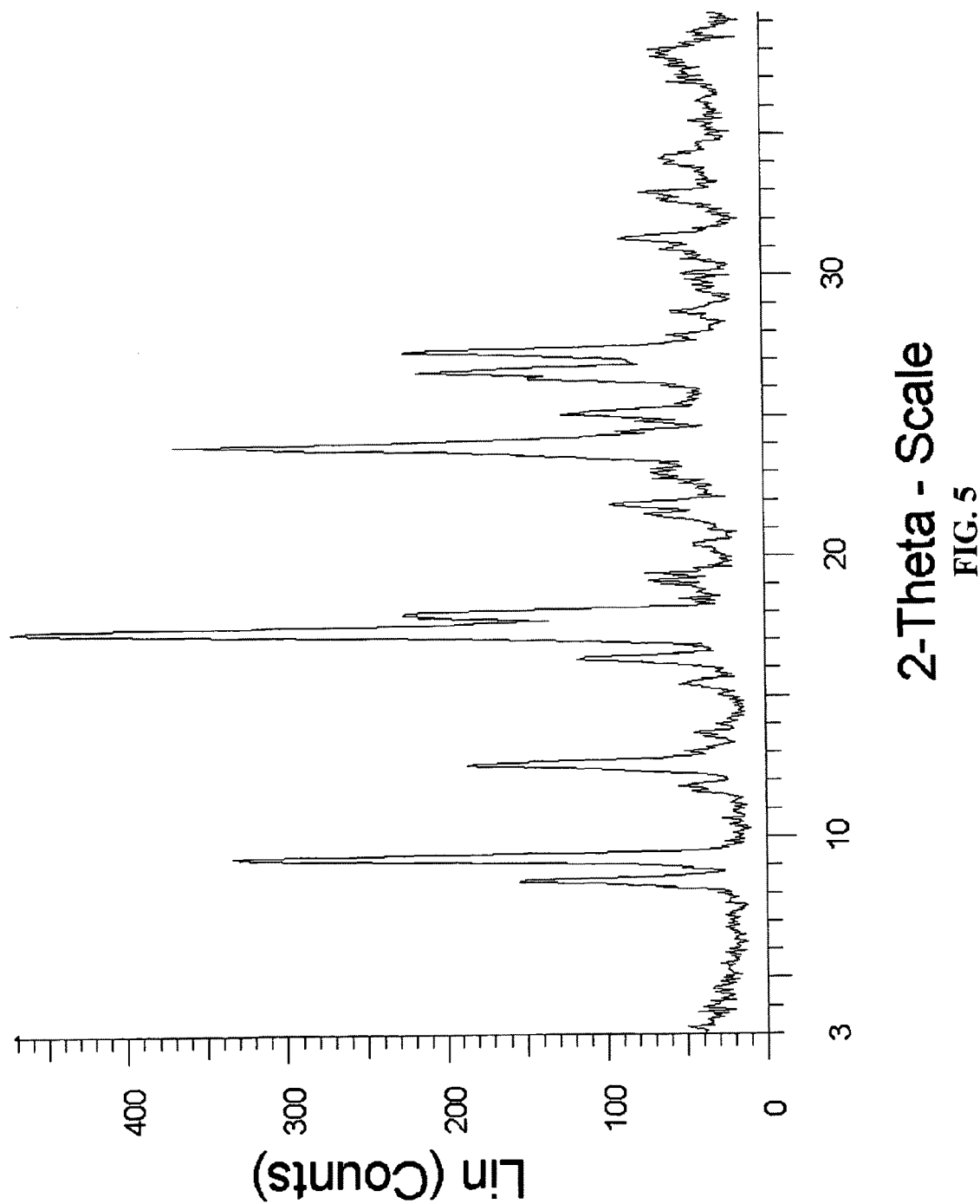

According to yet another aspect of the invention, there is provided a crystalline form of meloxicam wherein said crystalline form is co-crystal meloxicam:adipic acid which: a) has a PXRD diffraction pattern with peaks at about 8.56, 9.38, 12.67, 17.50, 24.13, 26.77, and 27.46+/–0.2 degrees two-theta; and/or b) has a PXRD diffraction pattern substantially as depicted in FIG. 5.

Figure 7:
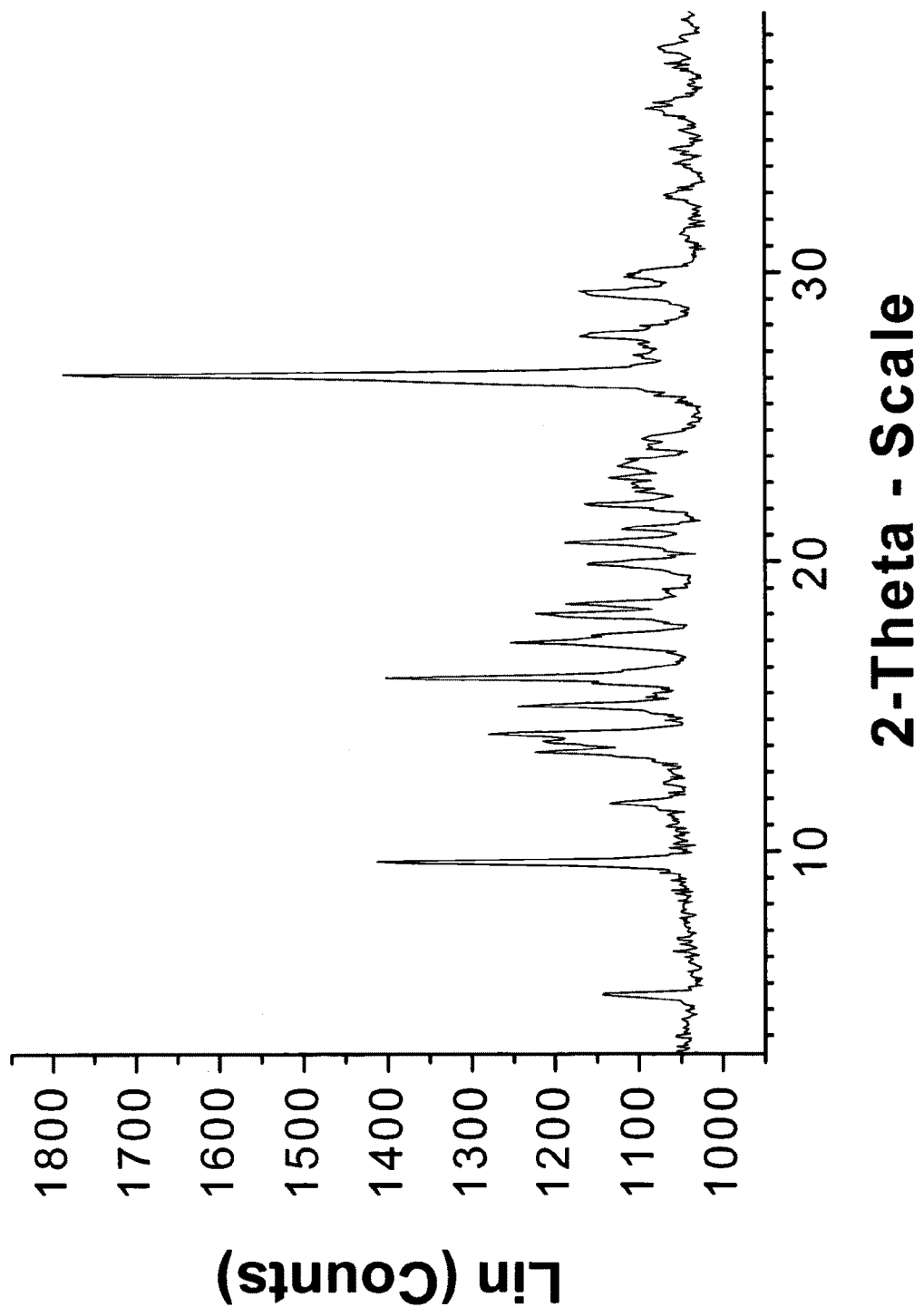

According to yet another aspect of the invention, there is provided a crystalline form of meloxicam wherein said crystalline form is co-crystal meloxicam:benzoic acid which: a) has a PXRD diffraction pattern with peaks at about 9.61, 14.06, 15.00, 16.01, 17.21, 18.20 and 26.47+/–0.2 degrees two-theta; and/or b) has a PXRD diffraction pattern substantially as depicted in FIG. 7.

Figure 9:
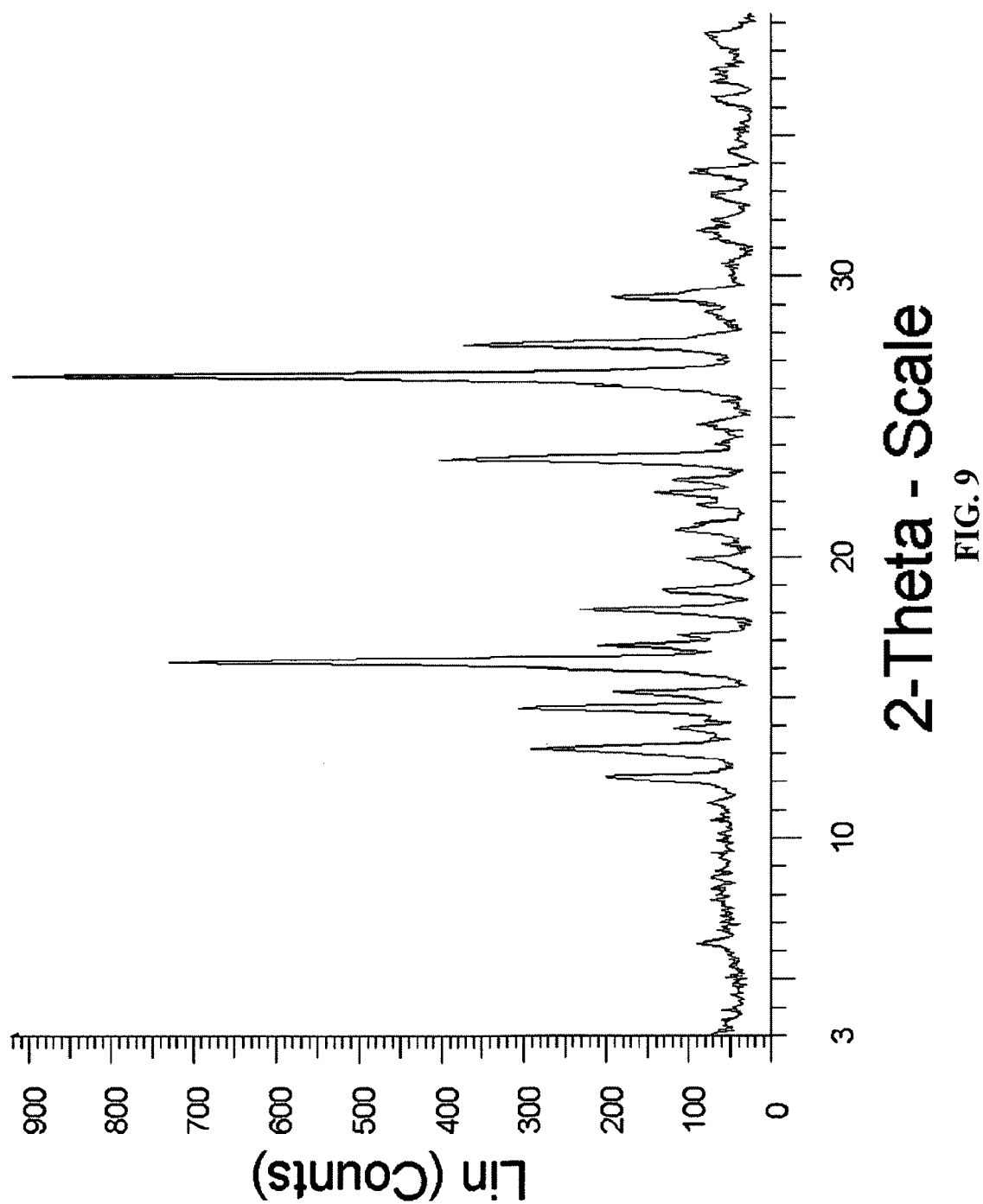

According to yet another aspect of the invention, there is provided a crystalline form of meloxicam wherein said crystalline form is co-crystal meloxicam:DL-malic acid which: a) has a PXRD diffraction pattern with peaks at about 13.39, 14.87, 16.55, 18.39, 23.78, 26.80 and 27.91+/–0.2 degrees two-theta; and/or b) has a PXRD diffraction pattern substantially as depicted in FIG. 9.

Figure 11:
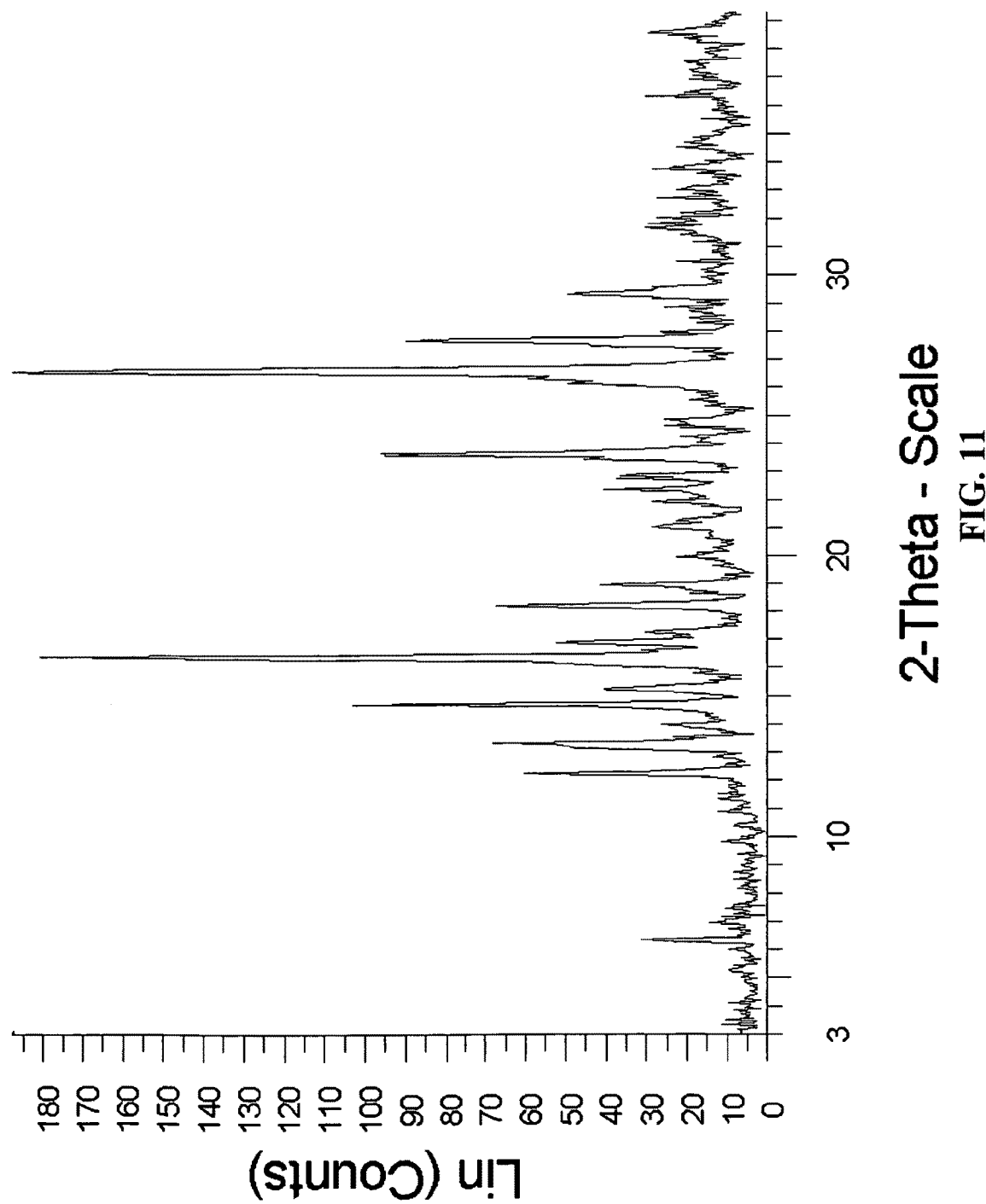

According to yet another aspect of the invention, there is provided a crystalline form of meloxicam wherein said crystalline form is co-crystal meloxicam:L-malic acid which: a) has a PXRD diffraction pattern with peaks at about 13.14, 14.57, 16.25, 23.51, 24.66, 26.53 and 27.66+/–0.2 degrees two-theta; and/or b) has a PXRD diffraction pattern substantially as depicted in FIG. 11.

Figure 13:
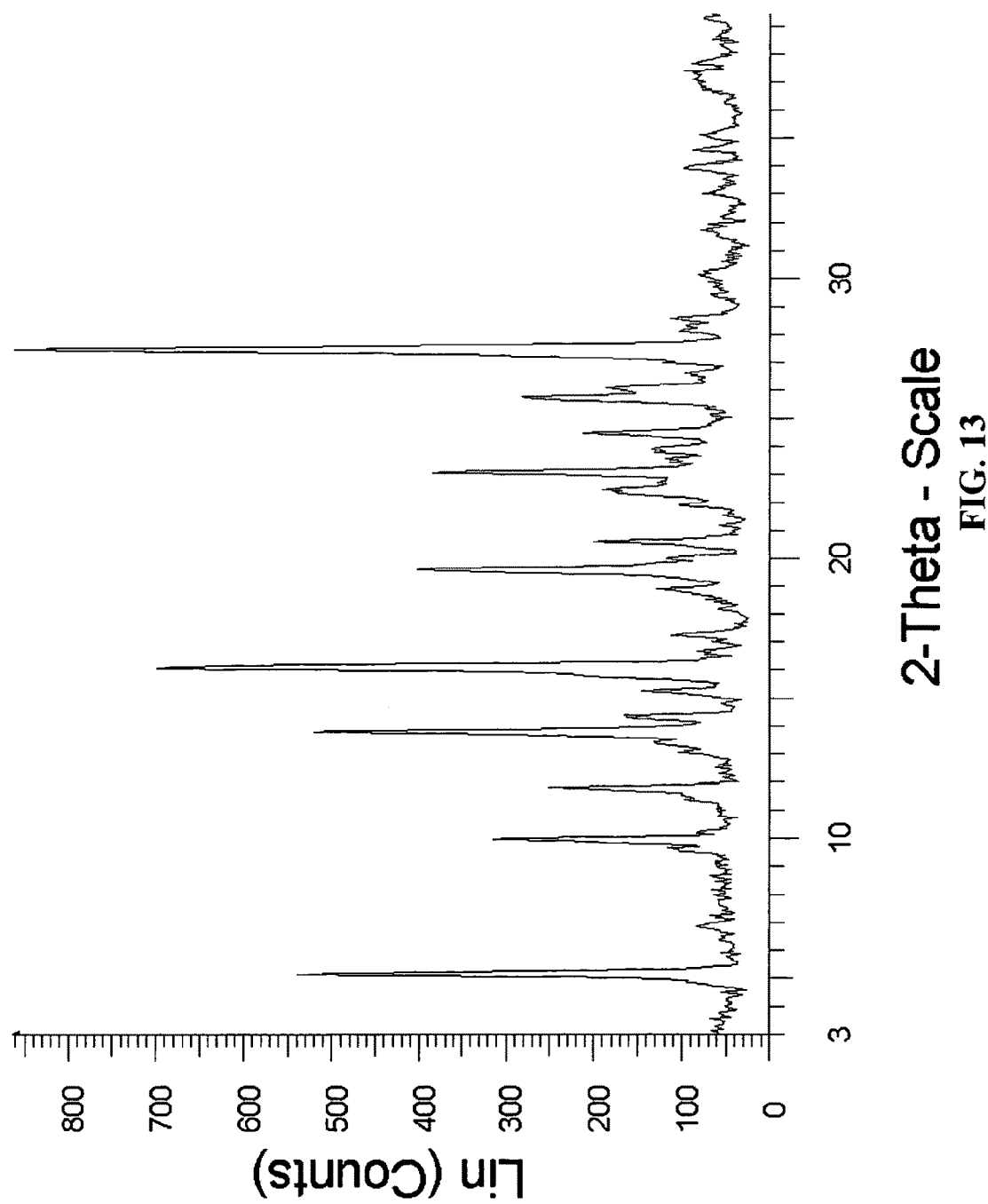

According to yet another aspect of the invention, there is provided a crystalline form of meloxicam wherein said crystalline form is co-crystal meloxicam:glutaric acid which: a) has a PXRD diffraction pattern with peaks at about 5.16, 13.85, 15.26, 16.13, 19.64, 26.17 and 27.58+/–0.2 degrees two-theta; and/or b) has a PXRD diffraction pattern substantially as depicted in FIG. 13.

Figure 15:
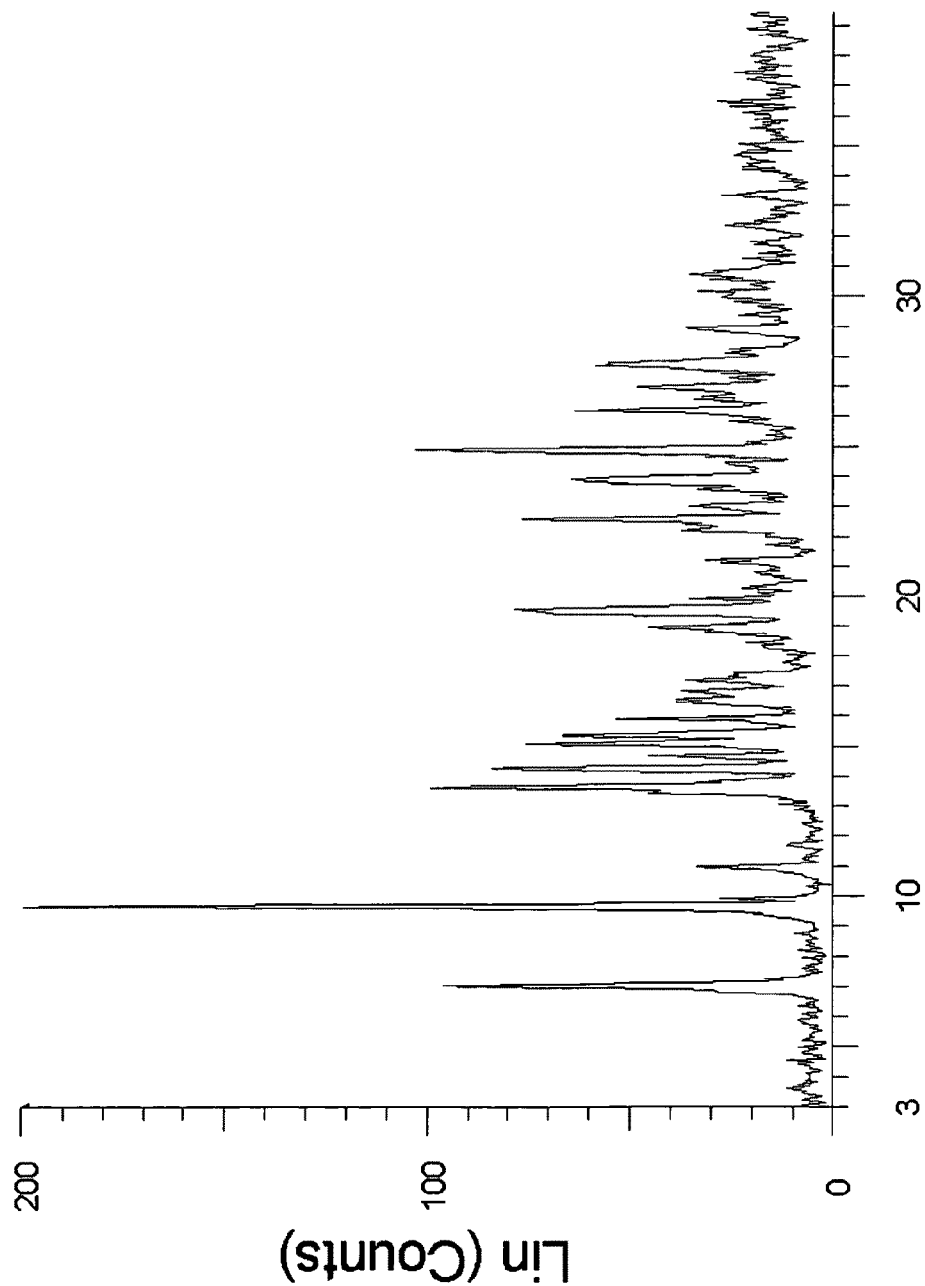

According to yet another aspect of the invention, there is provided a crystalline form of meloxicam wherein said crystalline form is co-crystal meloxicam:acetylsalicylic acid which: a) has a PXRD diffraction pattern with peaks at about 9.57, 13.55, 14.18, 19.49, 22.51, 23.86 and 24.88+/–0.2 degrees two-theta; and/or b) has a PXRD diffraction pattern substantially as depicted in FIG. 15.

Figure 17:
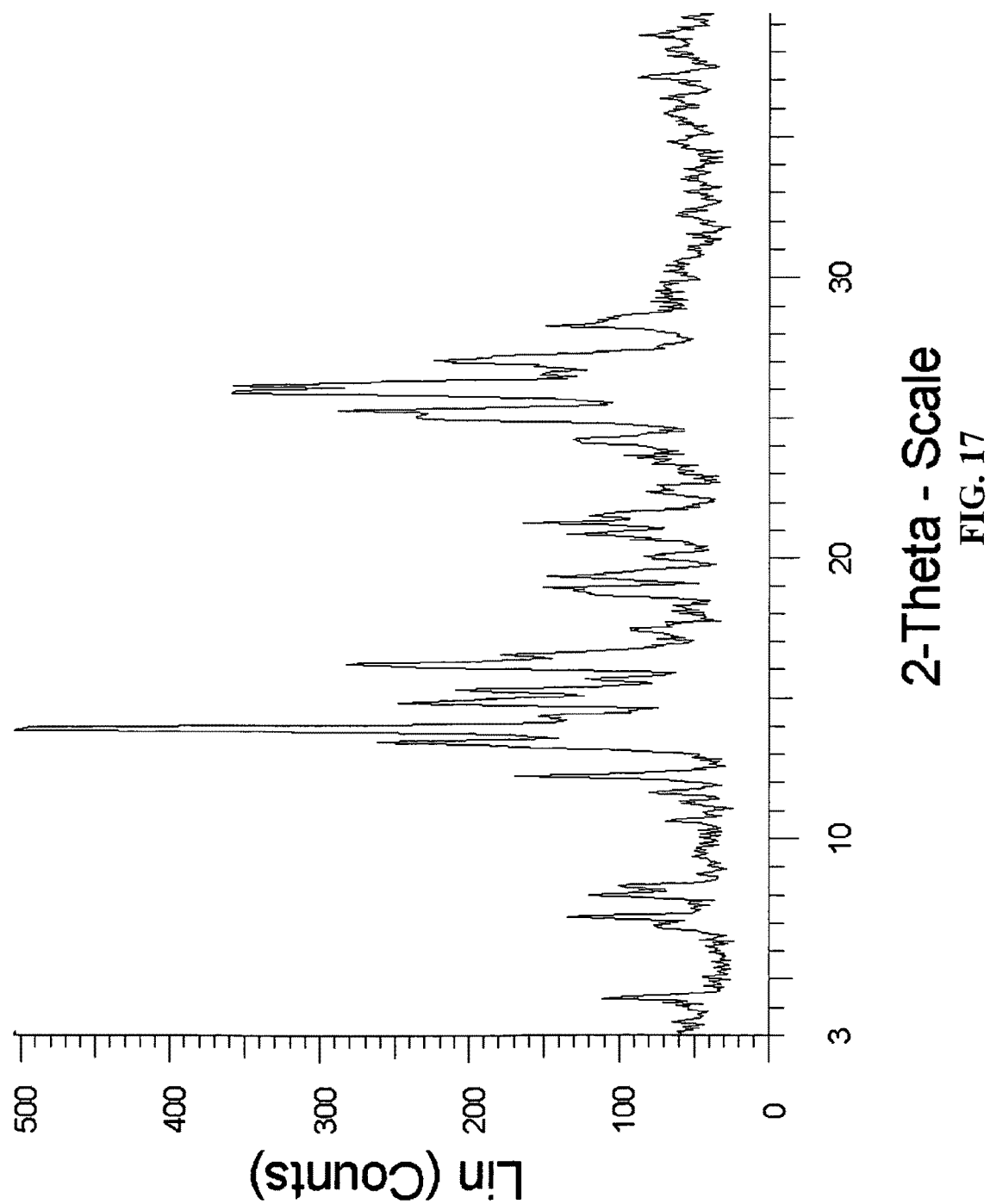

According to yet another aspect of the invention, there is provided a crystalline form of meloxicam wherein said crystalline form is co-crystal meloxicam:salicylic acid form I which: a) has a PXRD diffraction pattern with peaks at about 12.08, 13.85, 14.75, 16.10, 25.24, 25.87 and 27.00+/–0.2 degrees two-theta; and/or b) has a PXRD diffraction pattern substantially as depicted in FIG. 17.

Figure 19:
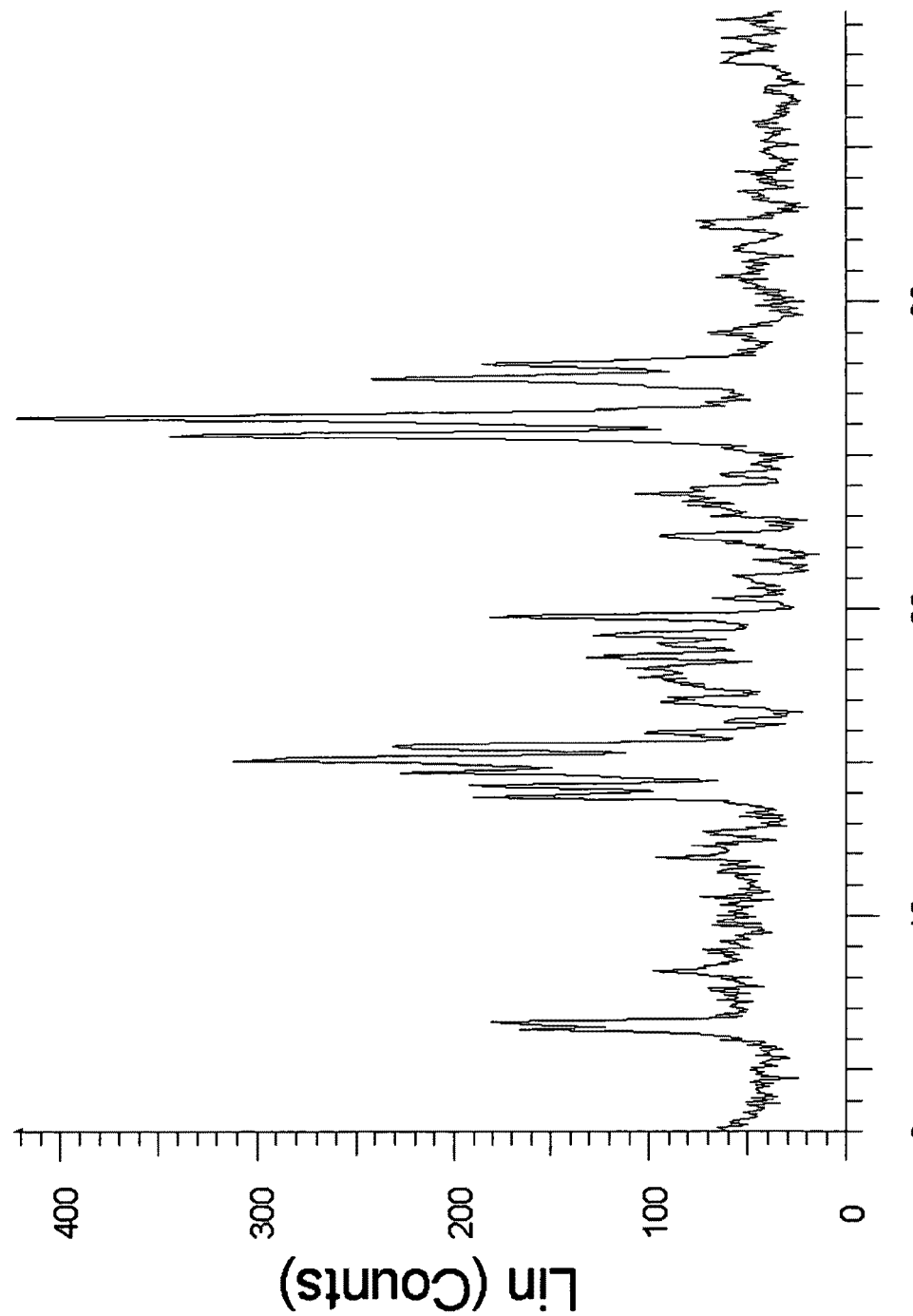

According to yet another aspect of the invention, there is provided a crystalline form of meloxicam wherein said crystalline form is co-crystal meloxicam:salicylic acid form II which: a) has a PXRD diffraction pattern with peaks at about 6.27, 15.02, 15.47, 19.70, 25.66, 26.23 and 27.49+/–0.2 degrees two-theta; and/or b) has a PXRD diffraction pattern substantially as depicted in FIG. 19.

Figure 41:
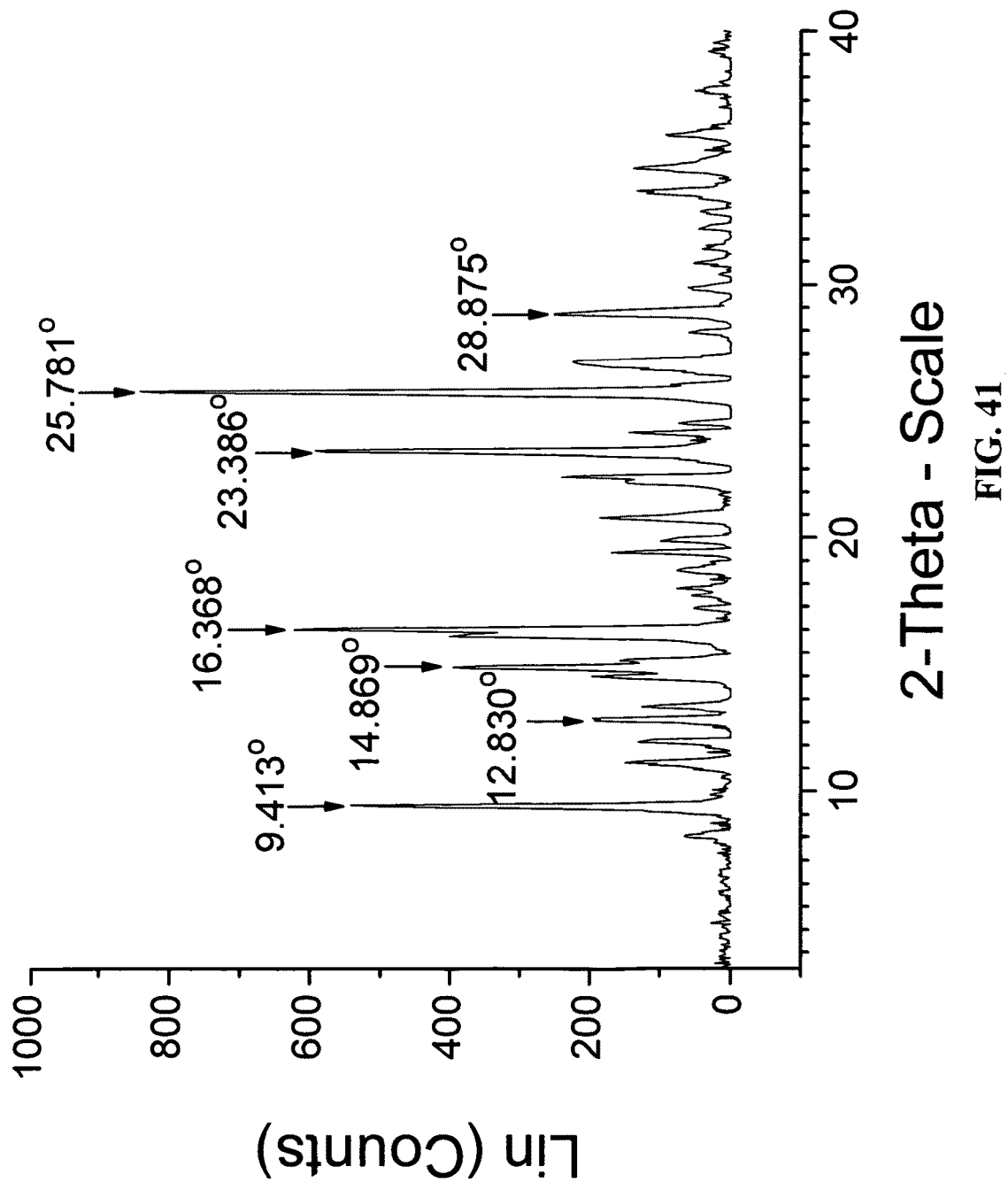

According to yet another aspect of the invention, there is provided a crystalline form of meloxicam wherein said crystalline form is co-crystal meloxicam:salicylic acid form III which: a) has a PXRD diffraction pattern with peaks at about 9.413, 12.830, 14.869, 16.368, 23.386, 25.781, and 28.875 +/– 0.2 degrees two-theta; and/or b) has a PXRD diffraction pattern substantially as depicted in FIG. 41.

Figure 21:
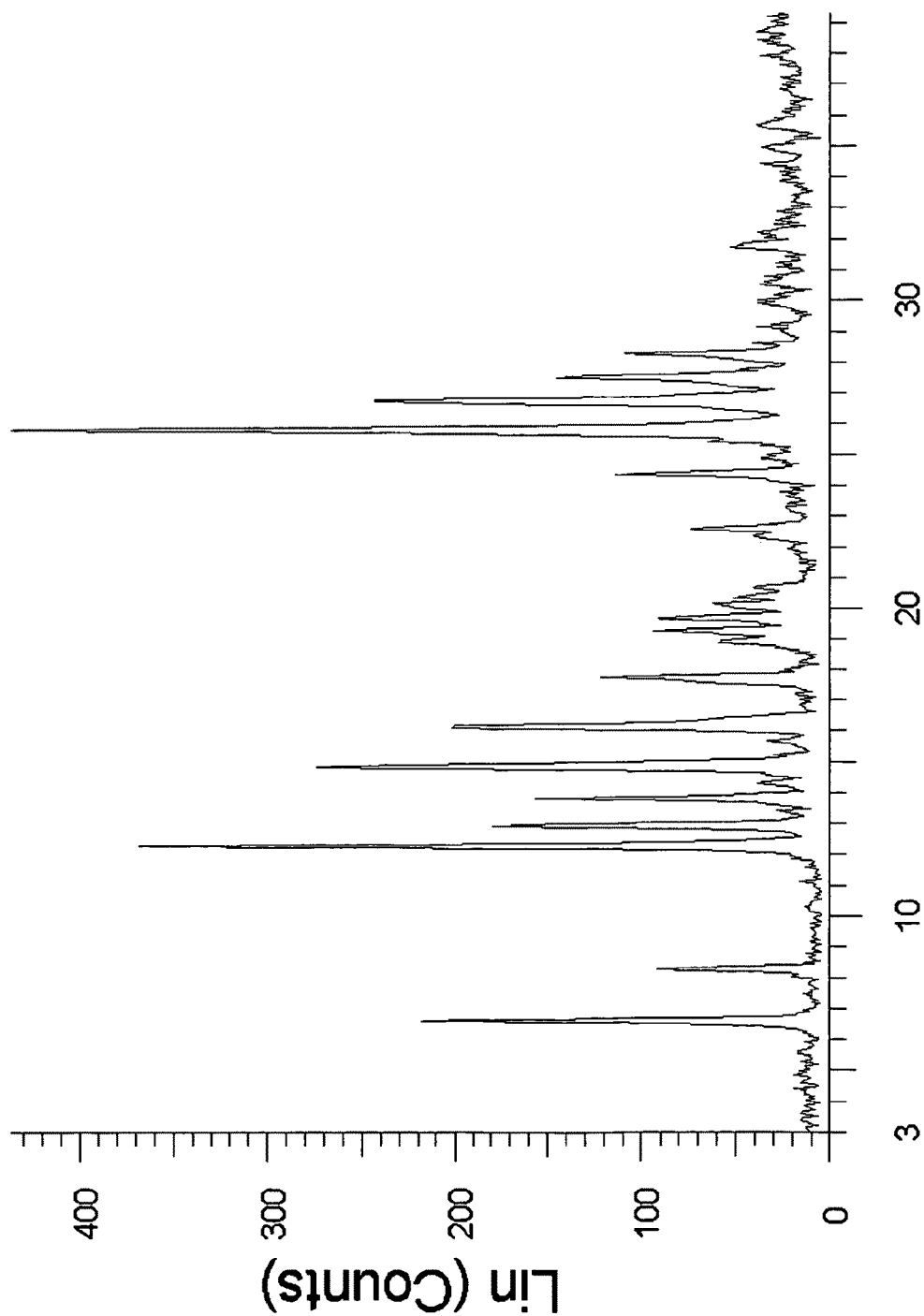

According to yet another aspect of the invention, there is provided a crystalline form of meloxicam wherein said crystalline form is co-crystal meloxicam: 1-hydroxy-2-naphthoic acid which: a) has a PXRD diffraction pattern with peaks at about 6.67, 12.35, 14.92, 16.25, 17.75, 25.93 and 26.88+/–0.2 degrees two-theta; and/or b) has a PXRD diffraction pattern substantially as depicted in FIG. 21.

Figure 23:
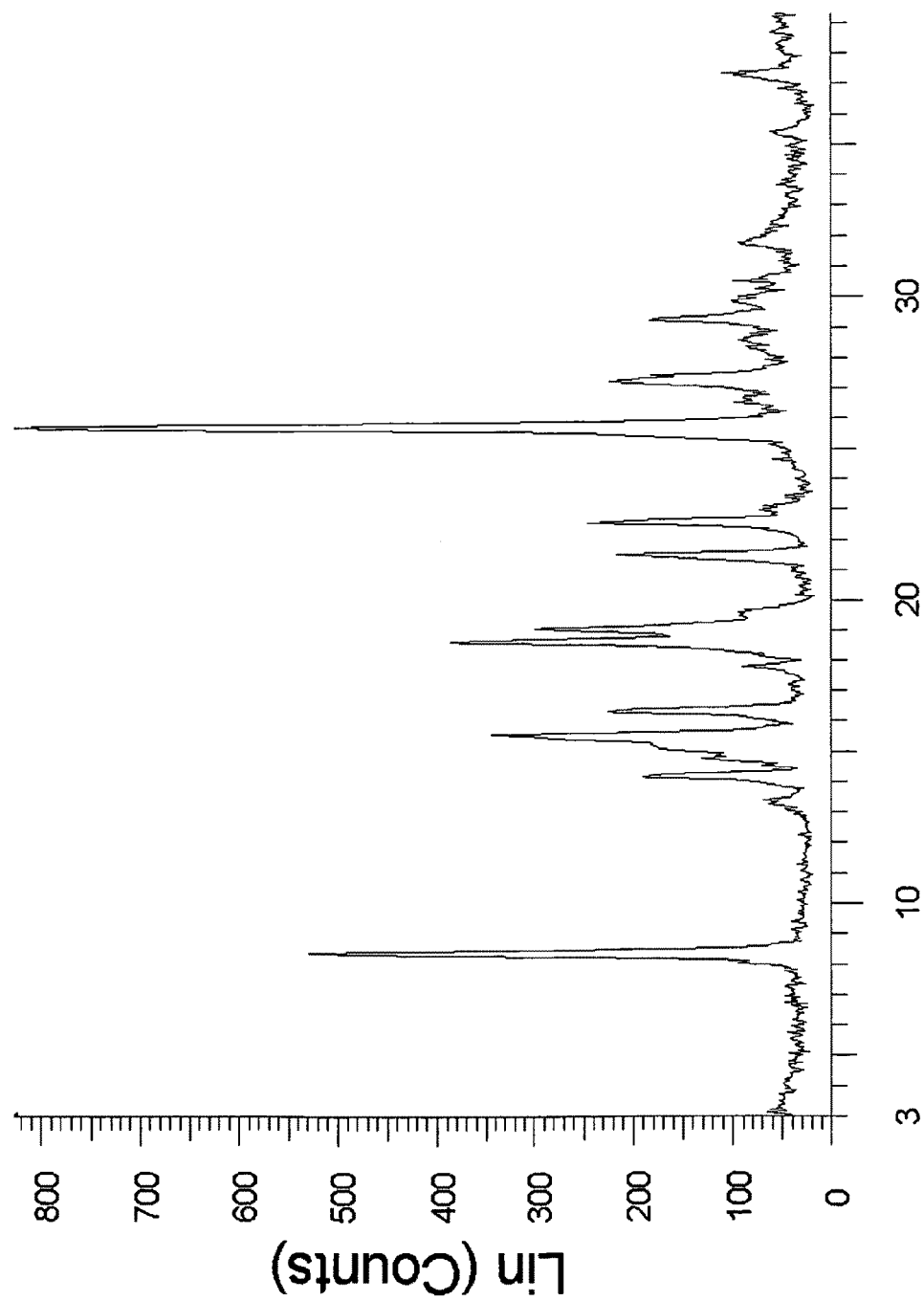

According to yet another aspect of the invention, there is provided a crystalline form of meloxicam wherein said crystalline form is co-crystal meloxicam:maleic acid which: a) has a PXRD diffraction pattern with peaks at about 8.27, 15.50, 16.35, 18.59, 21.43, 22.58 and 25.69+/–0.2 degrees two-theta; and/or b) has a PXRD diffraction pattern substantially as depicted in FIG. 23.

Figure 25:
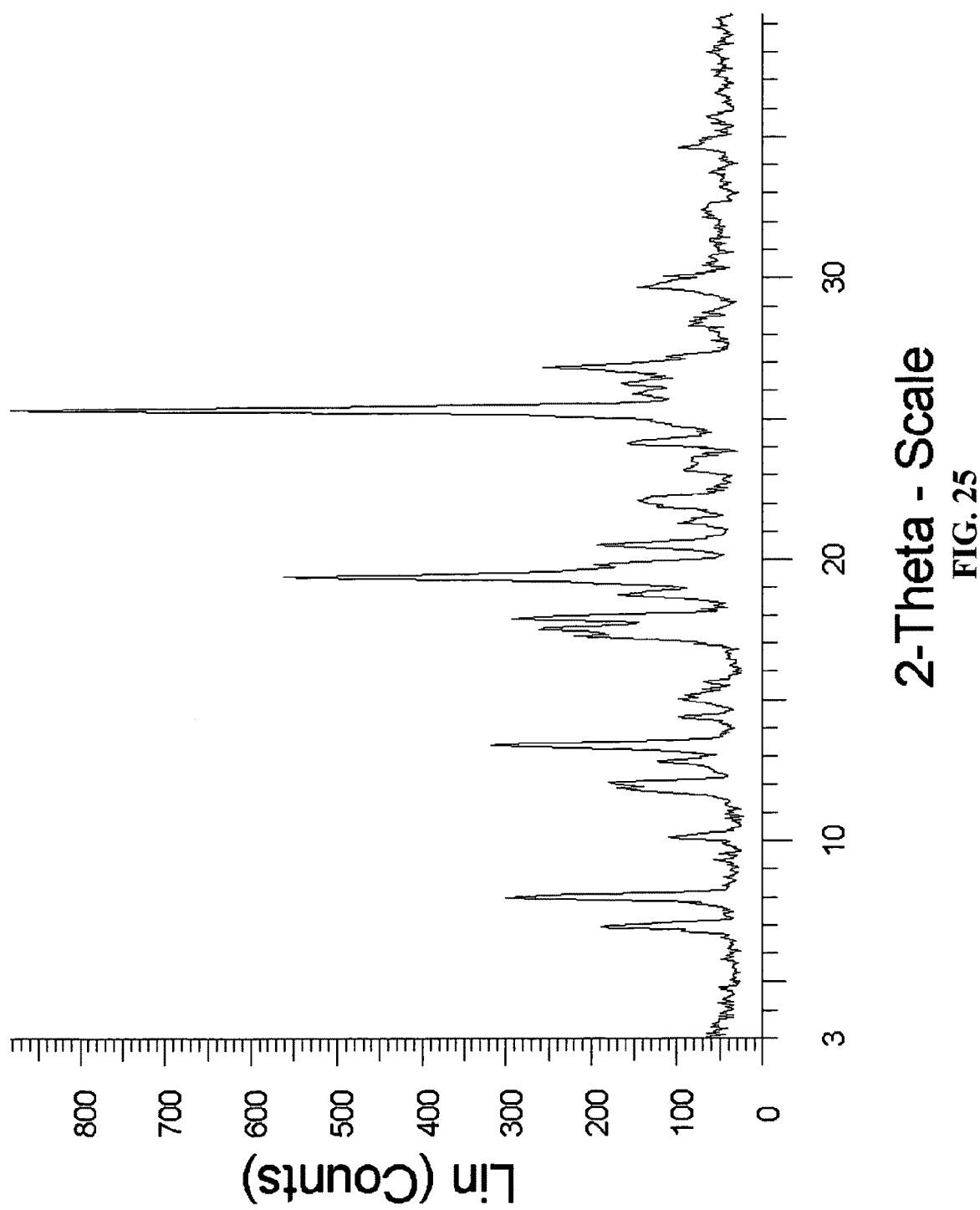

According to yet another aspect of the invention, there is provided a crystalline form of meloxicam wherein said crystalline form is co-crystal meloxicam:4-hydroxybenzoic acid which: a) has a PXRD diffraction pattern with peaks at about 6.88, 7.92, 13.34, 17.87, 19.41, 25.36 and 26.86+/–0.2 degrees two-theta; and/or b) has a PXRD diffraction pattern substantially as depicted in FIG. 25.

Figure 27:
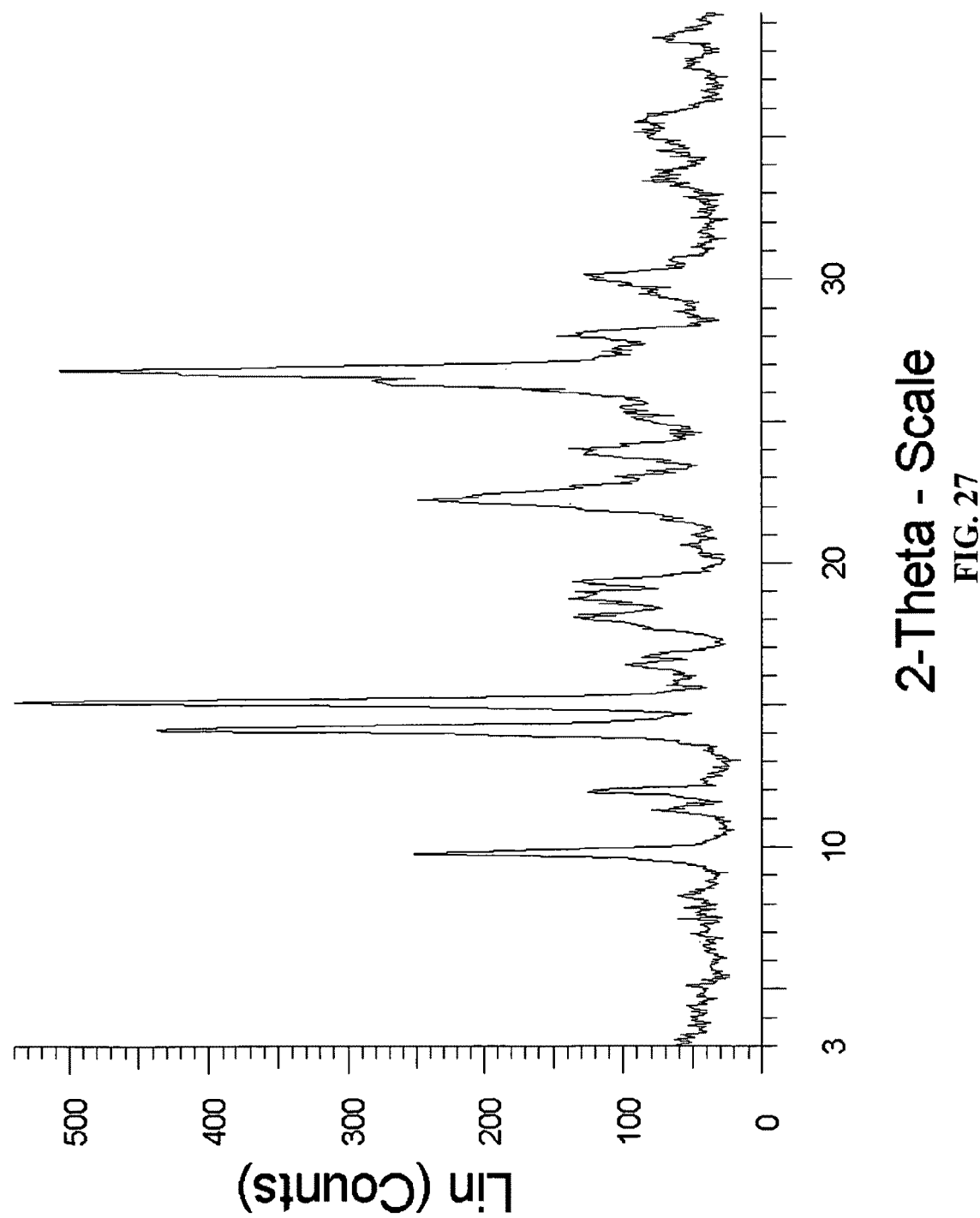

According to yet another aspect of the invention, there is provided a crystalline form of meloxicam wherein said crystalline form is co-crystal meloxicam:malonic acid which: a) has a PXRD diffraction pattern with peaks at about 9.74, 11.88, 14.06, 15.02, 19.34, 22.27 and 26.83+/−0.2 degrees two-theta; and/or b) has a PXRD diffraction pattern substantially as depicted in FIG. 27.

Figure 29:
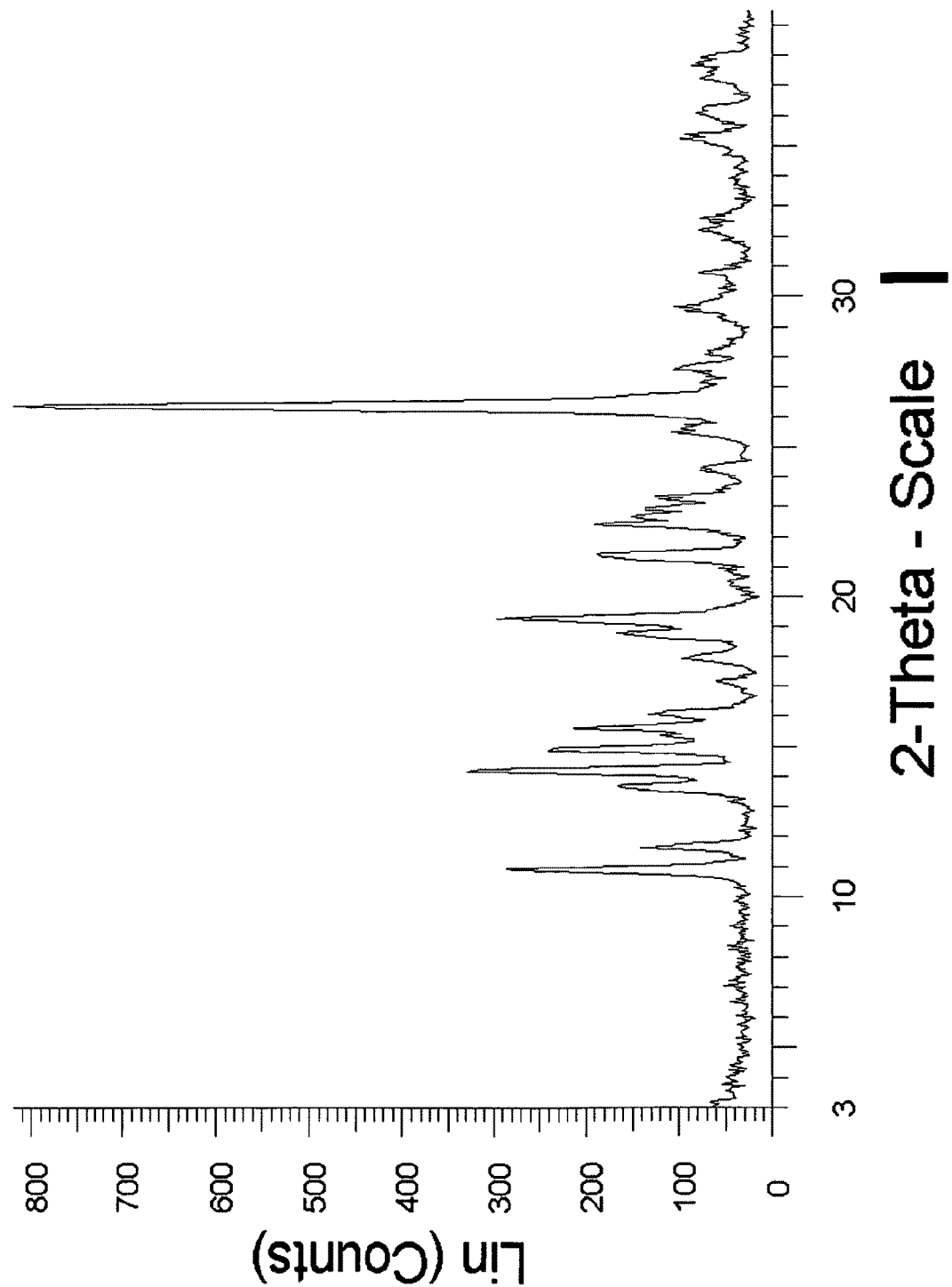

According to yet another aspect of the invention, there is provided a crystalline form of meloxicam wherein said crystalline form is co-crystal meloxicam:glycolic acid which: a) has a PXRD diffraction pattern with peaks at about 10.91, 14.18, 14.87, 15.56, 19.28, 21.37 and 26.38+/−0.2 degrees two-theta; and/or b) has a PXRD diffraction pattern substantially as depicted in FIG. 29.

Figure 31:
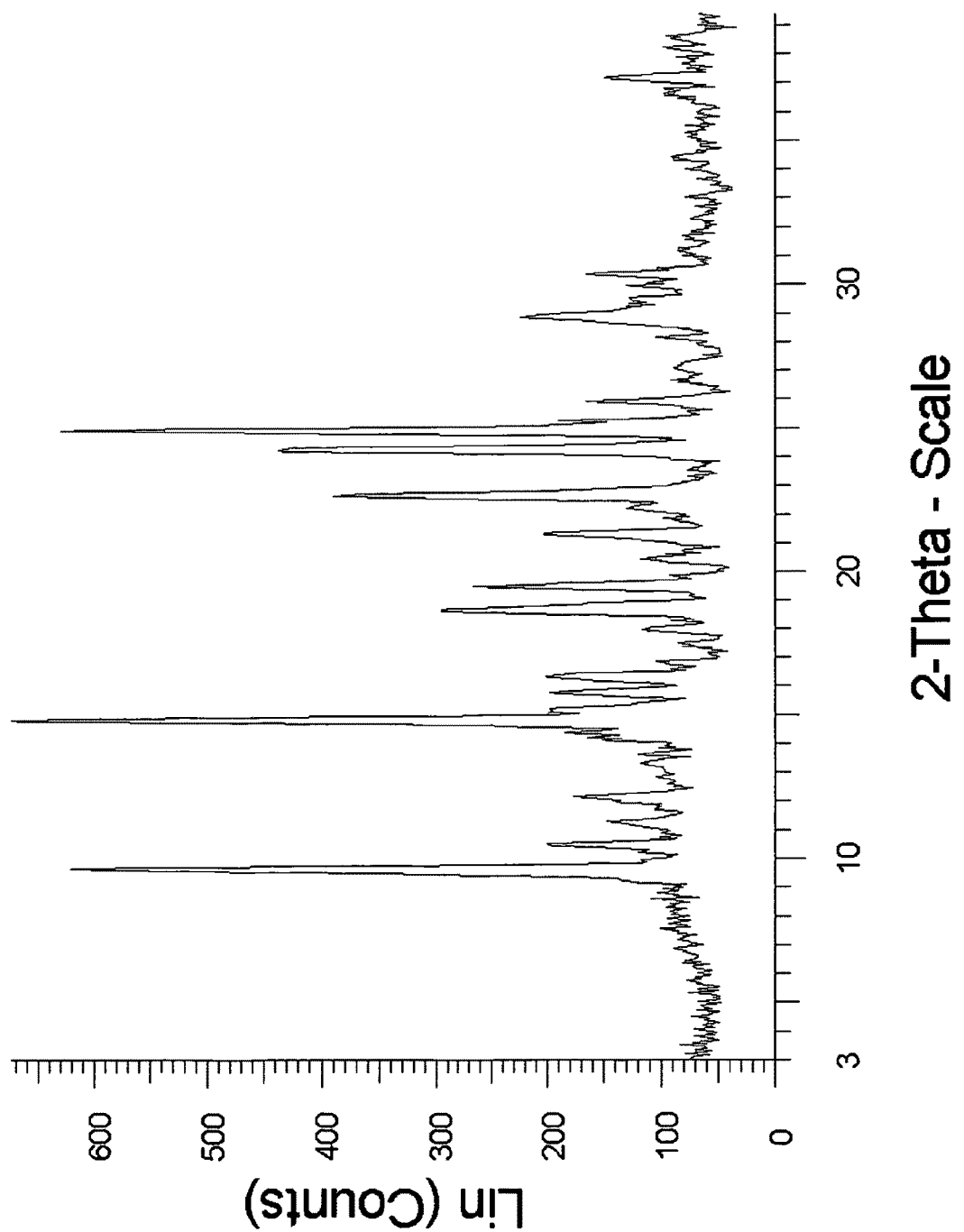

According to yet another aspect of the invention, there is provided a crystalline form of meloxicam wherein said crystalline form is co-crystal meloxicam:2,5-dihydroxybenzoic acid form I which: a) has a PXRD diffraction pattern with peaks at about 9.77, 14.96, 18.84, 22.85, 24.43, 25.12 and 29.02+/−0.2 degrees two-theta; and/or b) has a PXRD diffraction pattern substantially as depicted in FIG. 31.

Figure 33:
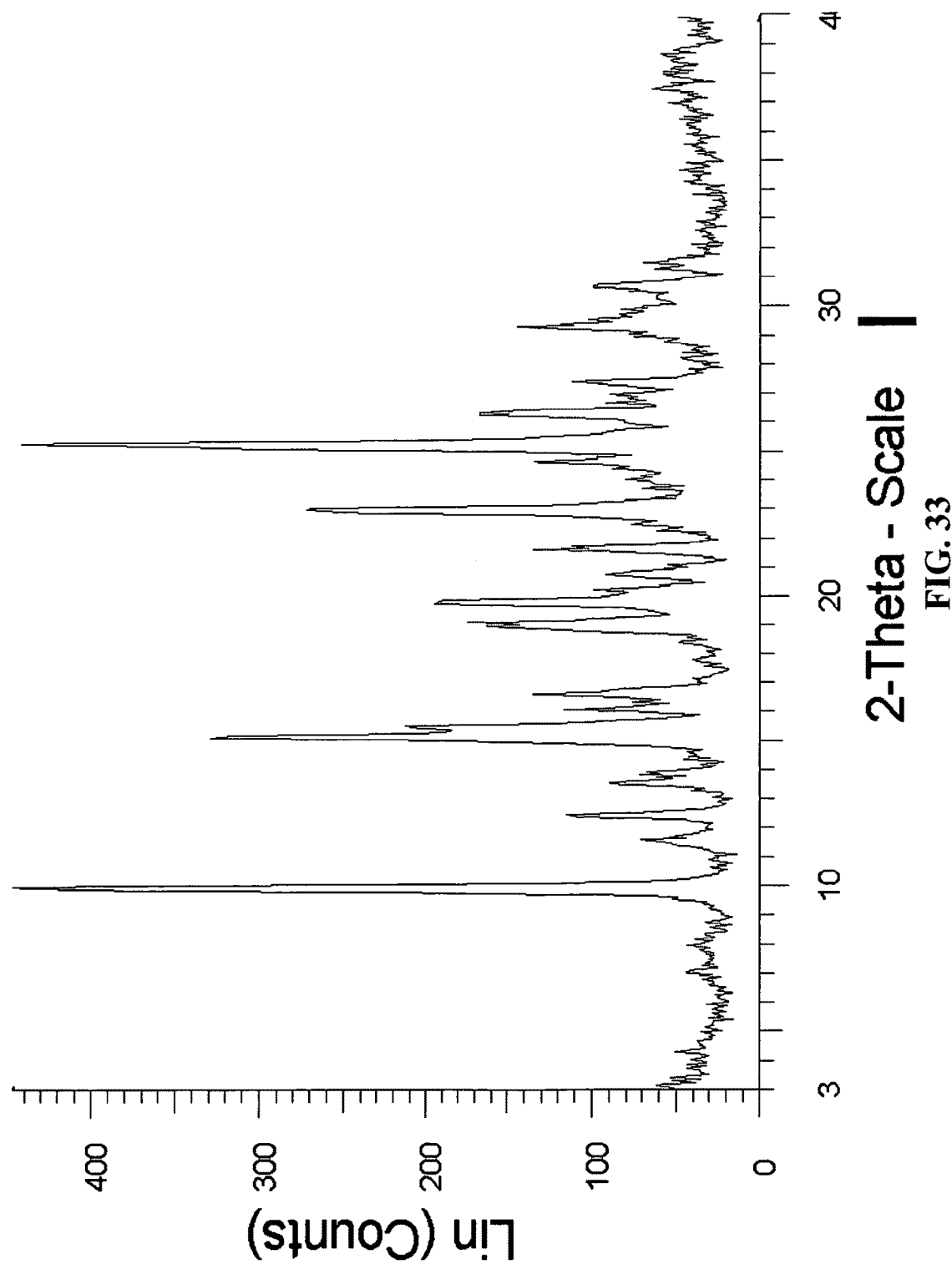

According to yet another aspect of the invention, there is provided a crystalline form of meloxicam wherein said crystalline form is co-crystal meloxicam:2,5-dihydroxybenzoic acid form II which: a) has a PXRD diffraction pattern with peaks at about 9.86, 15.05, 19.07, 19.79, 22.99, 25.27 and 26.32+/−0.2 degrees two-theta; and/or b) has a PXRD diffraction pattern substantially as depicted in FIG. 33.

Figure 35:
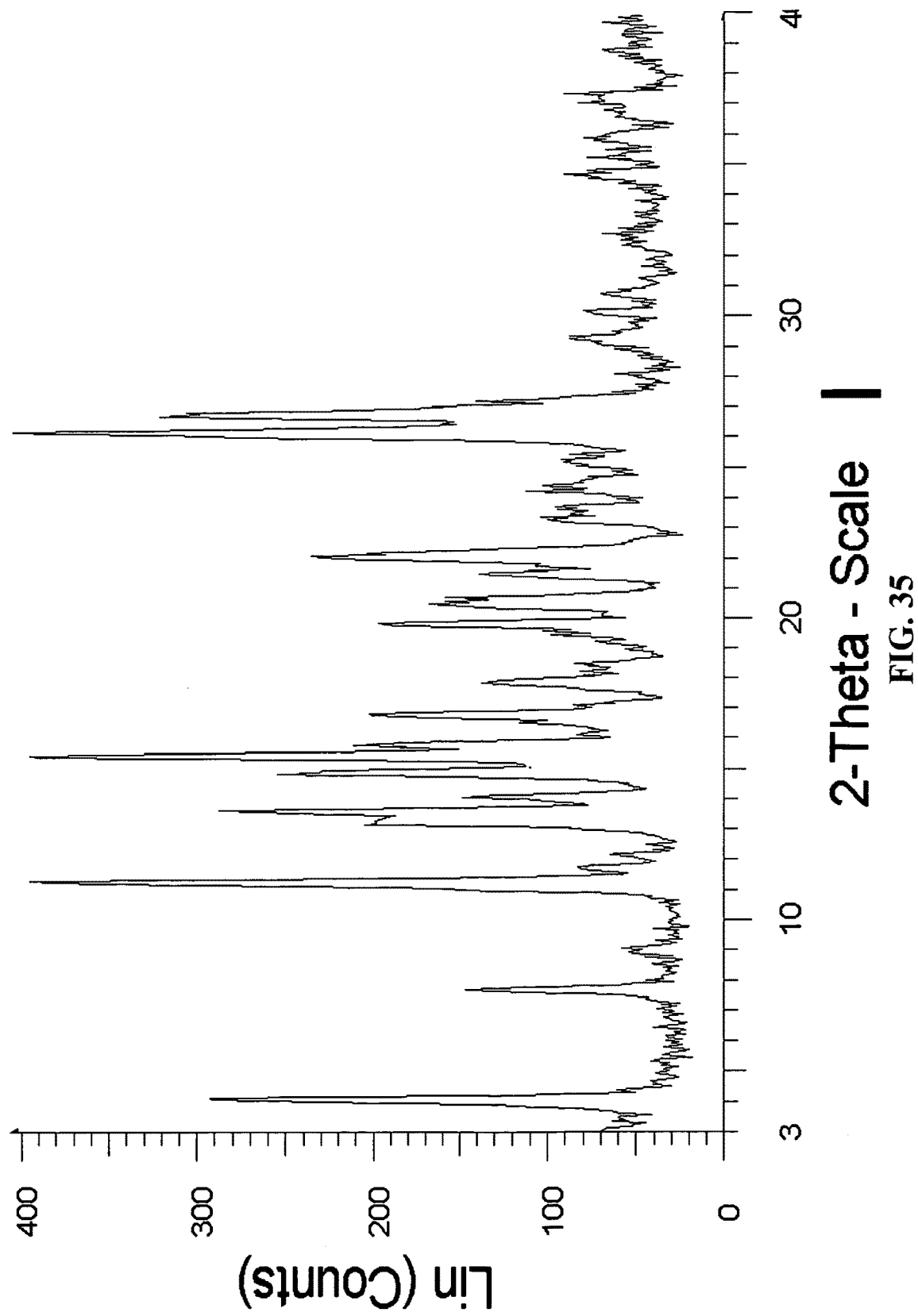

According to yet another aspect of the invention, there is provided a crystalline form of meloxicam wherein said crystalline form is co-crystal meloxicam:camphoric acid form I which: a) has a PXRD diffraction pattern with peaks at about 4.107, 7.68, 11.35, 13.64, 15.47, 26.23 and 26.83+/− 0.2 degrees two-theta; and/or b) has a PXRD diffraction pattern substantially as depicted in FIG. 35.

Figure 37:
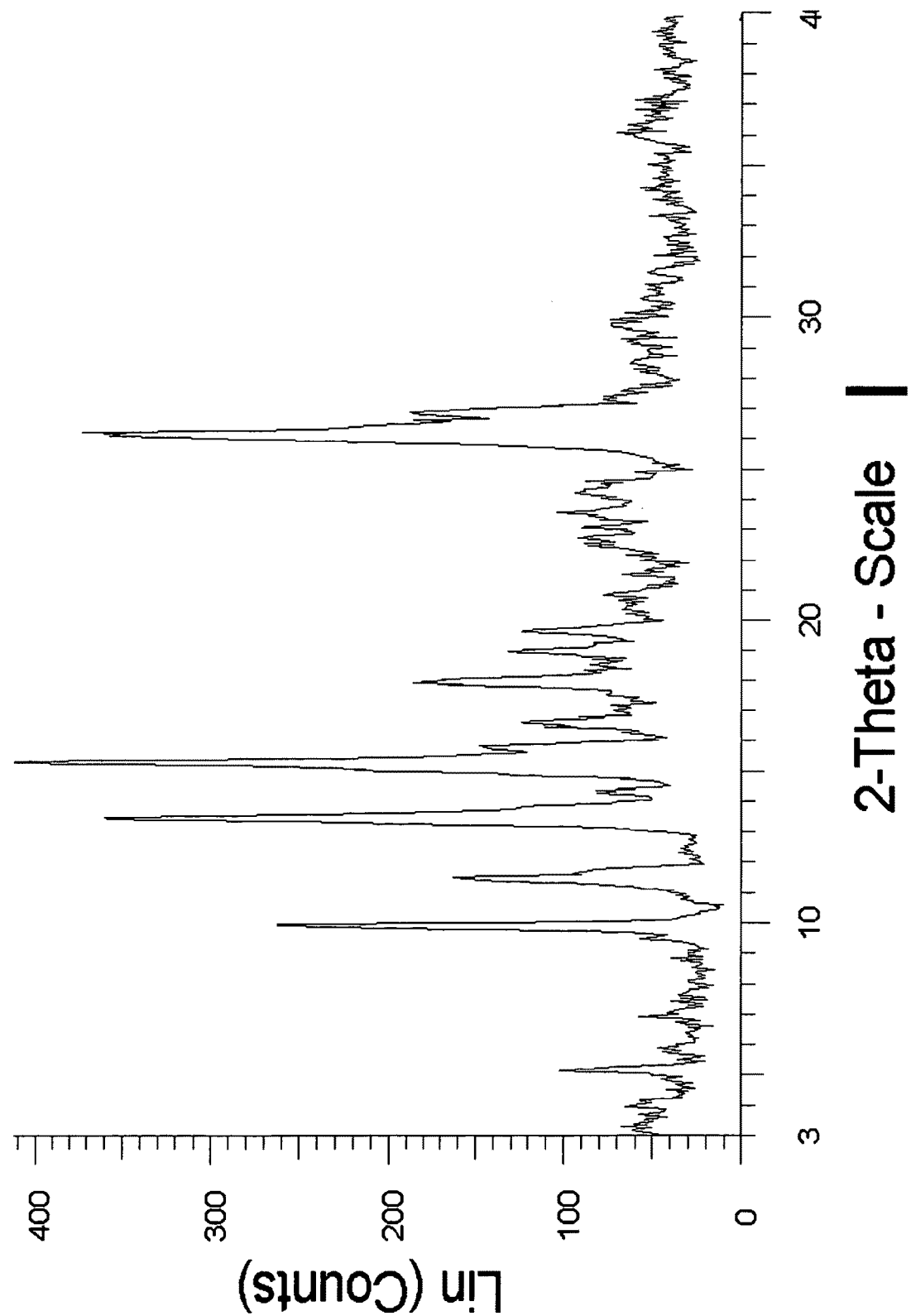

According to yet another aspect of the invention, there is provided a crystalline form of meloxicam wherein said crystalline form is co-crystal meloxicam:camphoric acid form II which: a) has a PXRD diffraction pattern with peaks at about 5.19, 9.95, 11.41, 13.50, 15.38, 16.70, 26.23 and 36.21+/−0.2 degrees two-theta; and/or b) has a PXRD diffraction pattern substantially as depicted in FIG. 37.

Figure 39:
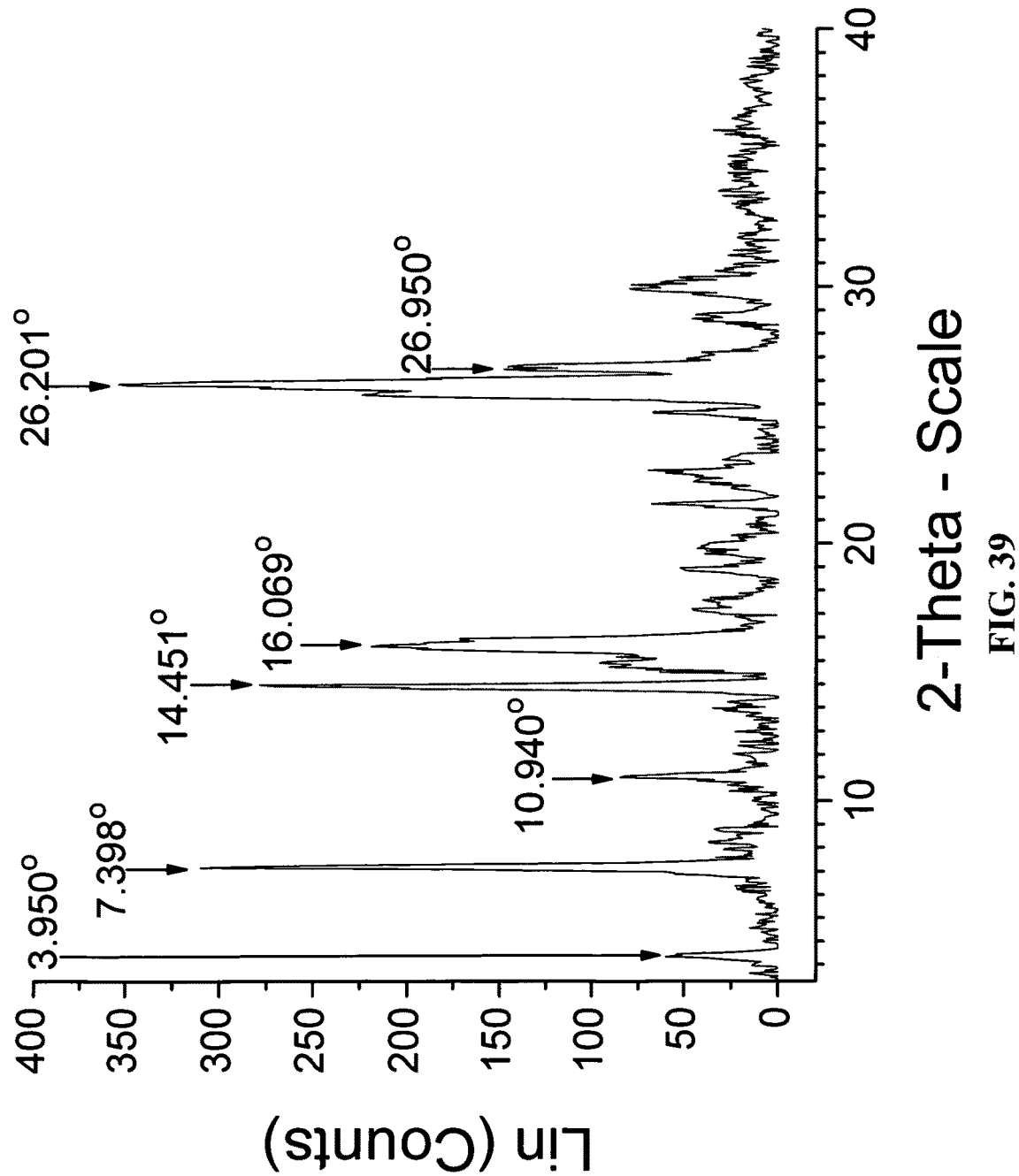

According to yet another aspect of the invention, there is provided a crystalline form of meloxicam wherein said crystalline form is co-crystal meloxicam:maltol which: a) has a PXRD diffraction pattern with peaks at about 3.950, 7.398, 10.940, 14.451, 16.069, 26.201, and 26.950+/− 0.2 degrees two-theta; and/or b) has a PXRD diffraction pattern substantially as depicted in FIG. 39.

Figure 43:
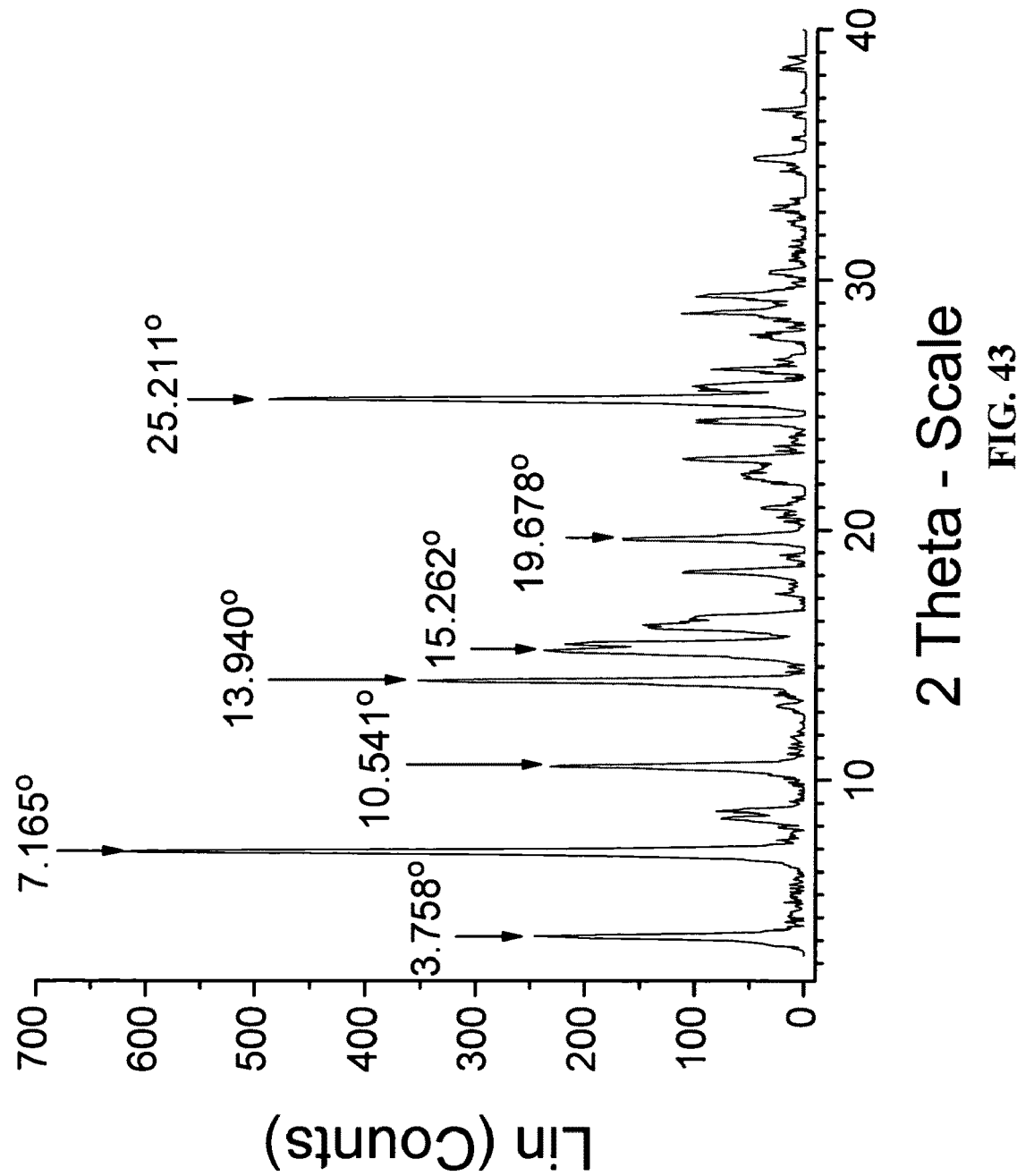

According to yet another aspect of the invention, there is provided a crystalline form of meloxicam wherein said crystalline form is co-crystal meloxicam:ethyl maltol which: a) has a PXRD diffraction pattern with peaks at about 3.758, 7.165, 10.541, 13.940, 15.262, 19.678, and 25.211+/− 0.2 degrees two-theta; and/or b) has a PXRD diffraction pattern substantially as depicted in FIG. 43.

Figure 45:
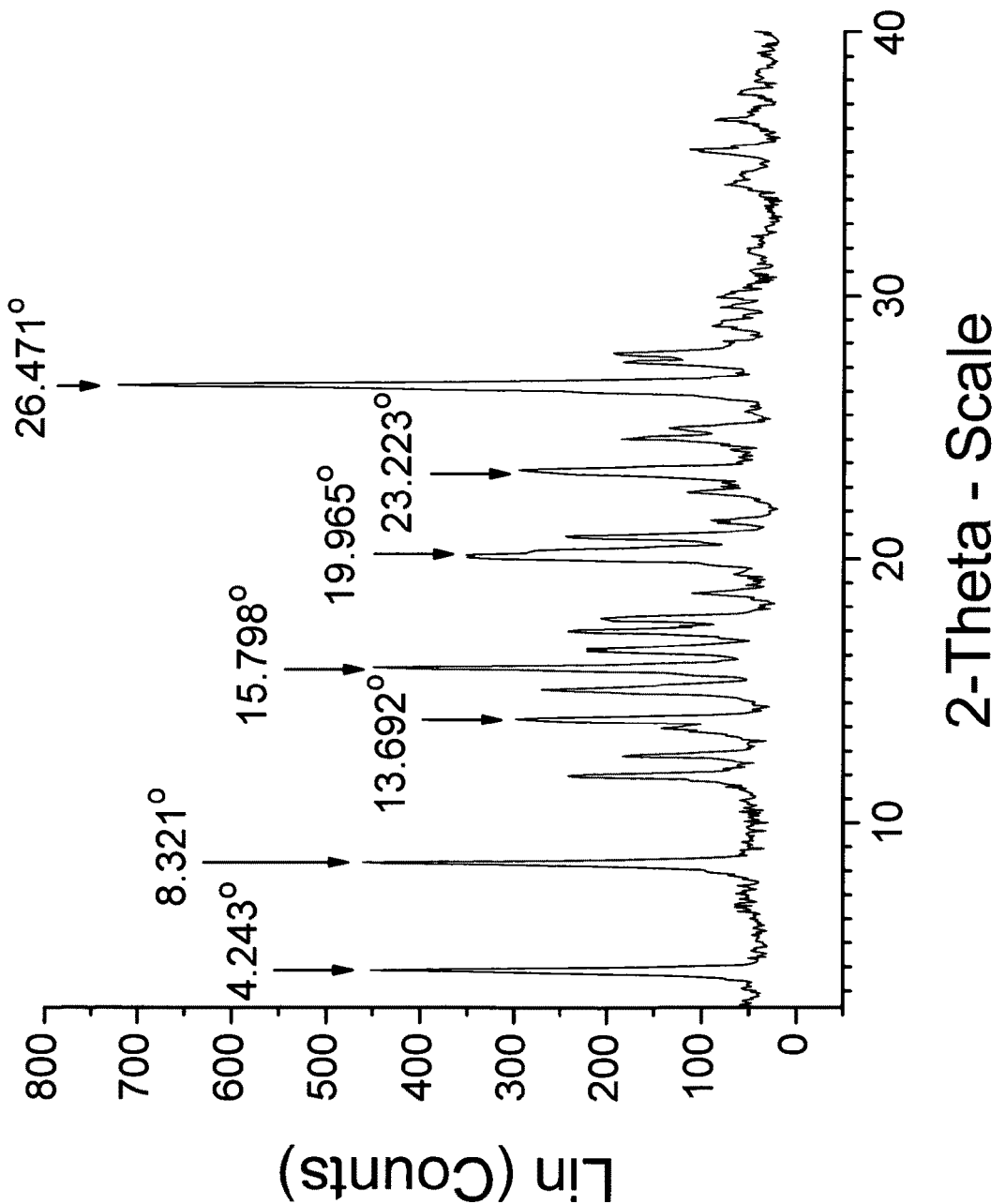

According to yet another aspect of the invention, there is provided a crystalline form of meloxicam wherein said crystalline form is co-crystal meloxicam:hydrocinnamic acid which: a) has a PXRD diffraction pattern with peaks at about 4.243, 8.321, 13.692, 15.798, 19.965, 23.223, and 26.471 +/− 0.2 degrees two-theta; and/or b) has a PXRD diffraction pattern substantially as depicted in FIG. 45.

Another aspect of the present invention is a pharmaceutical composition comprising an effective amount of one or more of the crystalline forms of meloxicam disclosed herein and a pharmaceutically acceptable excipient.

BRIEF DESCRIPTION OF THE DRAWINGS AND TABLES

The foregoing and other features and advantages of the disclosed technology will become more apparent from the following detailed description, which proceeds with reference to the accompanying drawings. Such description is meant to be illustrative, and not limiting, of the invention.

FIG. 1—PXRD diffractogram of a cocrystal comprising meloxicam and fumaric acid (2:1).

Figure 2:
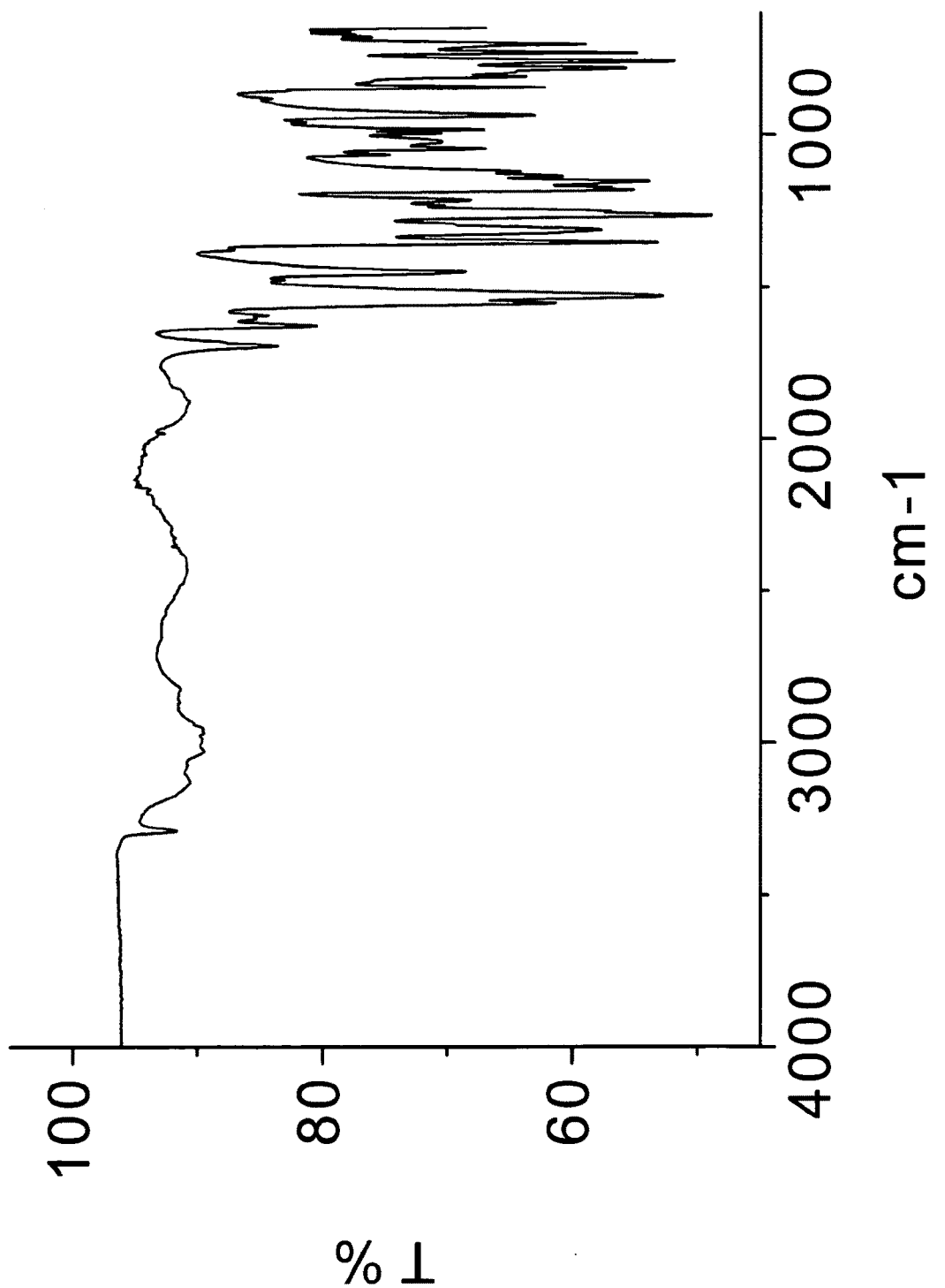

FIG. 2—FTIR spectrum of a cocrystal comprising meloxicam and fumaric acid (2:1).

FIG. 3—PXRD diffractogram of a cocrystal comprising meloxicam and succinic acid (2:1).

Figure 4:
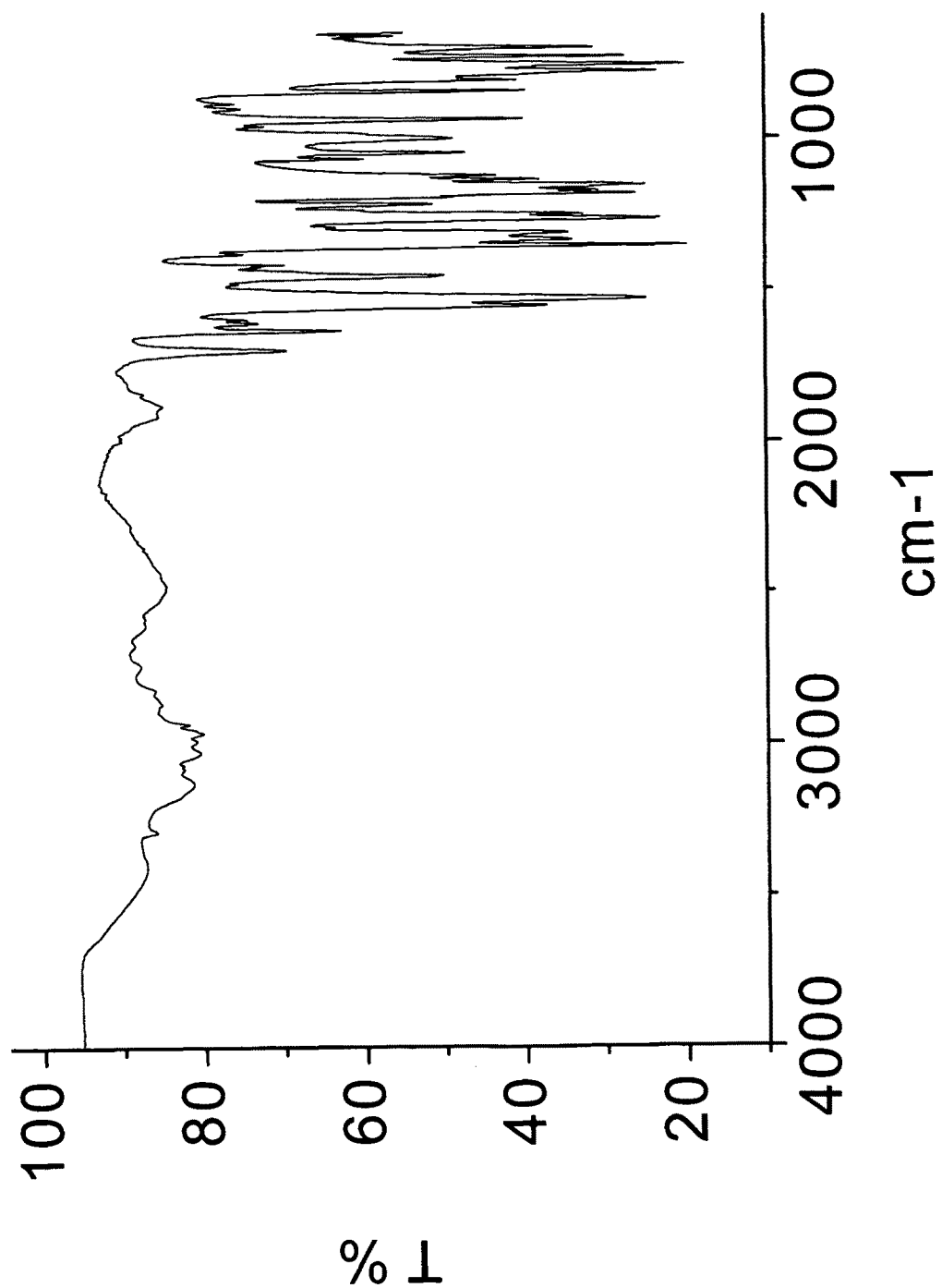

FIG. 4—FTIR spectrum of a cocrystal comprising meloxicam and succinic acid (2:1).

FIG. 5—PXRD diffractogram of a cocrystal comprising meloxicam and adipic acid (2:1).

Figure 6:
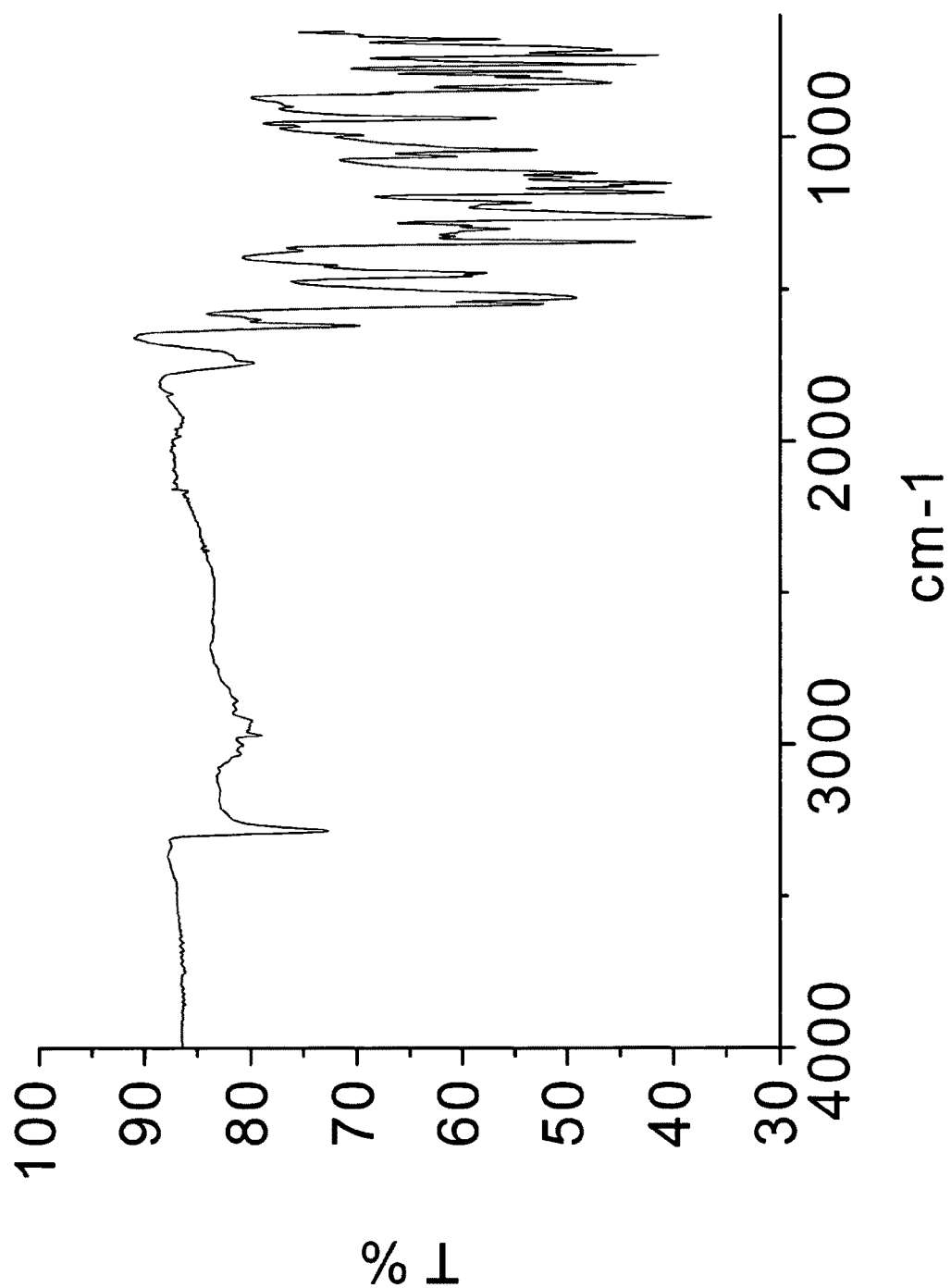

FIG. 6—FTIR spectrum of a cocrystal comprising meloxicam and adipic acid (2:1).

FIG. 7—PXRD diffractogram of a cocrystal comprising meloxicam and benzoic acid (1:1).

Figure 8:
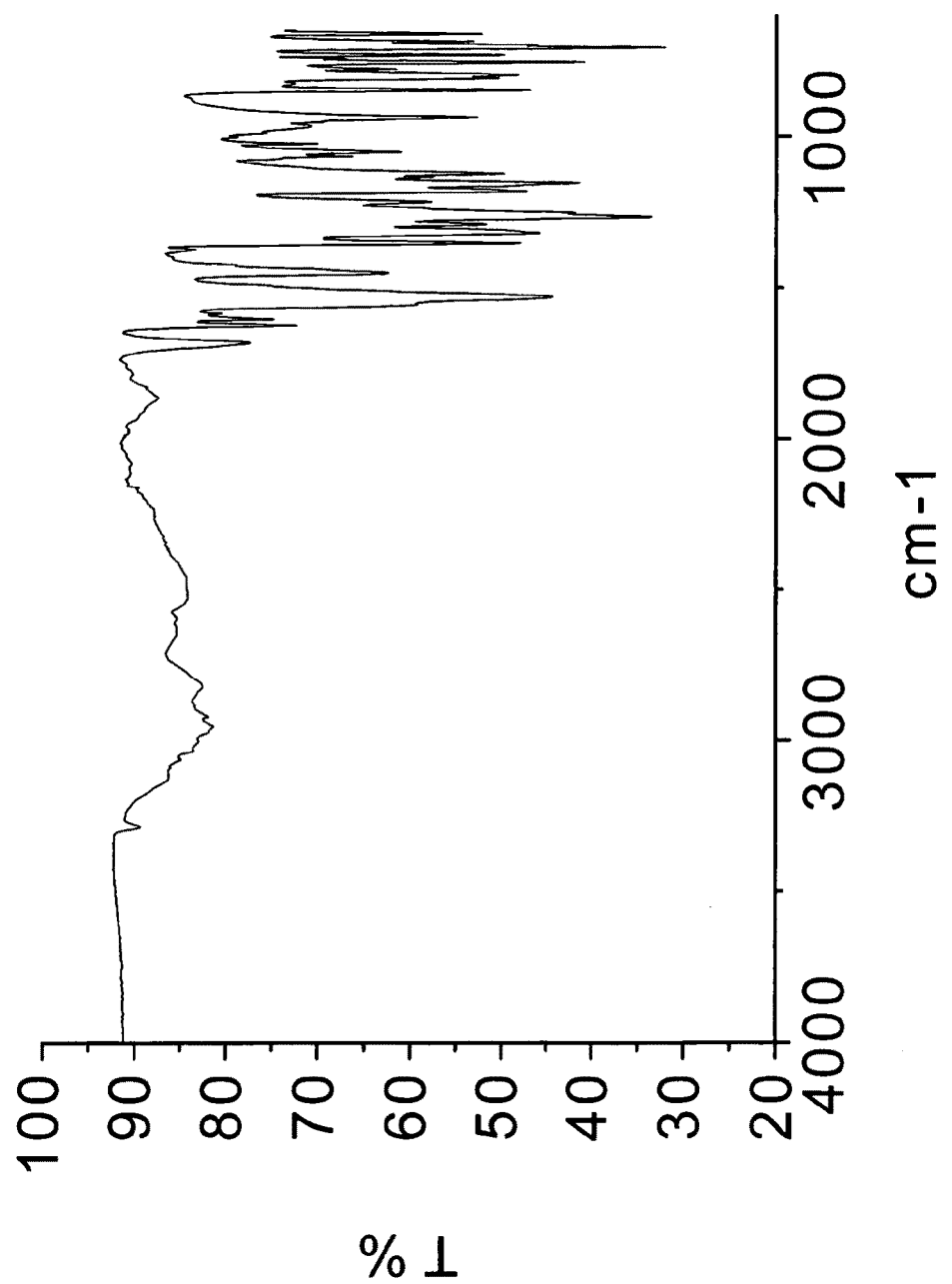

FIG. 8—FTIR spectrum of a cocrystal comprising meloxicam and benzoic acid (1:1).

FIG. 9—PXRD diffractogram of a cocrystal comprising meloxicam and DL-malic acid (2:1).

Figure 10:
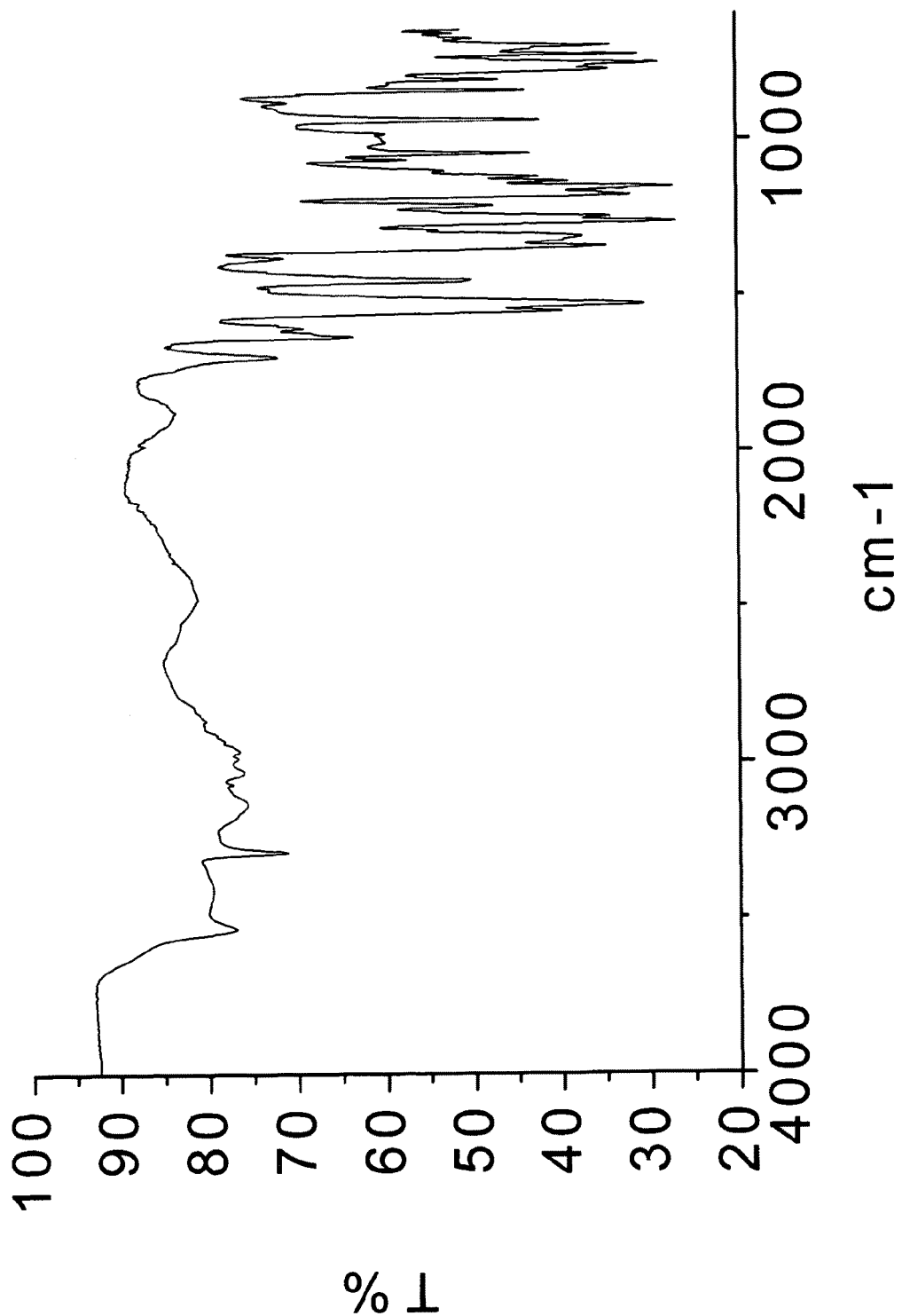

FIG. 10—FTIR spectrum of a cocrystal comprising meloxicam and DL-malic acid (2:1).

FIG. 11—PXRD diffractogram of a cocrystal comprising meloxicam and L-malic acid (2:1).

Figure 12:
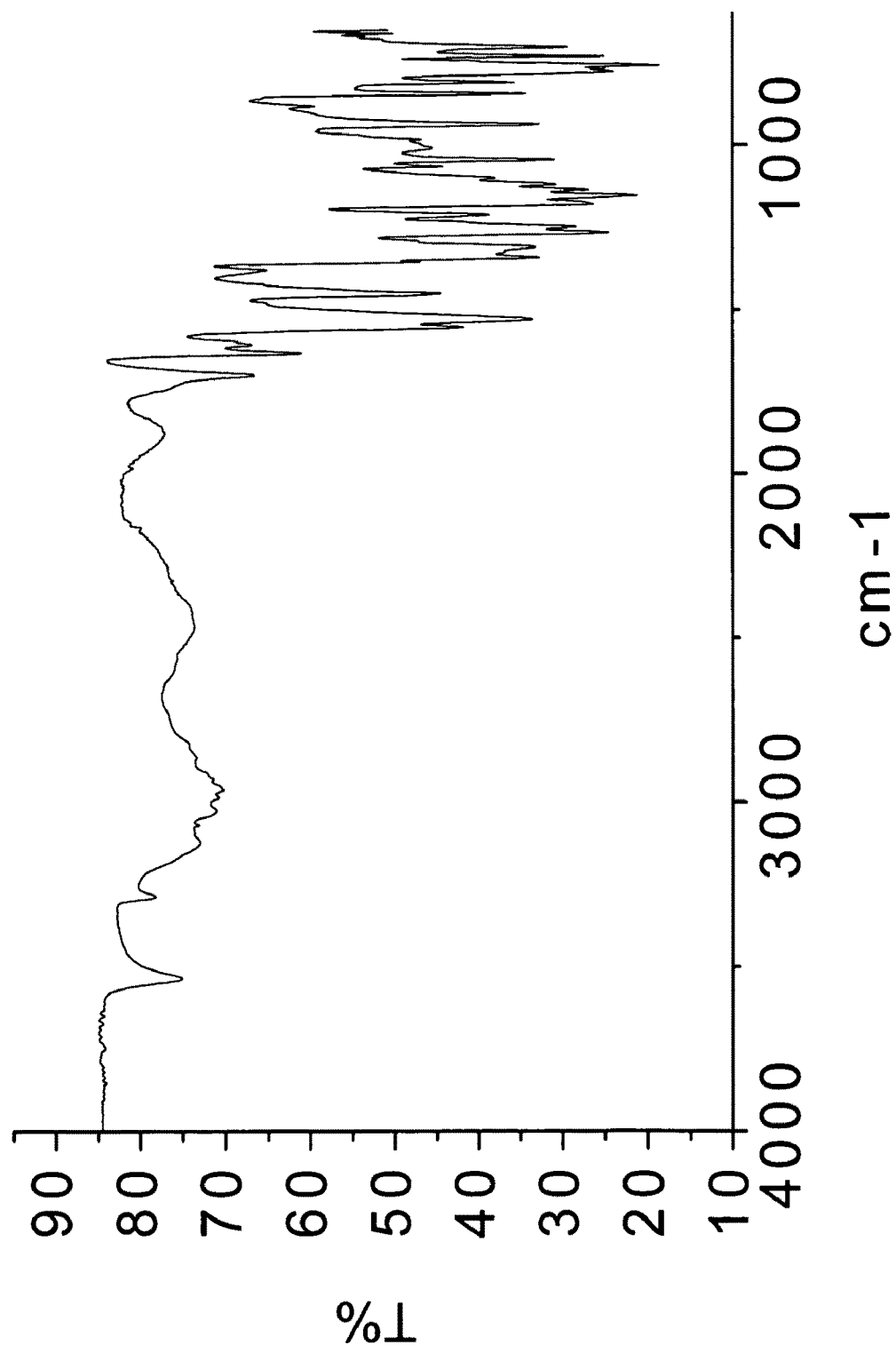

FIG. 12—FTIR spectrum of a cocrystal comprising meloxicam and L-malic acid (2:1).

FIG. 13—PXRD diffractogram of a cocrystal comprising meloxicam and glutaric acid (1:1).

Figure 14:
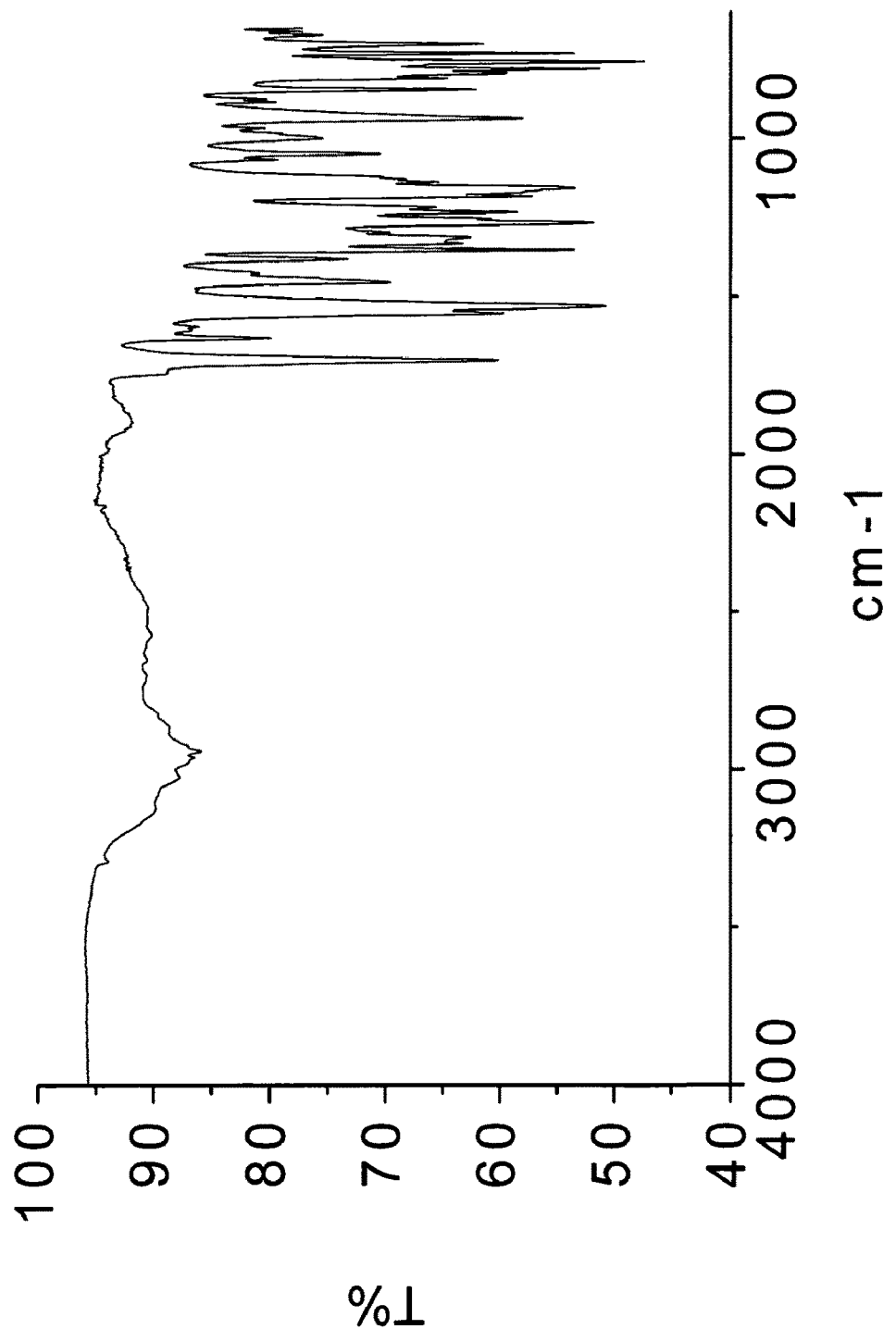

FIG. 14—FTIR spectrum of a cocrystal comprising meloxicam and glutaric acid (1:1).

FIG. 15—PXRD diffractogram of a cocrystal comprising meloxicam and aspirin (acetylsalicylic acid) (1:1).

Figure 16:
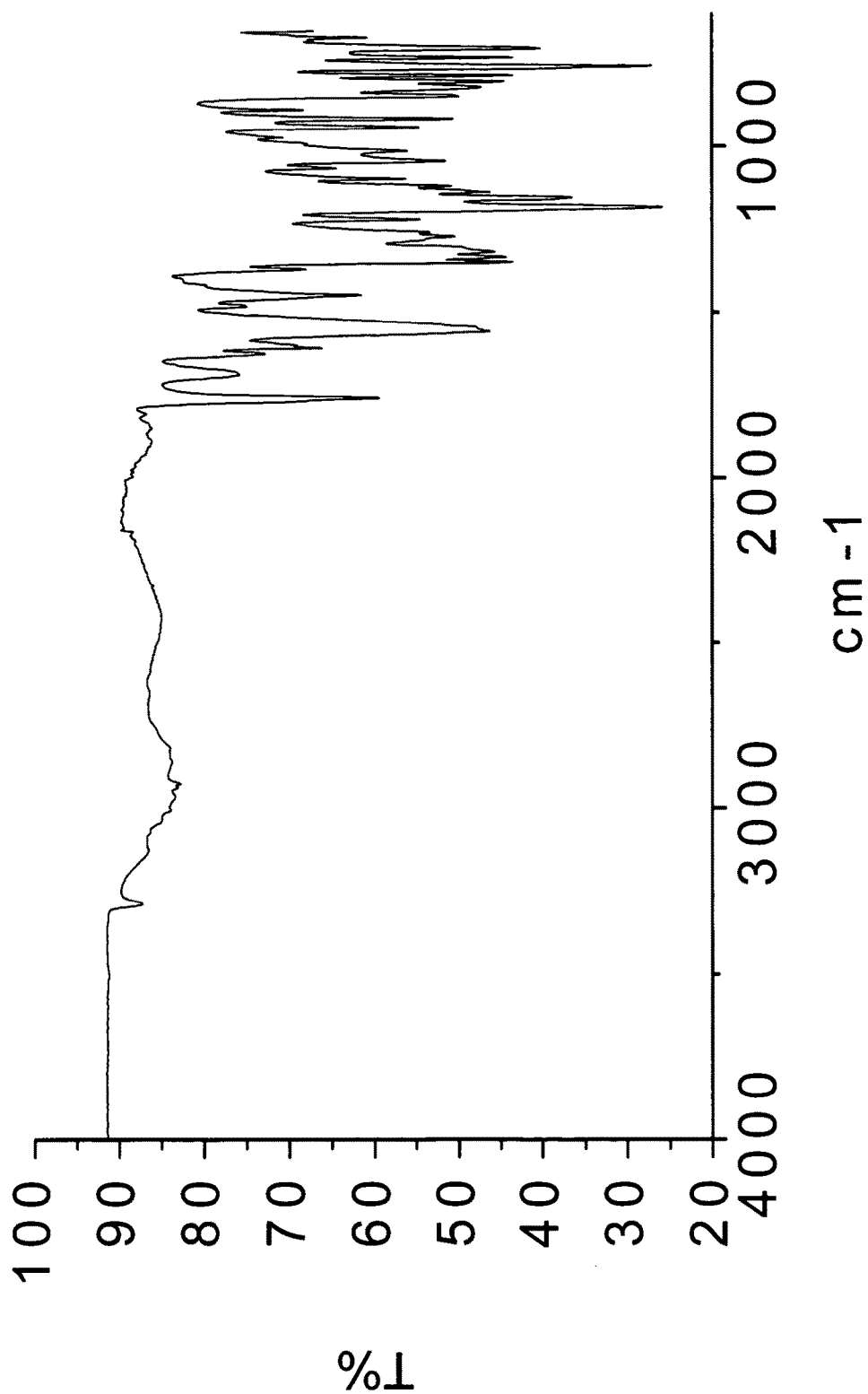

FIG. 16—FTIR spectrum of a cocrystal comprising meloxicam and aspirin (acetylsalicylic acid) (1:1).

FIG. 17—PXRD diffractogram of a cocrystal form I comprising meloxicam and salicylic acid (1:1).

Figure 18:
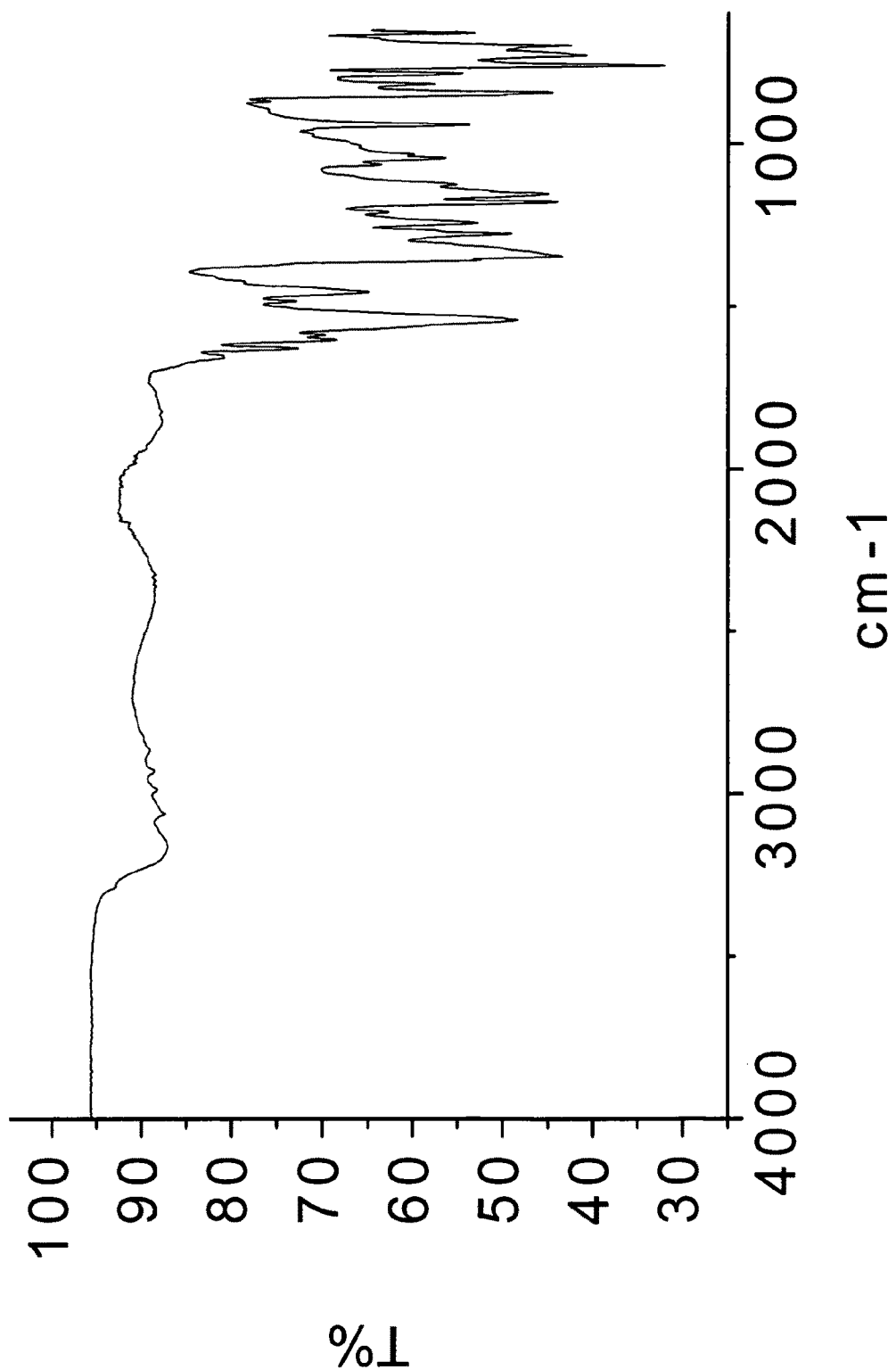

FIG. 18—FTIR spectrum of a cocrystal form I comprising meloxicam and salicylic acid (1:1).

FIG. 19—PXRD diffractogram of a cocrystal form II comprising meloxicam and salicylic acid (1:1).

Figure 20:
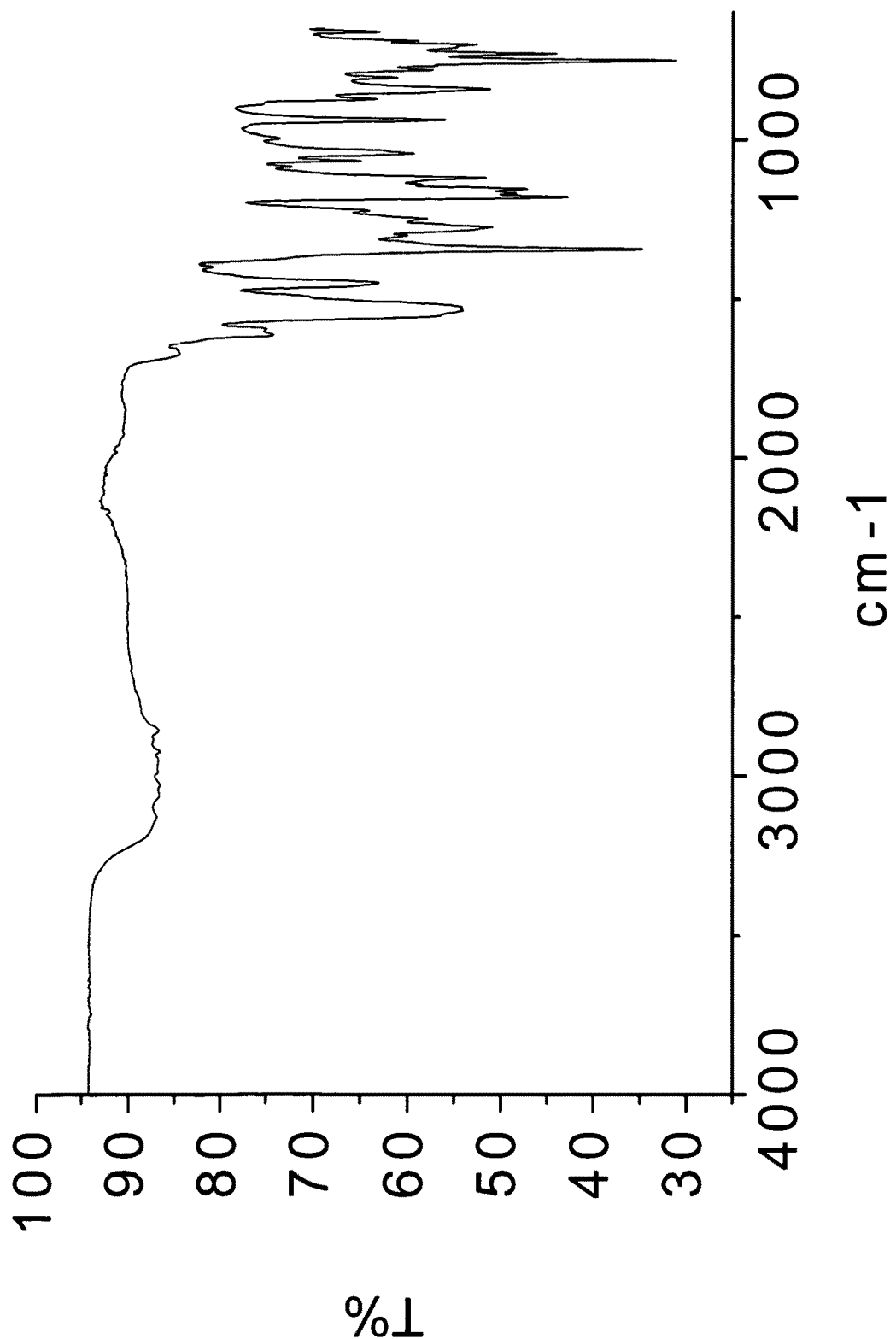

FIG. 20—FTIR spectrum of a cocrystal form II comprising meloxicam and salicylic acid (1:1).

FIG. 21—PXRD diffractogram of a cocrystal comprising meloxicam and 1-hydroxy-2-naphthoic acid (1:1).

Figure 22:
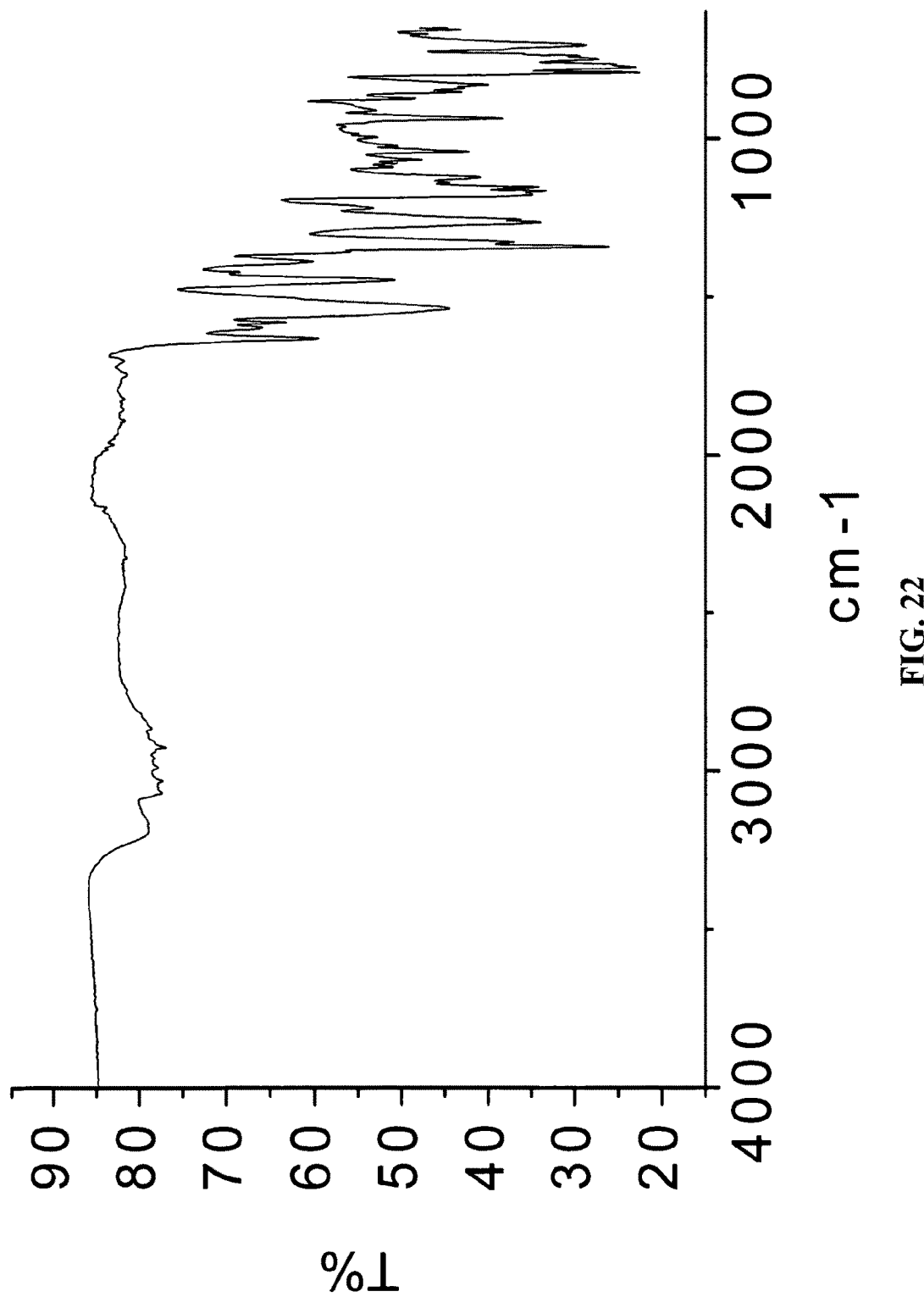

FIG. 22—FTIR spectrum of a cocrystal comprising meloxicam and 1-hydroxy-2-naphthoic acid (1:1).

FIG. 23—PXRD diffractogram of a cocrystal comprising meloxicam and maleic acid (1:1).

Figure 24:
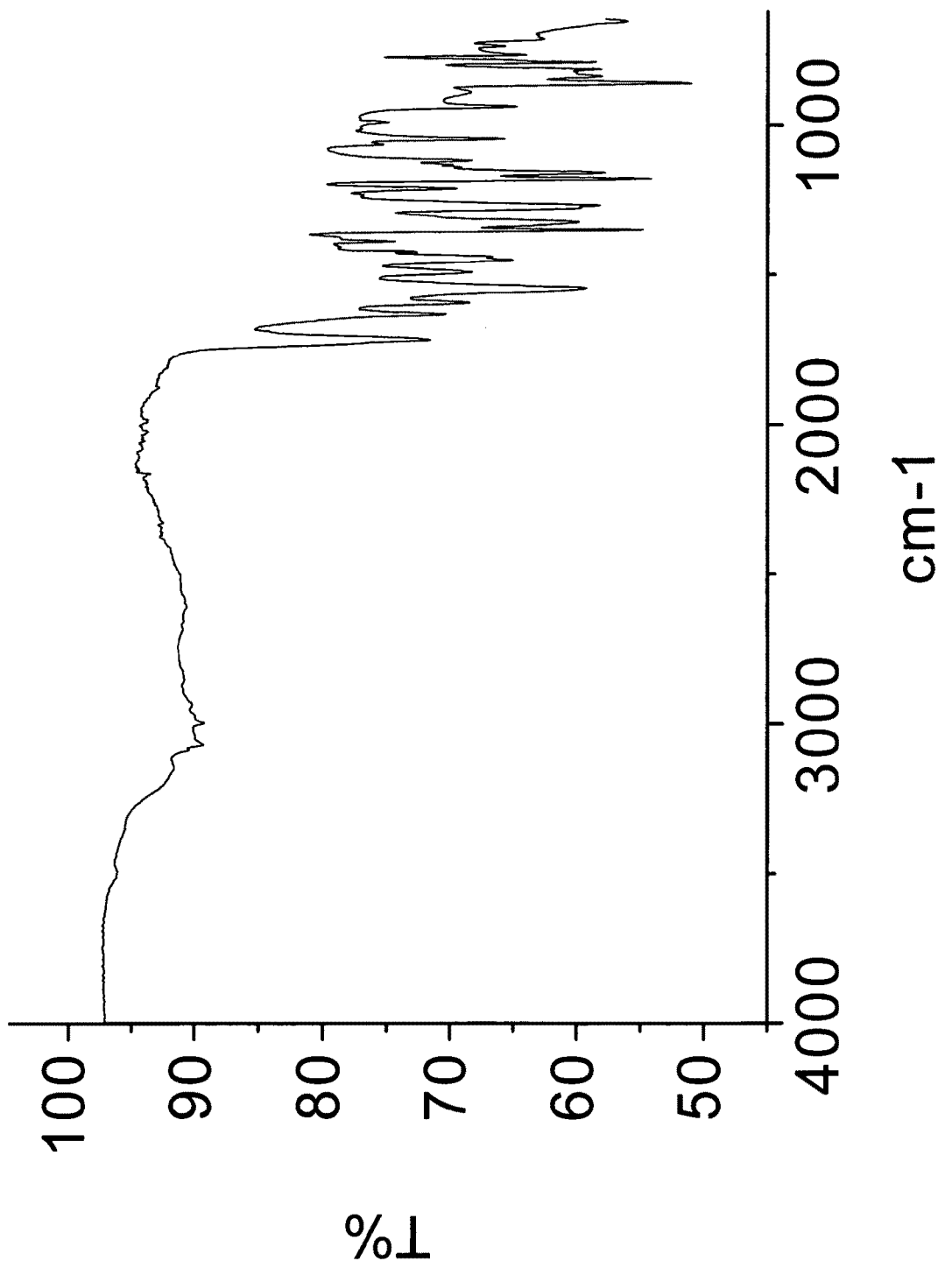

FIG. 24—FTIR spectrum of a cocrystal comprising meloxicam and maleic acid (1:1).

FIG. 25—PXRD diffractogram of a cocrystal comprising meloxicam and 4-hydroxybenzoic acid (1:1).

Figure 26:
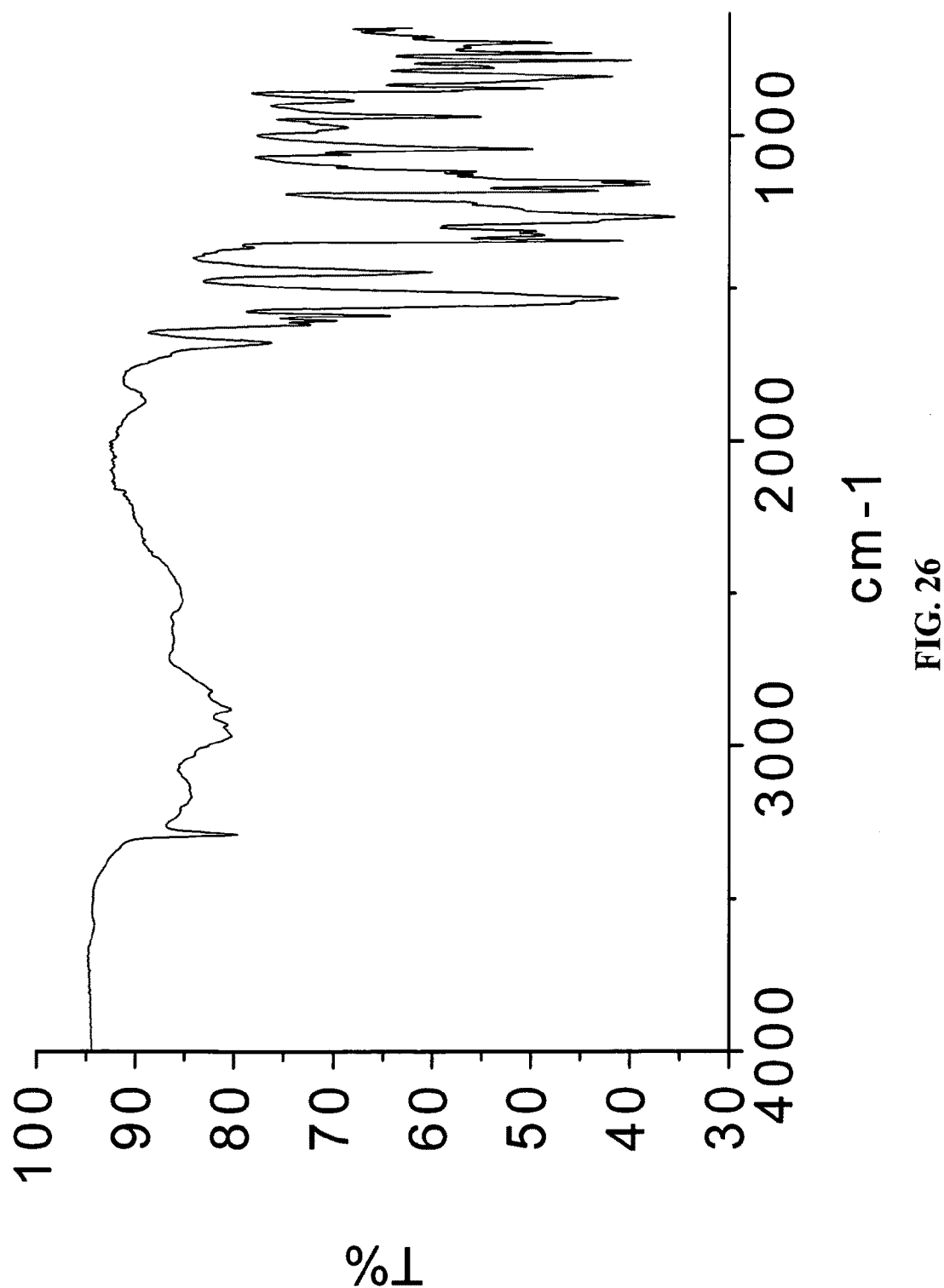

FIG. 26—FTIR spectrum of a cocrystal comprising meloxicam and 4-hydroxybenzoic acid (1:1).

FIG. 27—PXRD diffractogram of a cocrystal comprising meloxicam and malonic acid (1:1).

Figure 28:
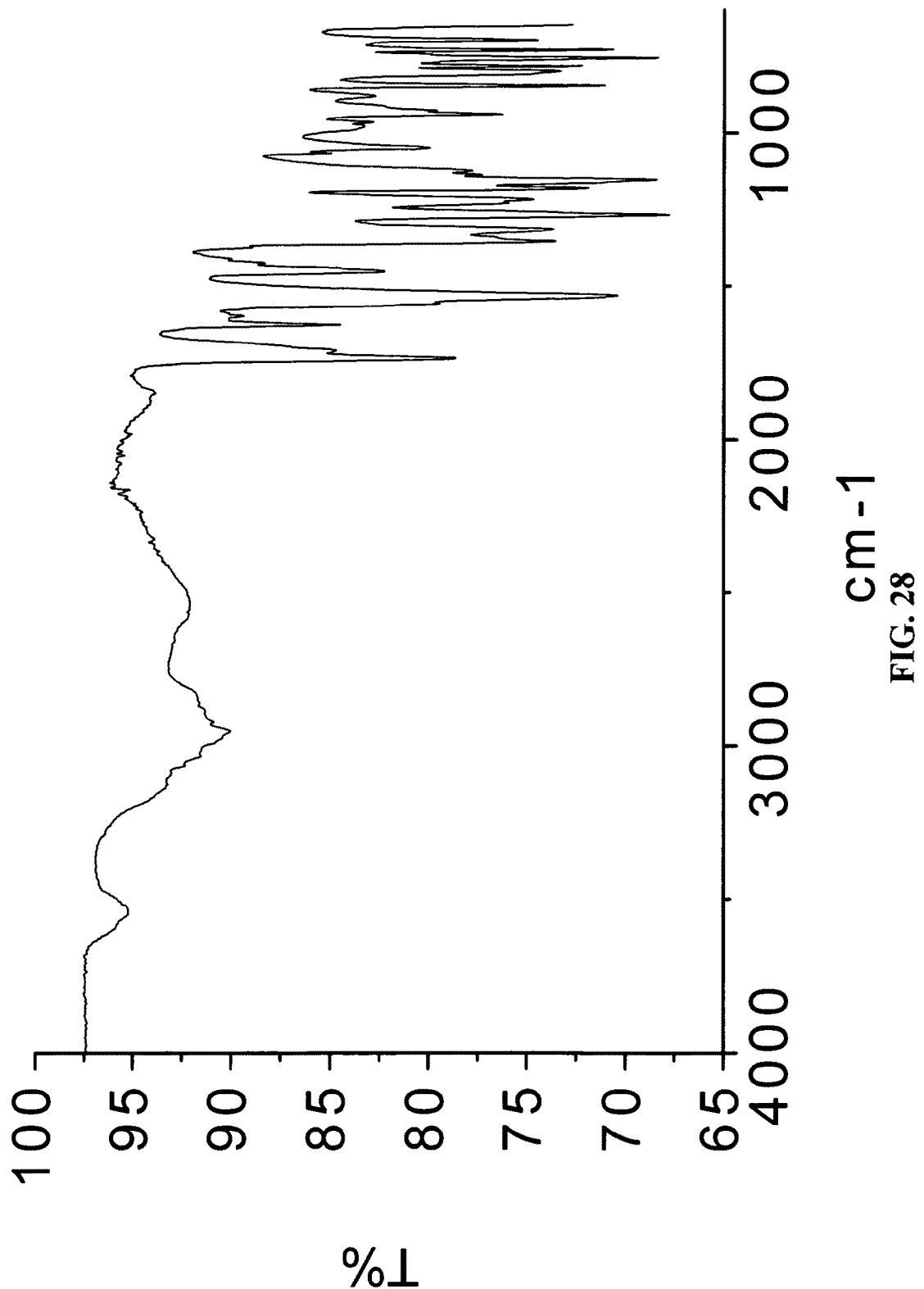

FIG. 28—FTIR spectrum of a cocrystal comprising meloxicam and malonic acid (1:1).

FIG. 29—PXRD diffractogram of a cocrystal comprising meloxicam and glycolic acid (1:1).

Figure 30:
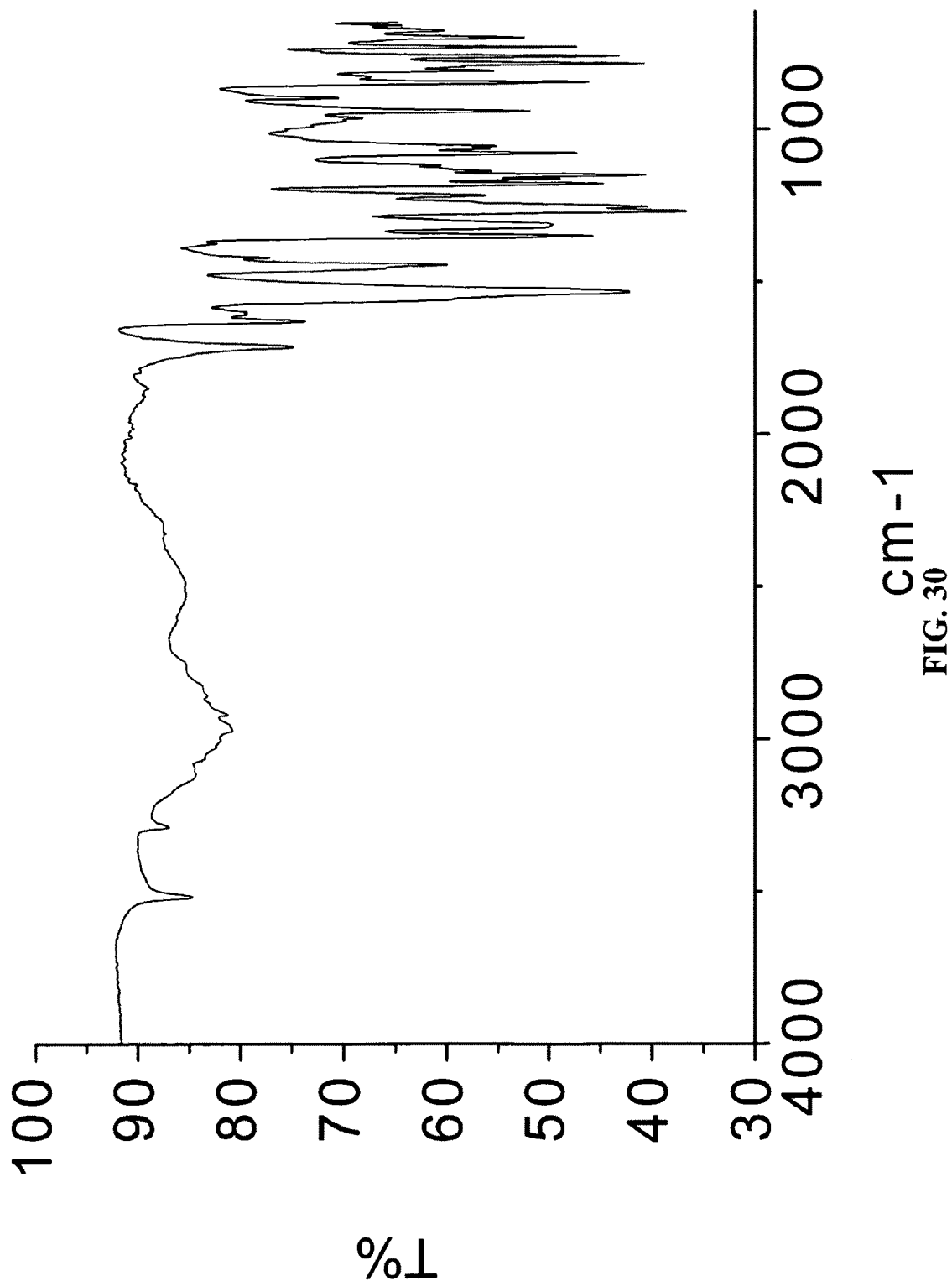

FIG. 30—FTIR spectrum of a cocrystal comprising meloxicam and glycolic acid (1:1).

FIG. 31—PXRD diffractogram of a cocrystal form I comprising meloxicam and 2,5-dihydroxybenzoic acid (1:1).

Figure 32:
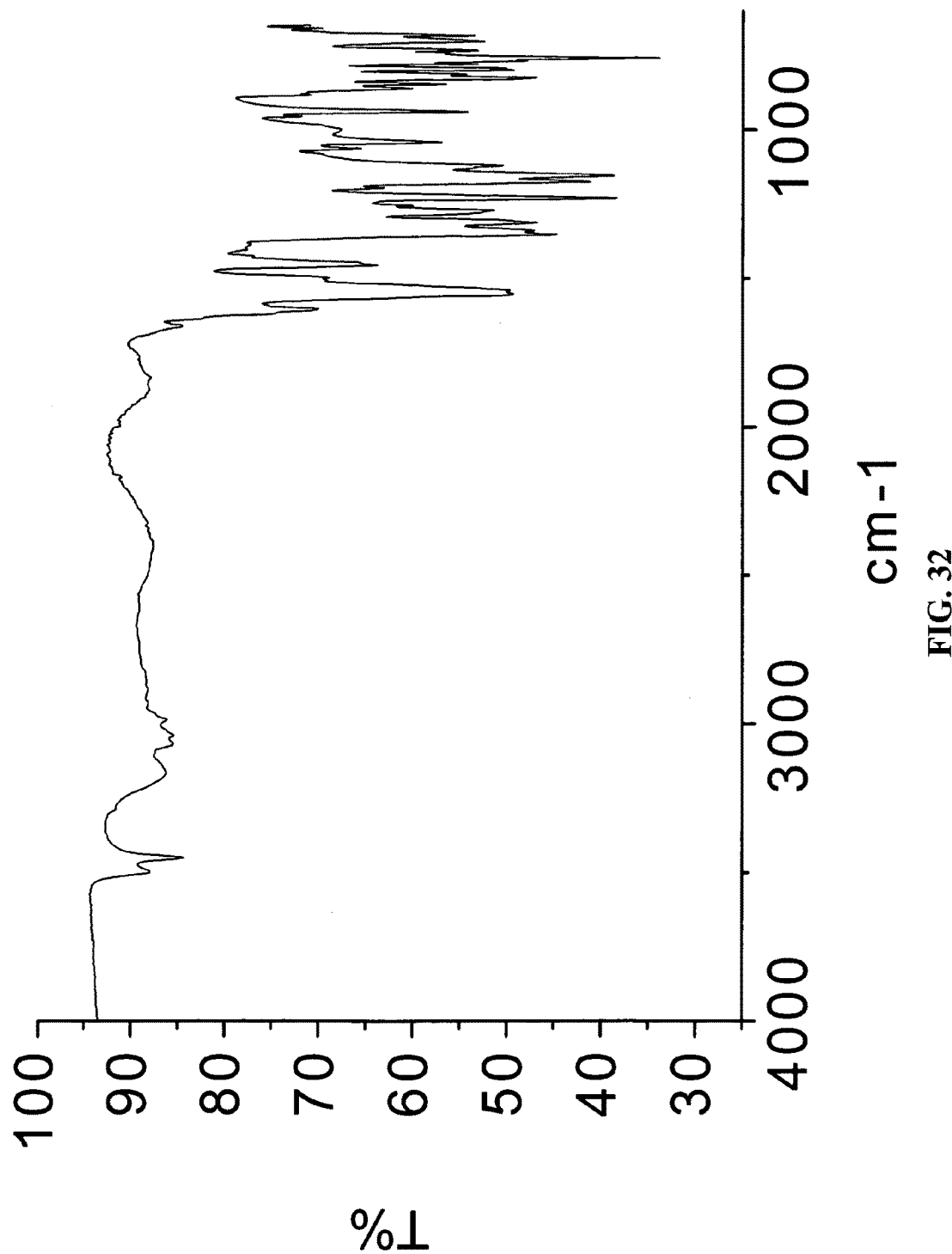

FIG. 32—FTIR spectrum of a cocrystal form I comprising meloxicam and 2,5-dihydroxybenzoic:acid (1:1).

FIG. 33—PXRD diffractogram of a cocrystal form II comprising meloxicam and 2,5-dihydroxybenzoic acid (1:1).

Figure 34:
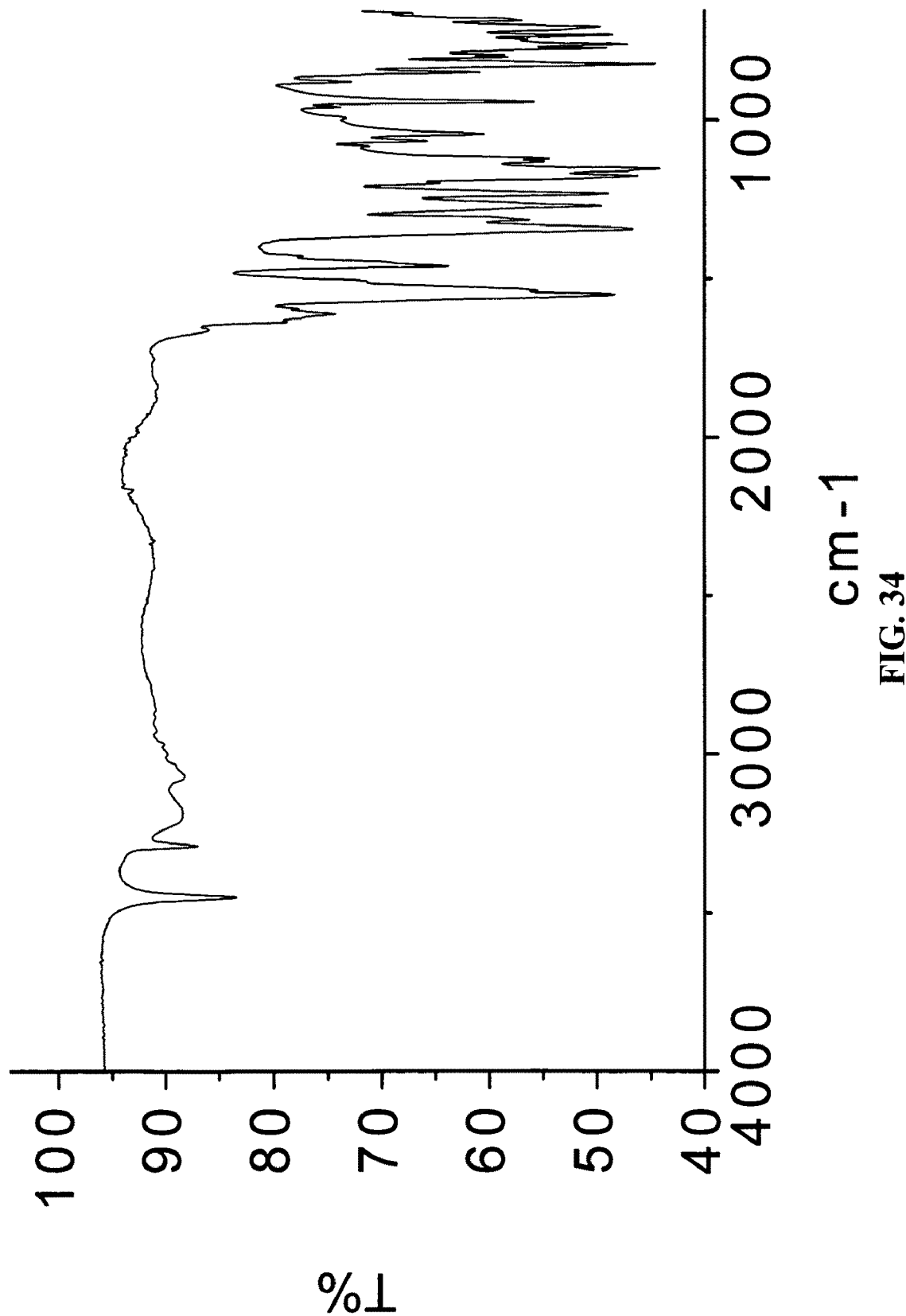

FIG. 34—FTIR spectrum of a cocrystal form II comprising meloxicam and 2,5-dihydroxybenzoic acid (1:1).

FIG. 35—PXRD diffractogram of a cocrystal form I comprising meloxicam and (+) camphoric acid, (3:2).

Figure 36:
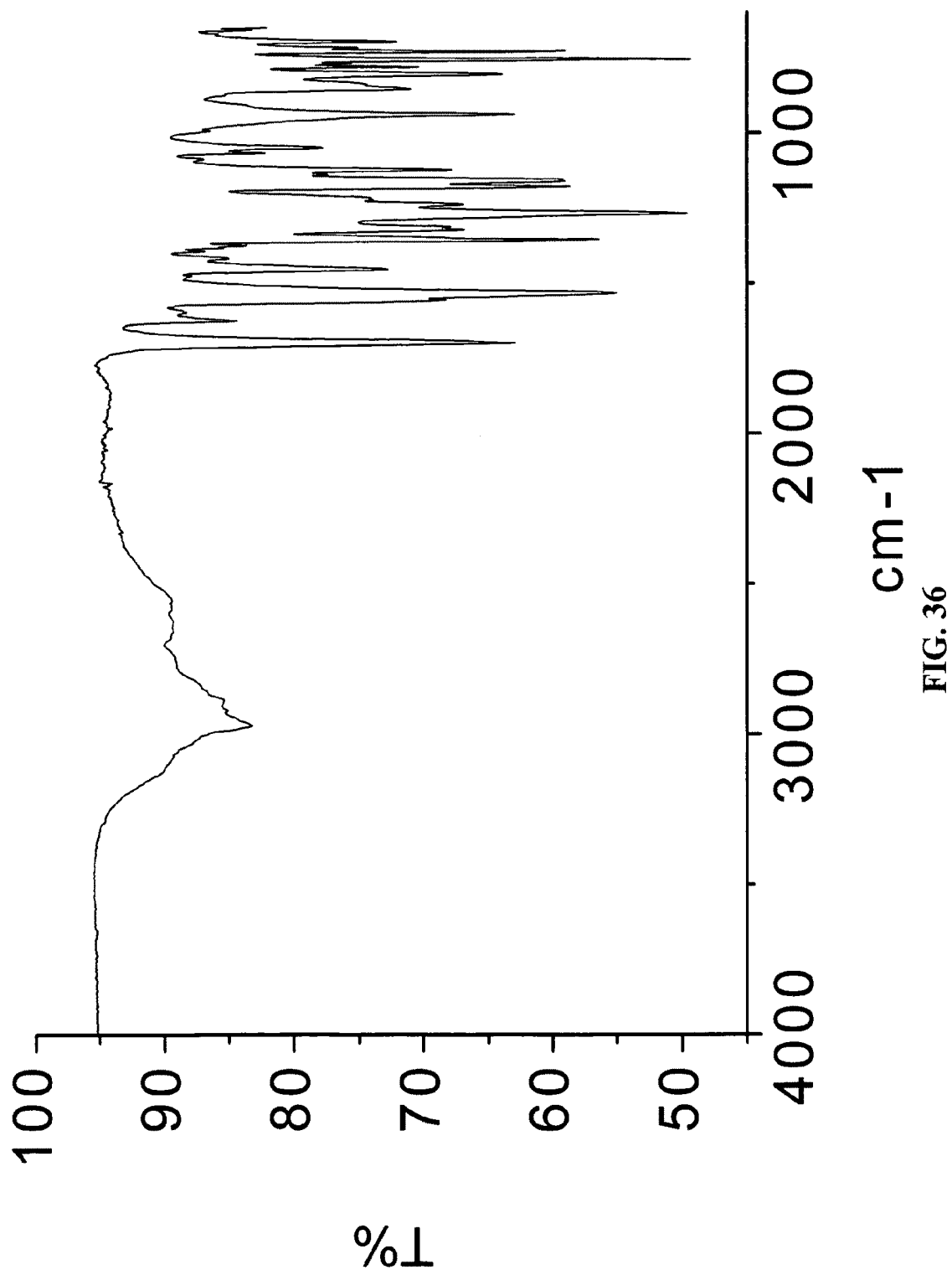

FIG. 36—FTIR spectrum of a cocrystal form I comprising meloxicam and (+) camphoric acid (3:2).

FIG. 37—PXRD diffractogram of a cocrystal form II comprising meloxicam and (+) camphoric acid (3:2).

Figure 38:
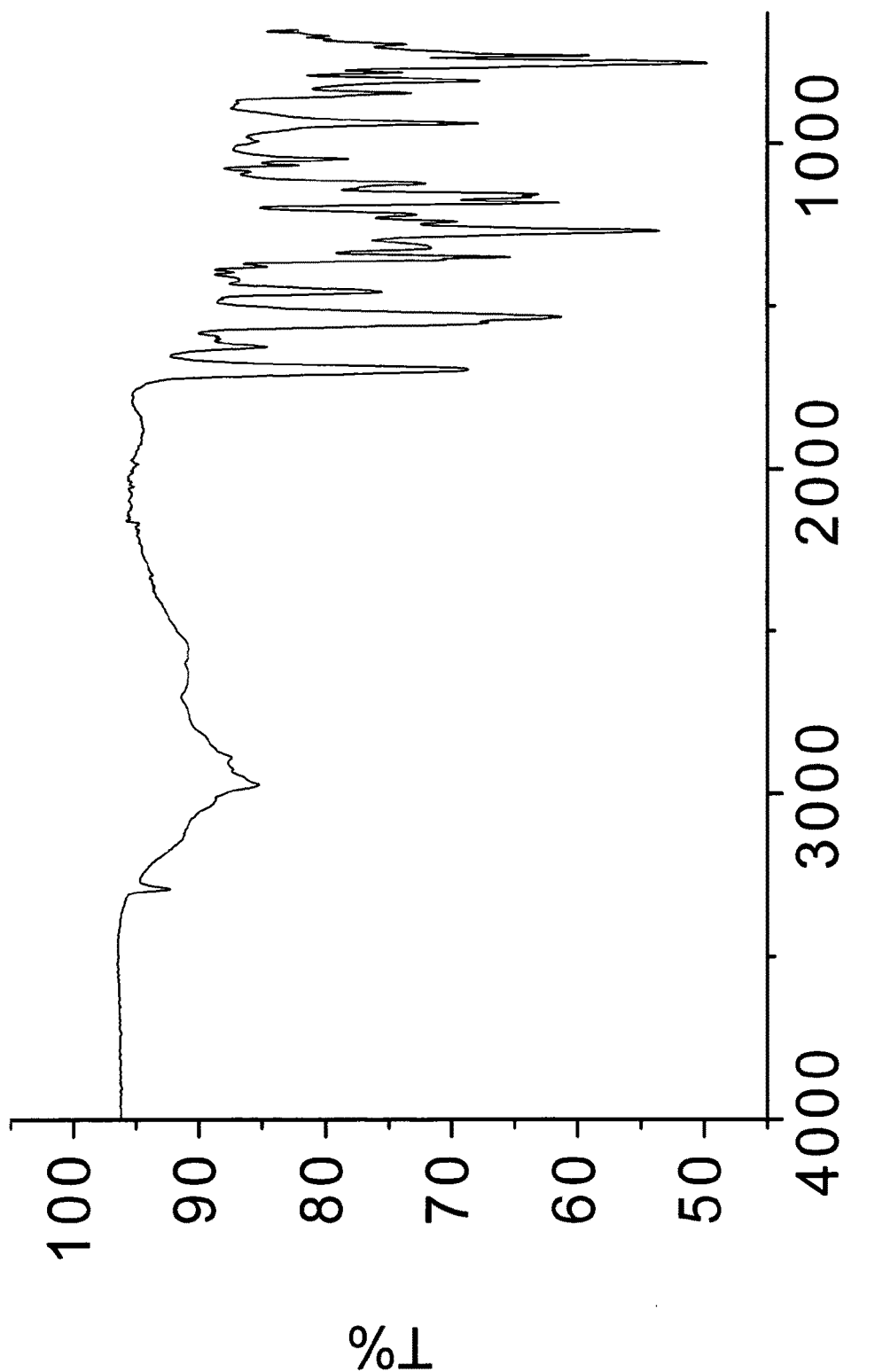

FIG. 38—FTIR spectrum of a cocrystal form II comprising meloxicam and (+) camphoric acid (3:2).

FIG. 39. PXRD diffractogram of a cocrystal comprising meloxicam and maltol (1:1).

Figure 40:
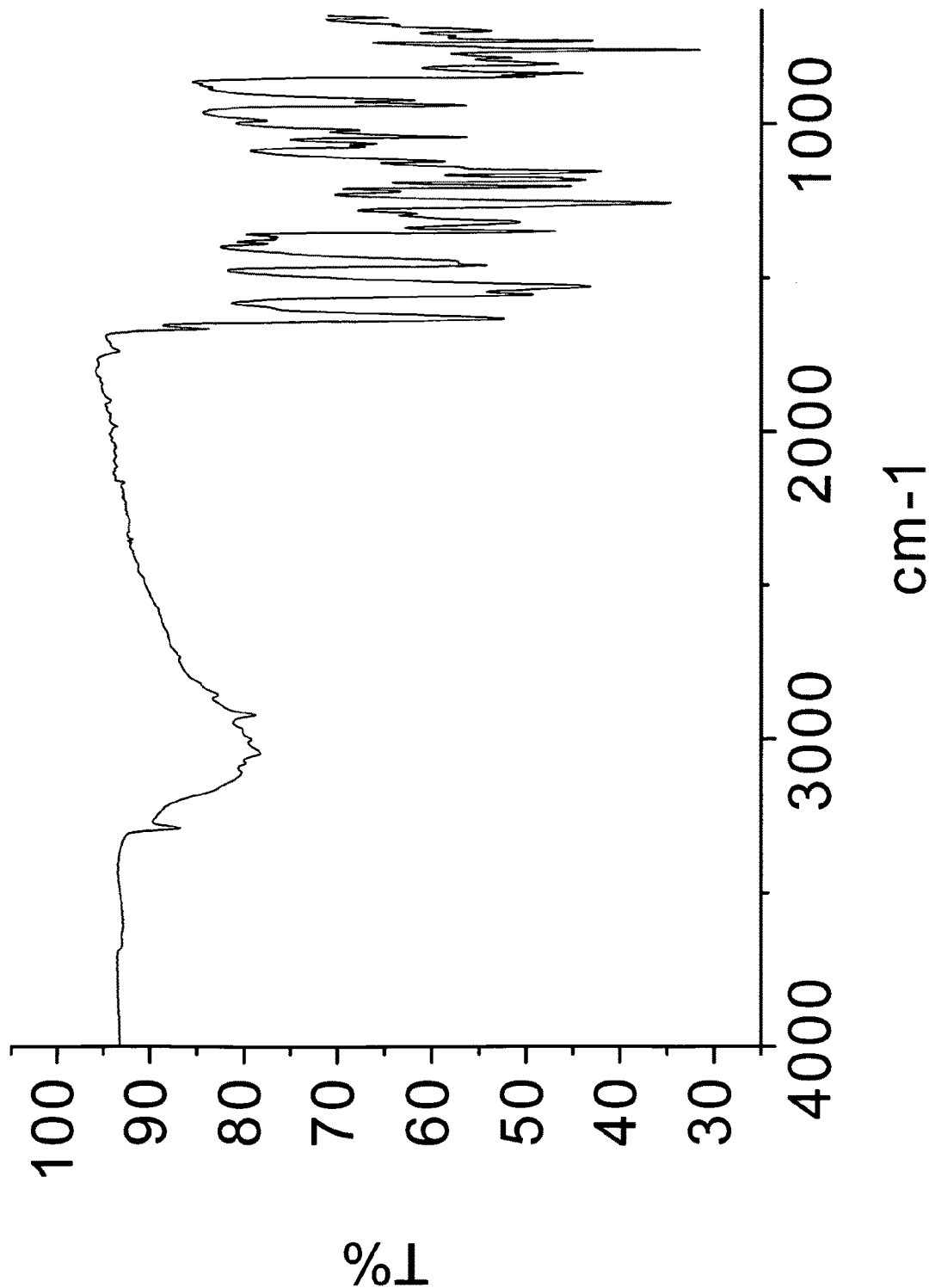

FIG. 40. FTIR spectrum of a cocrystal comprising meloxicam and maltol (1:1).

FIG. 41. PXRD diffractogram of a cocrystal form III comprising meloxicam and salicylic acid (1:1).

Figure 42:
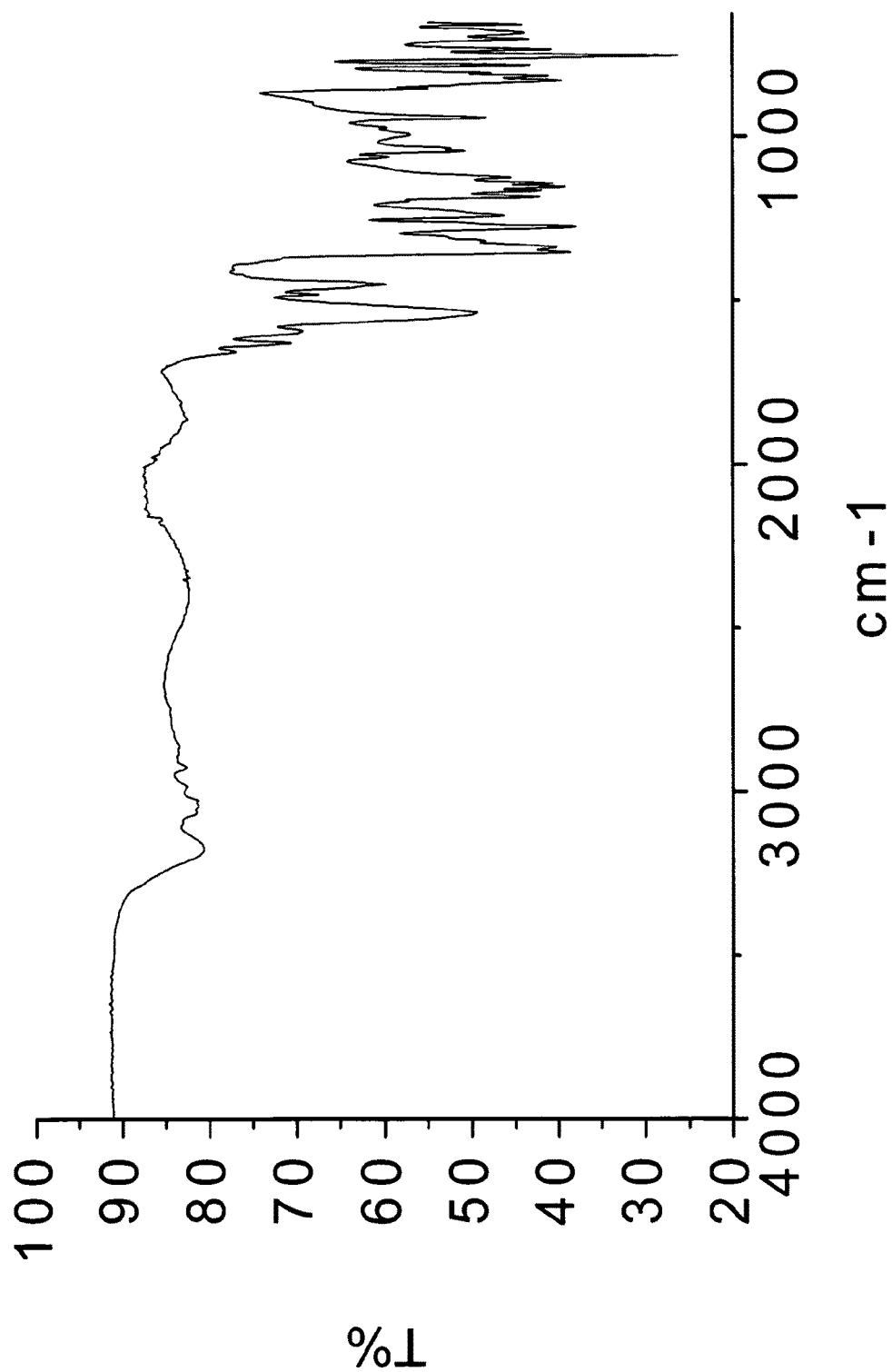

FIG. 42. FTIR spectrum of a cocrystal form III comprising meloxicam and salicylic acid (1:1).

FIG. 43. PXRD diffractogram of a cocrystal comprising meloxicam and ethyl maltol (1:1).

Figure 44:
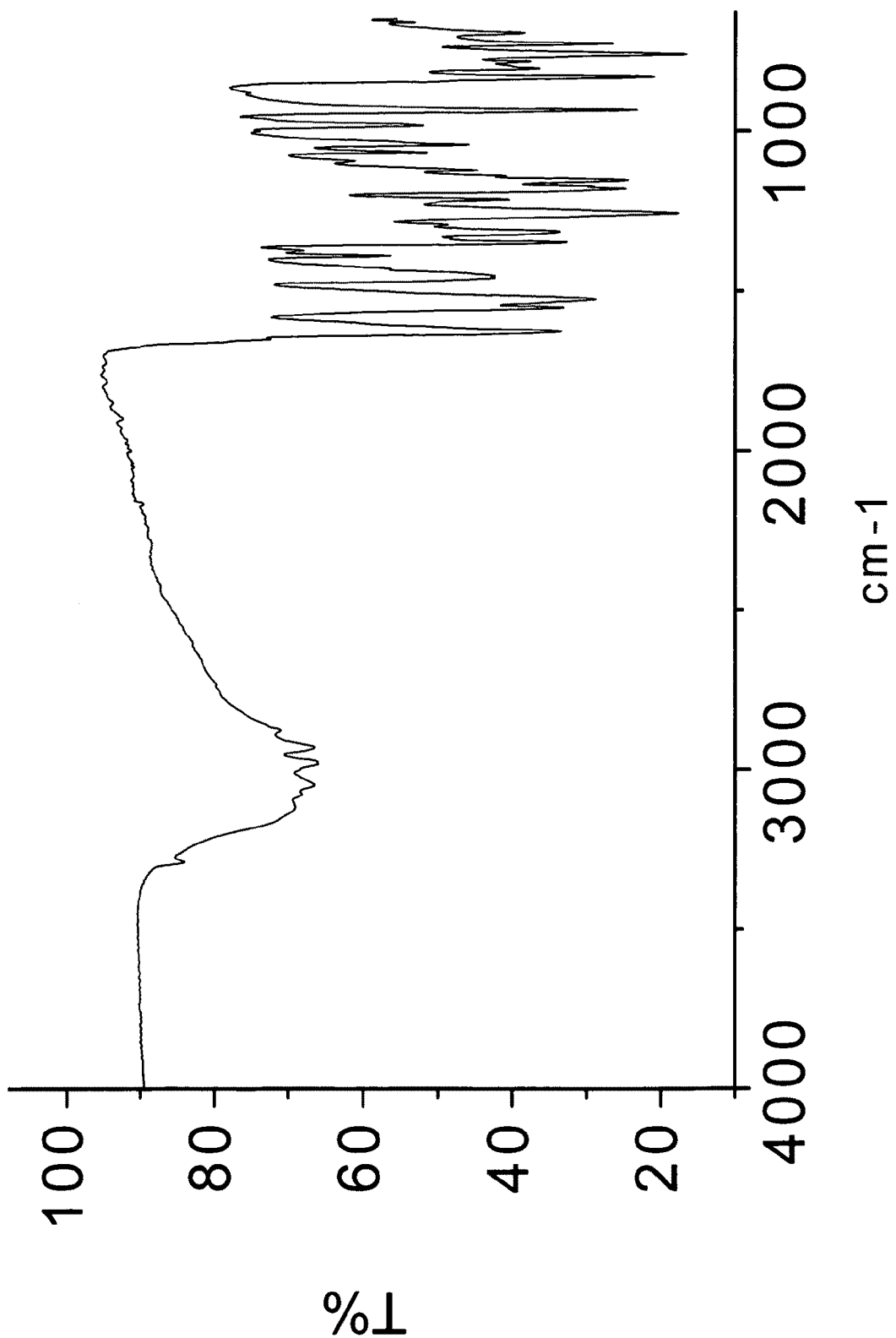

FIG. 44. FTIR spectrum of a cocrystal comprising meloxicam and ethyl maltol (1:1).

FIG. 45. PXRD diffractogram of a cocrystal comprising meloxicam and hydrocinnamic acid (1:1).

Figure 46:
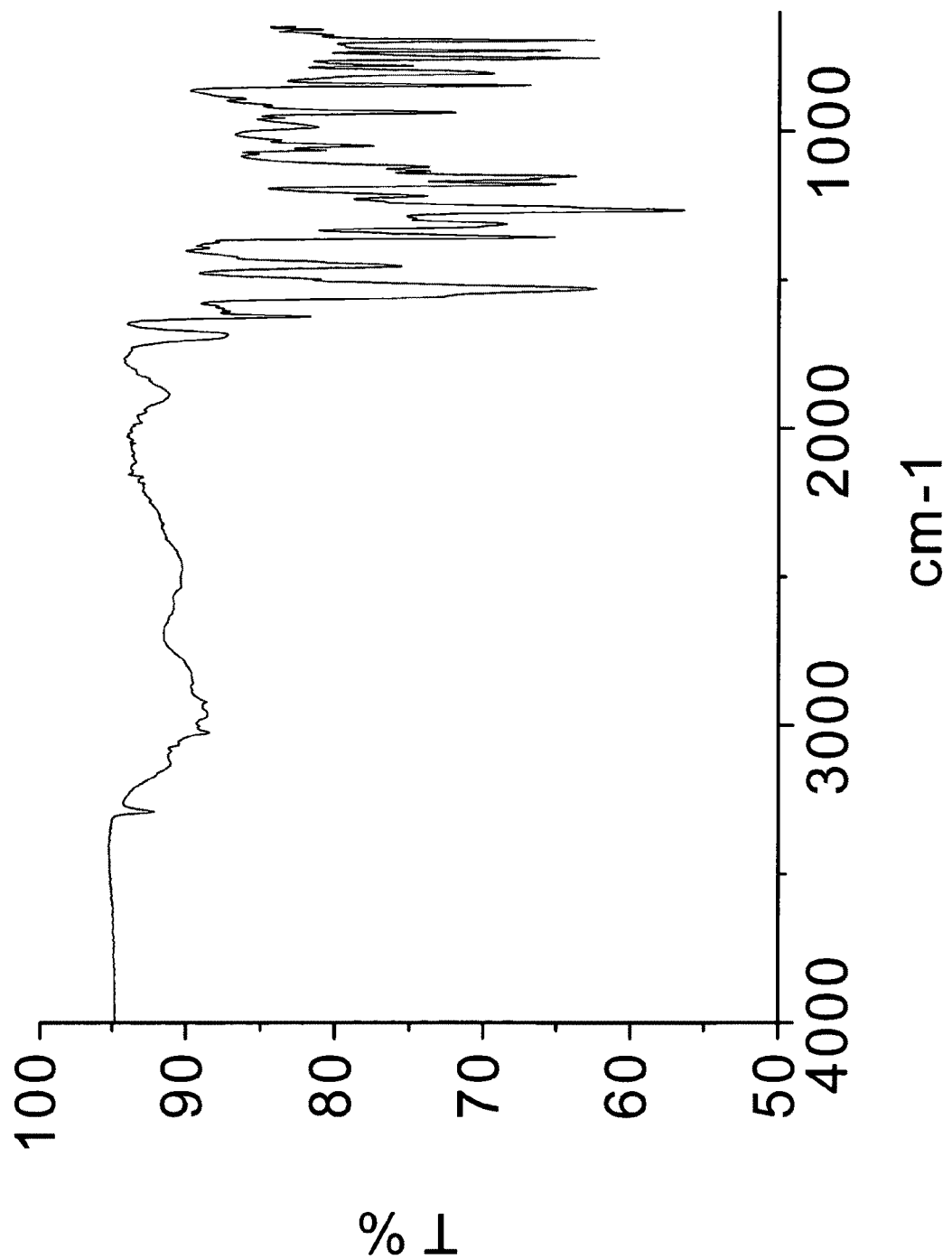

FIG. 46. FTIR spectrum of a cocrystal comprising meloxicam and hydrocinnamic acid (1:1).

Figure 47:
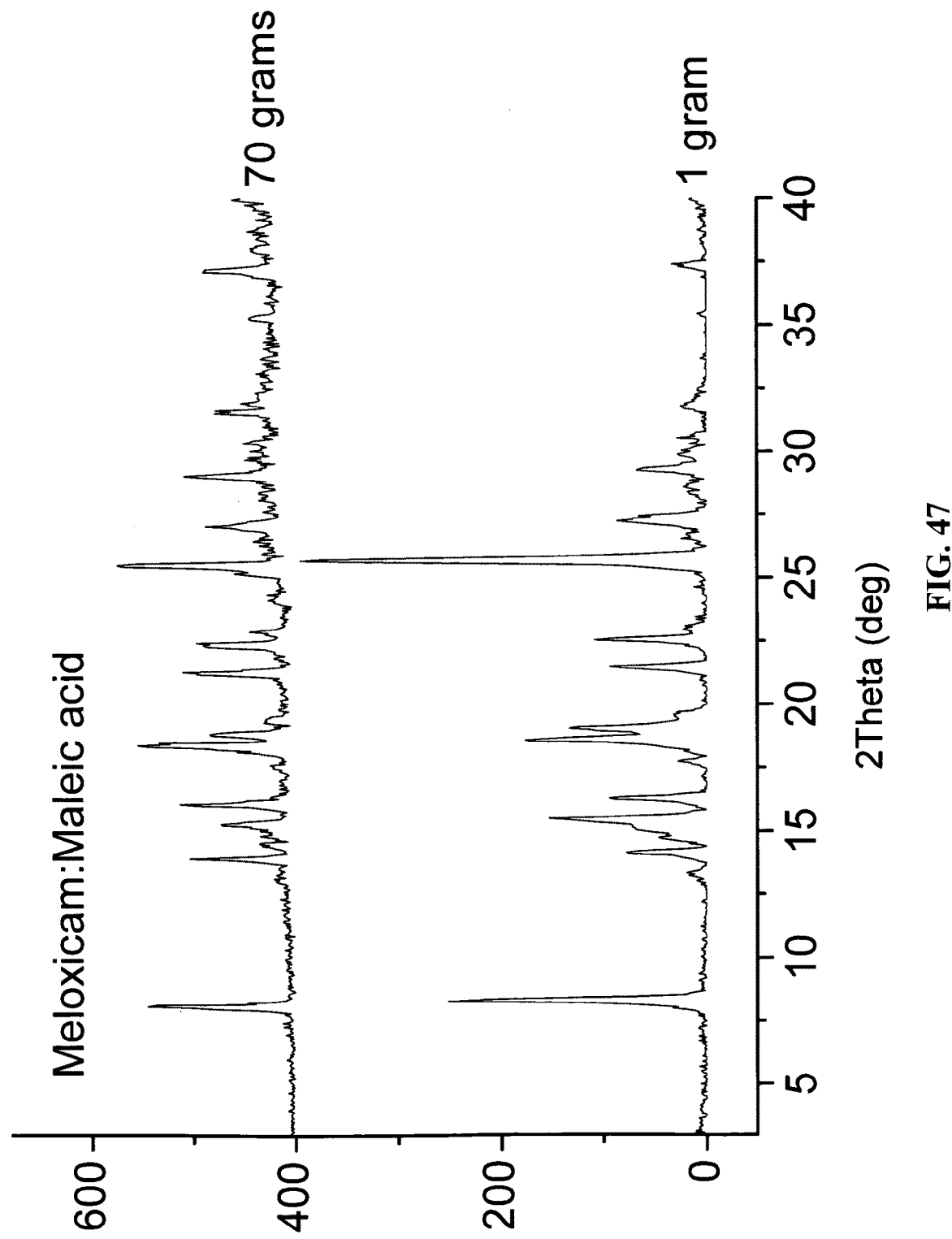

FIG. 47. PXRD diffractograms of two different scale (1 g and 70 g) batches of cocrystals of meloxicam and maleic acid (1:1).

Figure 48:
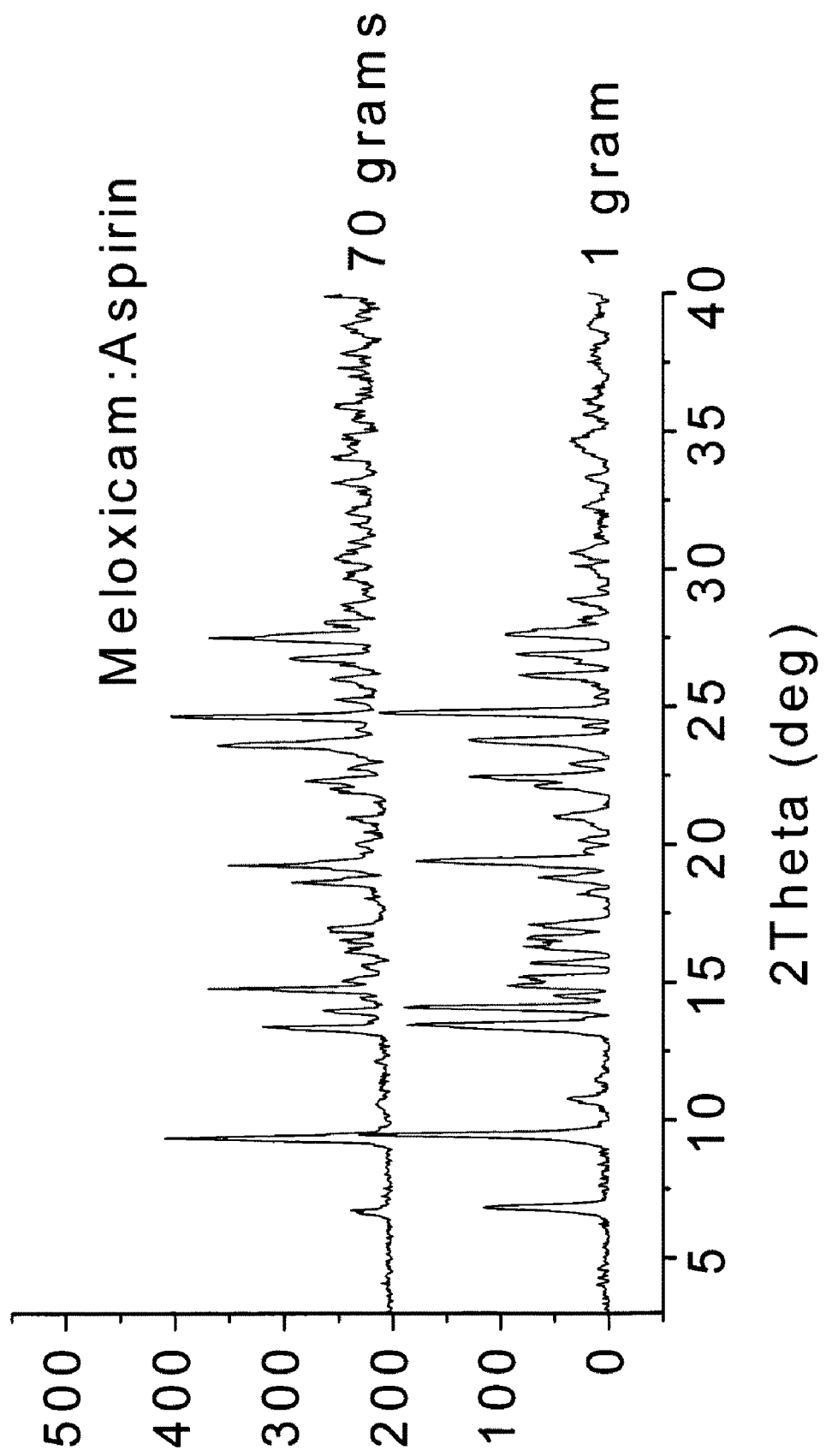

FIG. 48. PXRD diffractograms of two different scale (1 g and 70 g) batches of cocrystals of meloxicam and aspirin (1:1).

Figure 49:
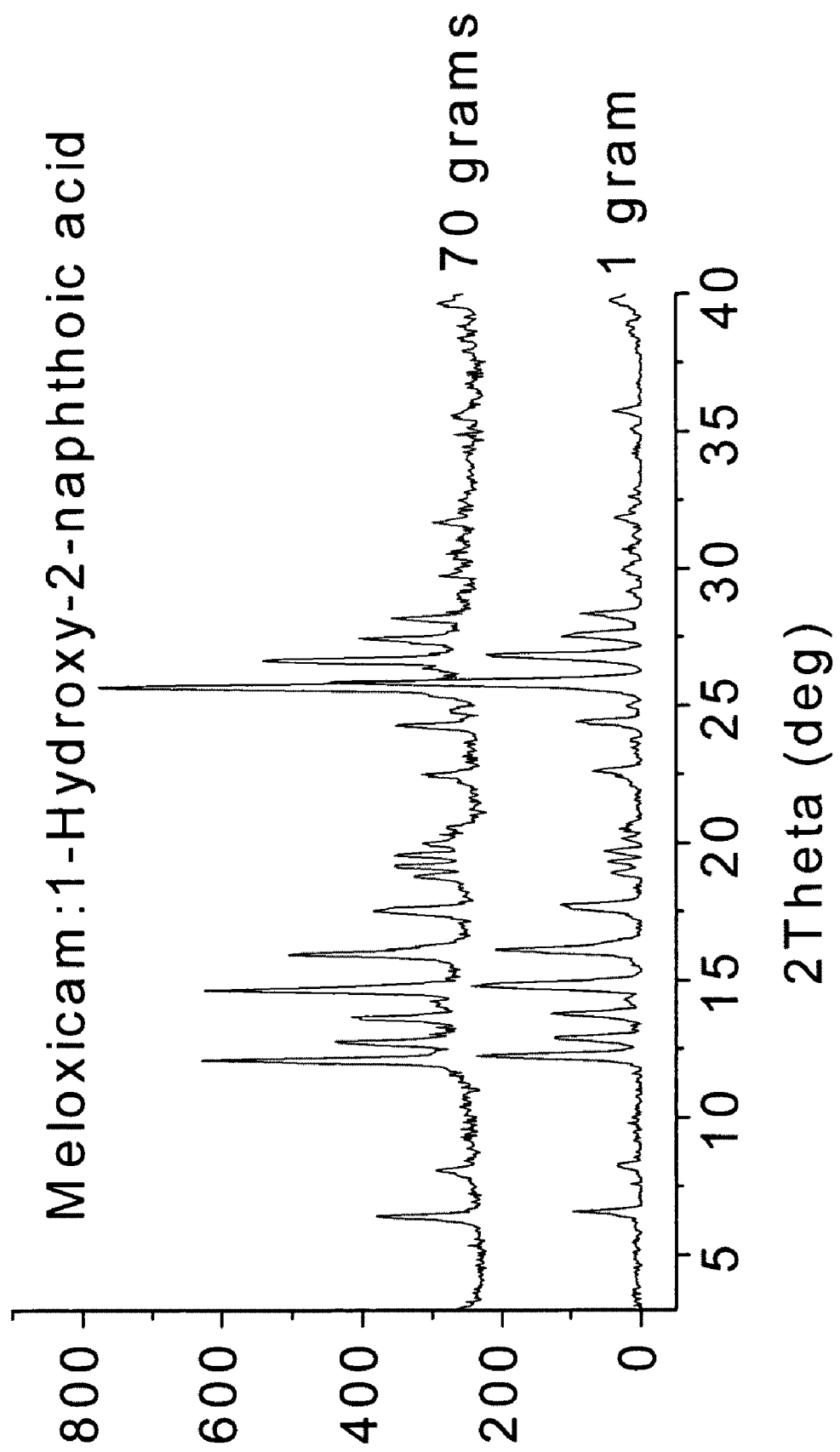

FIG. 49. PXRD diffractograms of two different scale (1 g and 70 g) batches of cocrystals of meloxicam and 1-hydroxy-2-naphthoic acid (1:1).

Figure 50:
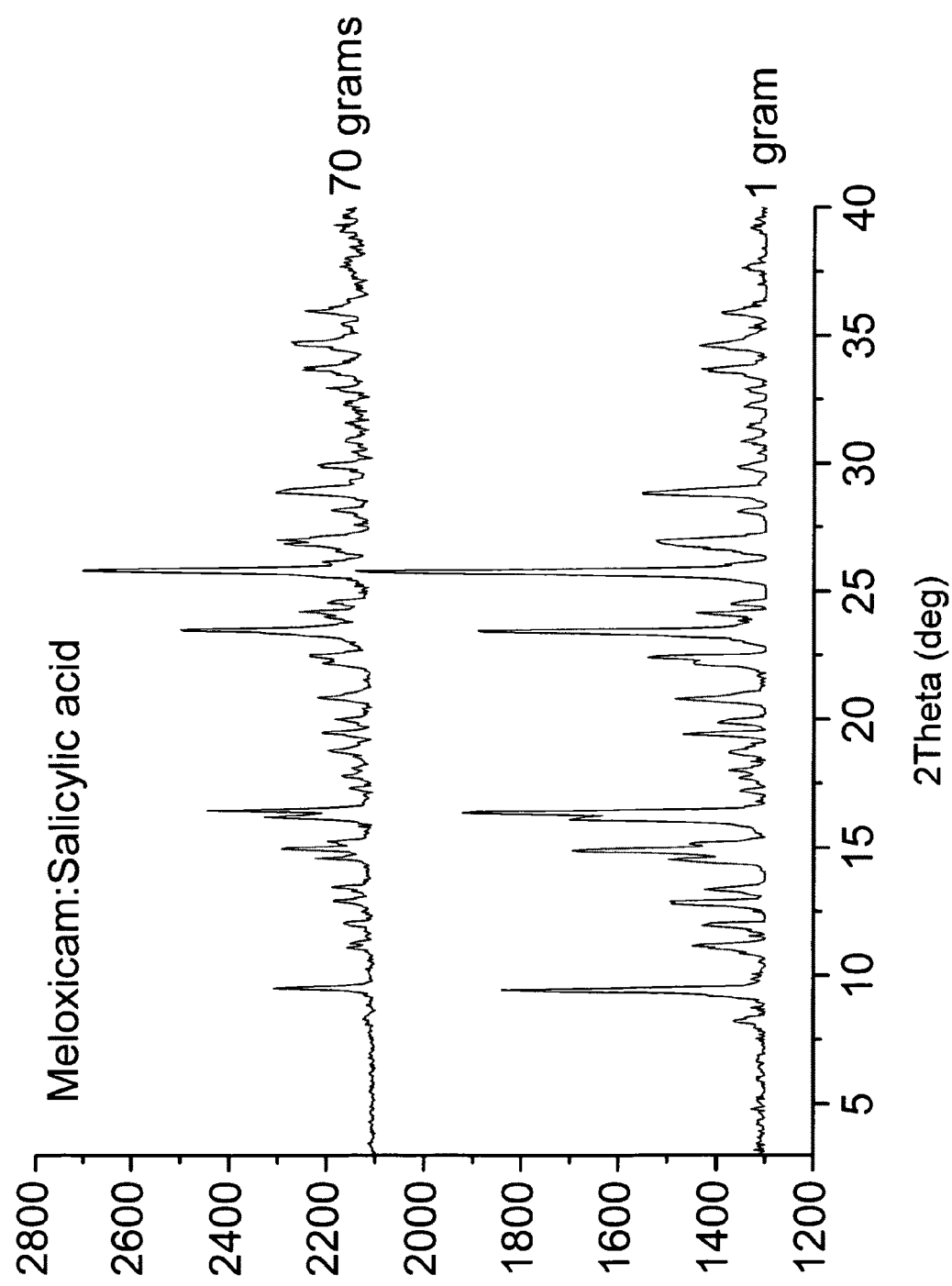

FIG. 50. PXRD diffractograms of two different scale (1 g and 70 g) batches of cocrystals of meloxicam and salicylic acid, form III (1:1).

Figure 51:
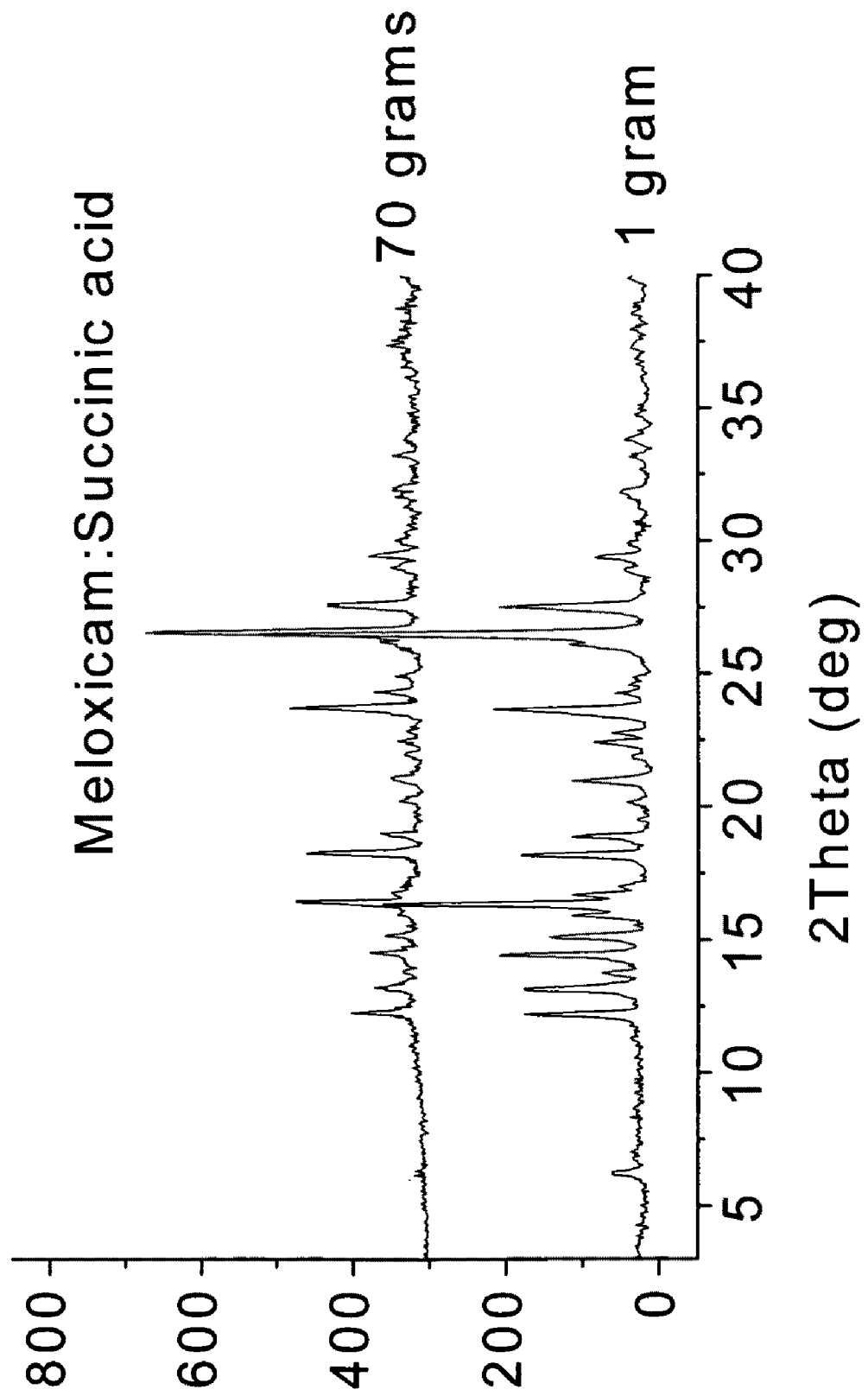

FIG. 51. PXRD diffractograms of two different scale (1 g and 70 g) batches of cocrystals of meloxicam and succinic acid (2:1).

Figure 52:
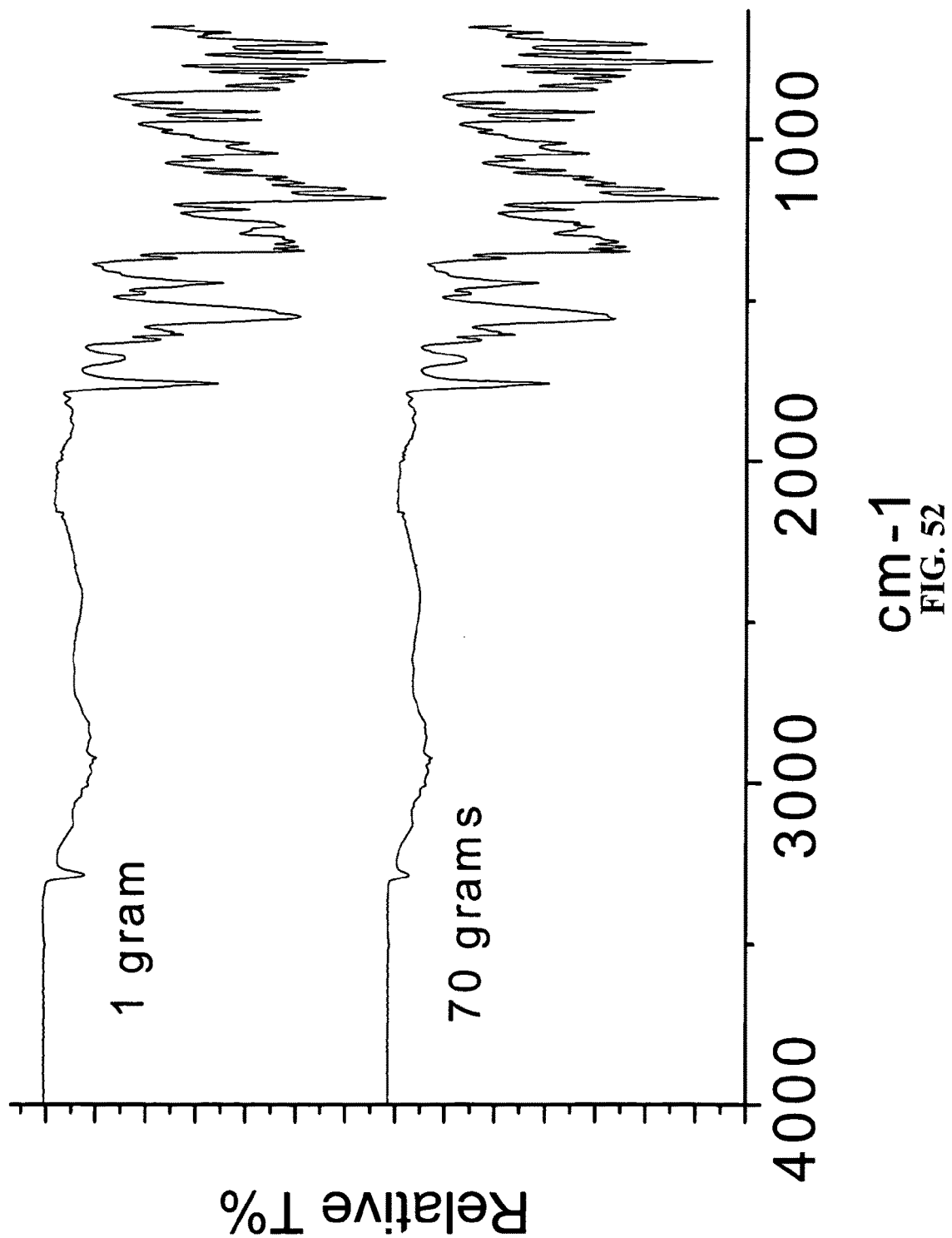

FIG. 52. FTIR spectra of two different scale (1 g and 70 g) batches of cocrystals of meloxicam and aspirin (acetylsalicylic acid) (1:1).

Figure 53:
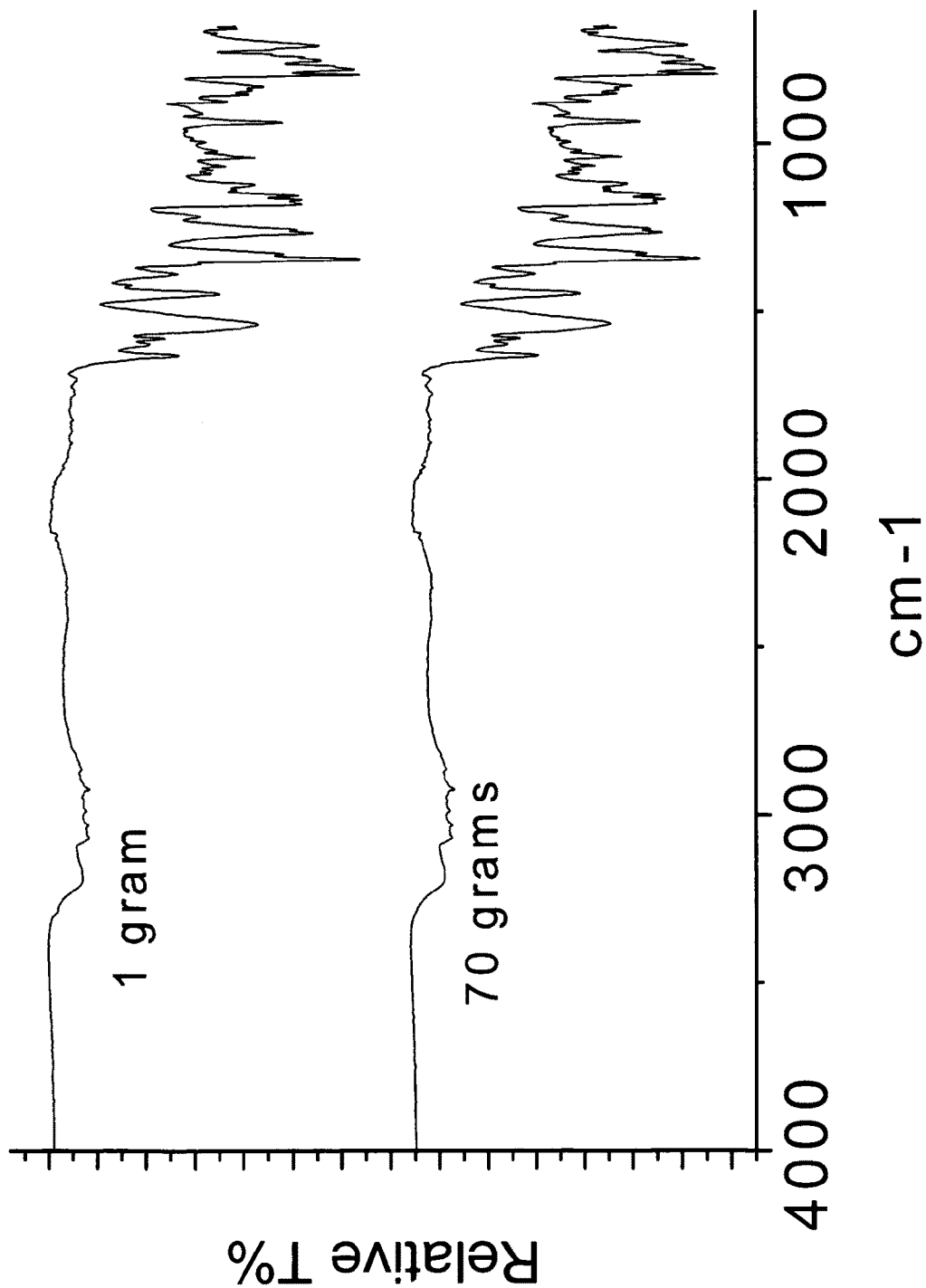

FIG. 53. FTIR spectra of two different scale (1 g and 70 g) batches of cocrystals of meloxicam and 1-hydroxy-2-naphthoic acid (1:1).

Figure 54:
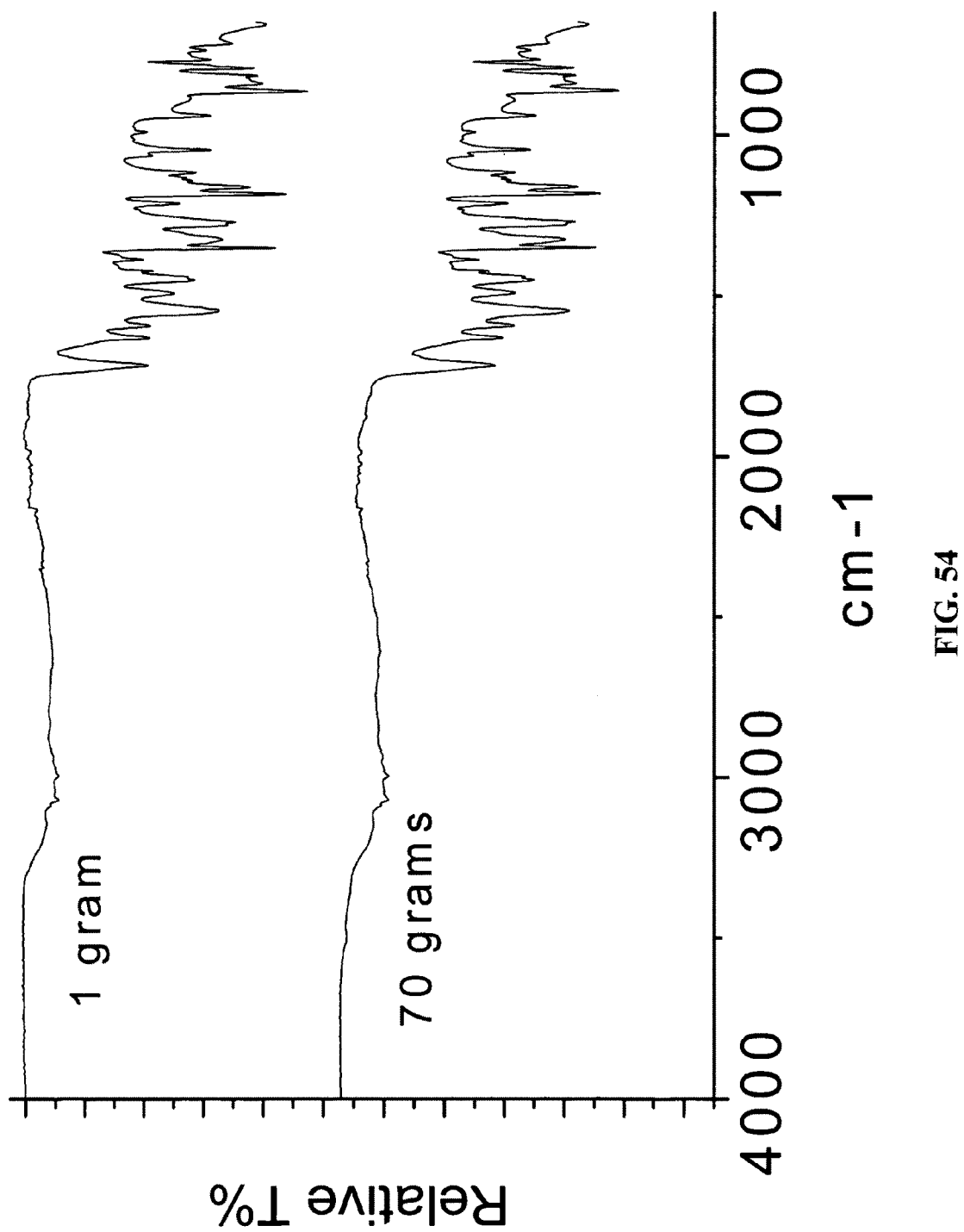

FIG. 54. FTIR spectra of two different scale (1 g and 70 g) batches of cocrystals of meloxicam and maleic acid (1:1).

Figure 55:
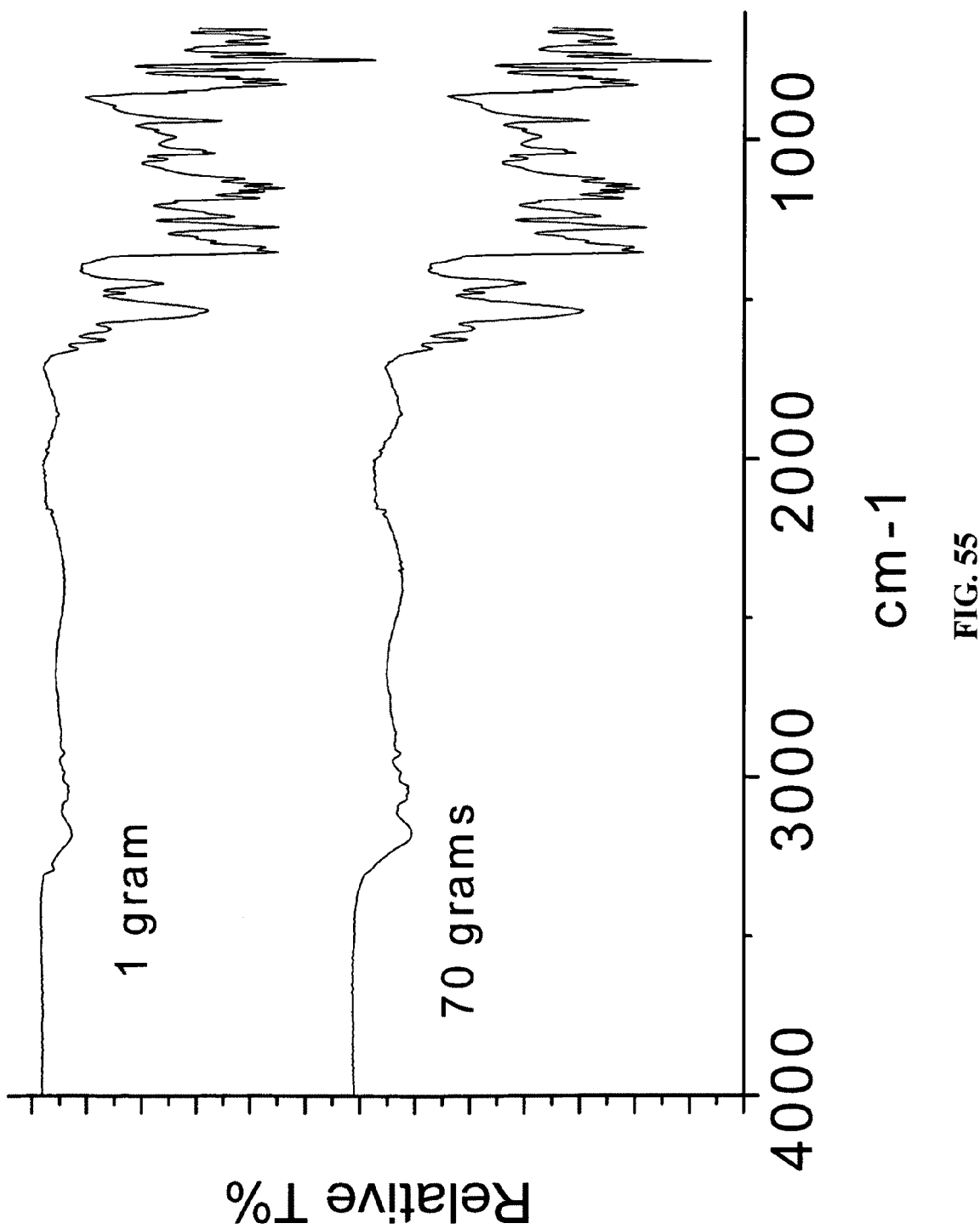

FIG. 55. FTIR spectra of two different scale (1 g and 70 g) batches of cocrystals of meloxicam and salicylic acid, form III (1:1).

Figure 56:
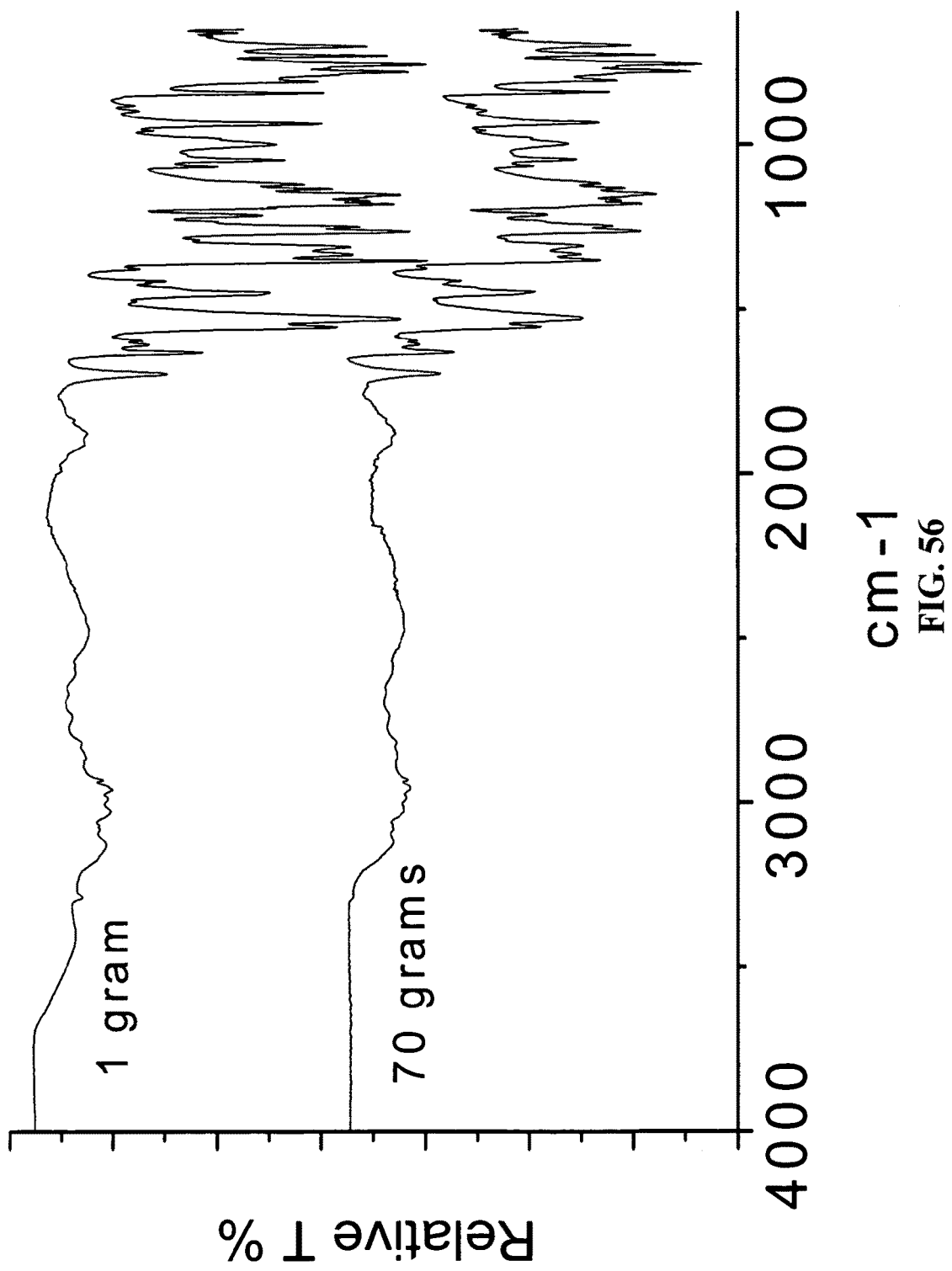

FIG. 56. FTIR spectra of two different scale (1 g and 70 g) batches of cocrystals of meloxicam and succinic acid (2:1).

Figure 57:
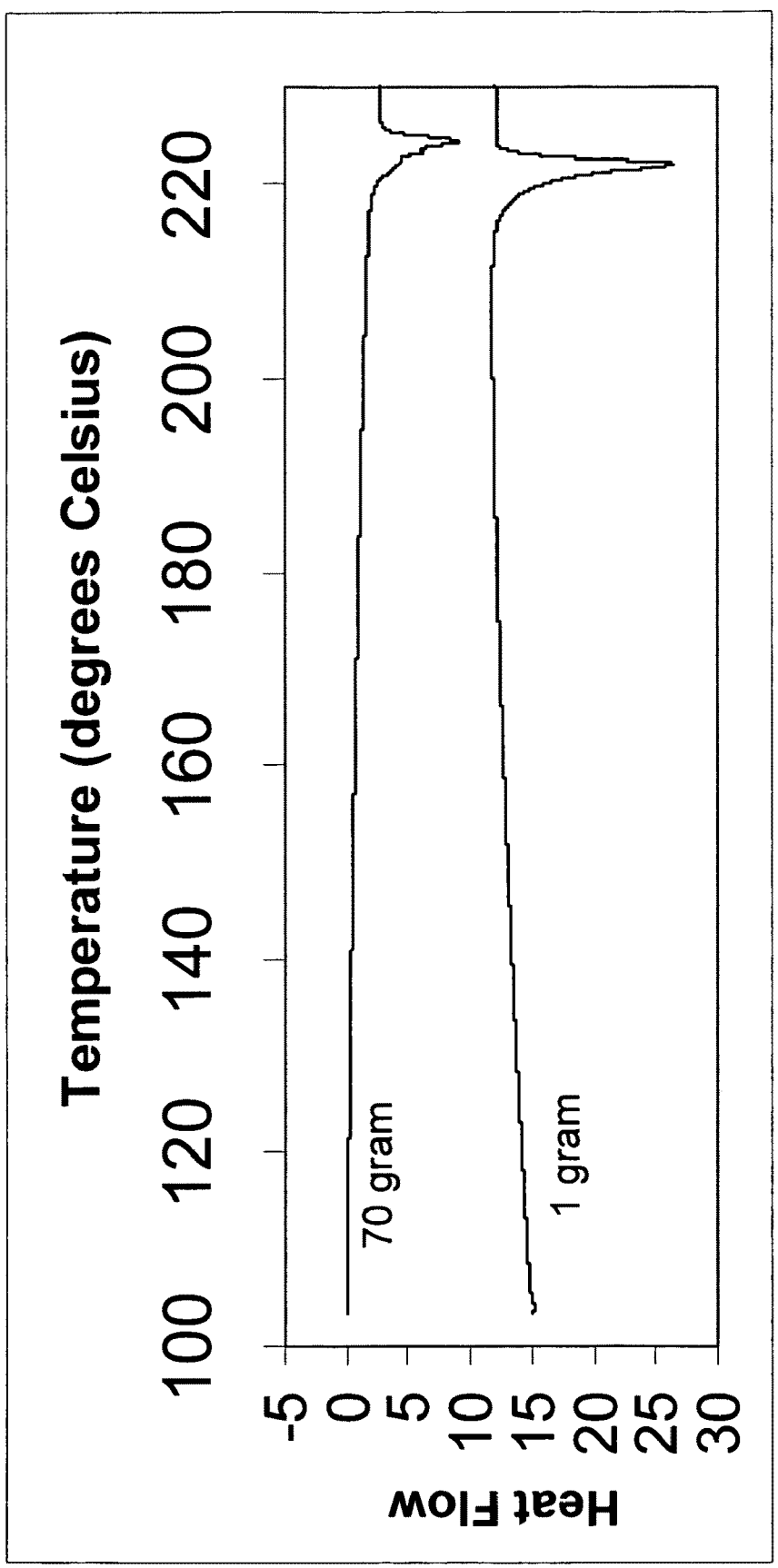

FIG. 57. DSC scans of two different scale (1 g and 70 g) batches of cocrystals of meloxicam and 1-hydroxy-2-naphthoic acid (1:1).

Figure 58:
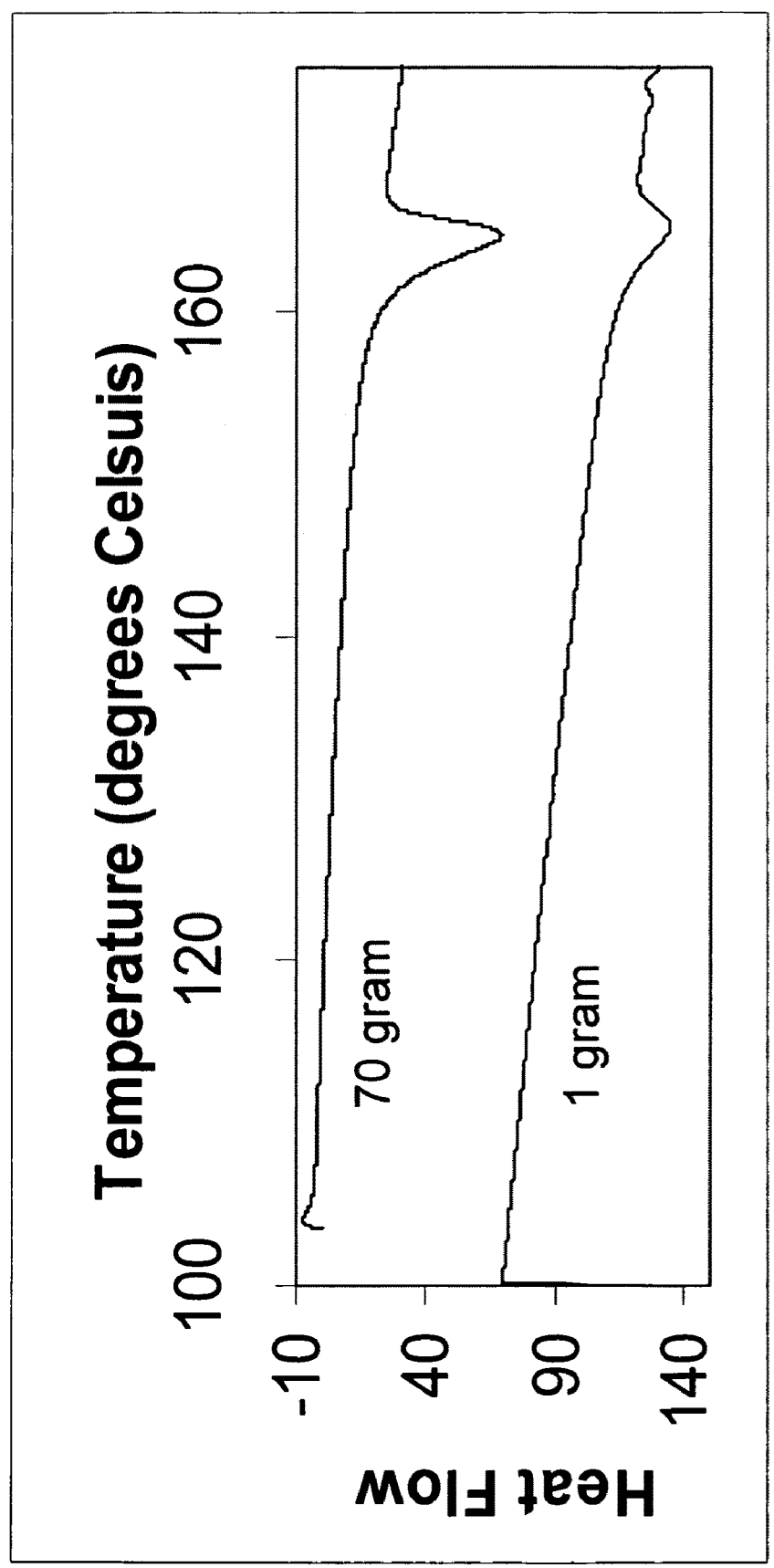

FIG. 58. DSC scans of two different scale (1 g and 70 g) batches of cocrystals of meloxicam and aspirin (1:1).

Figure 59:
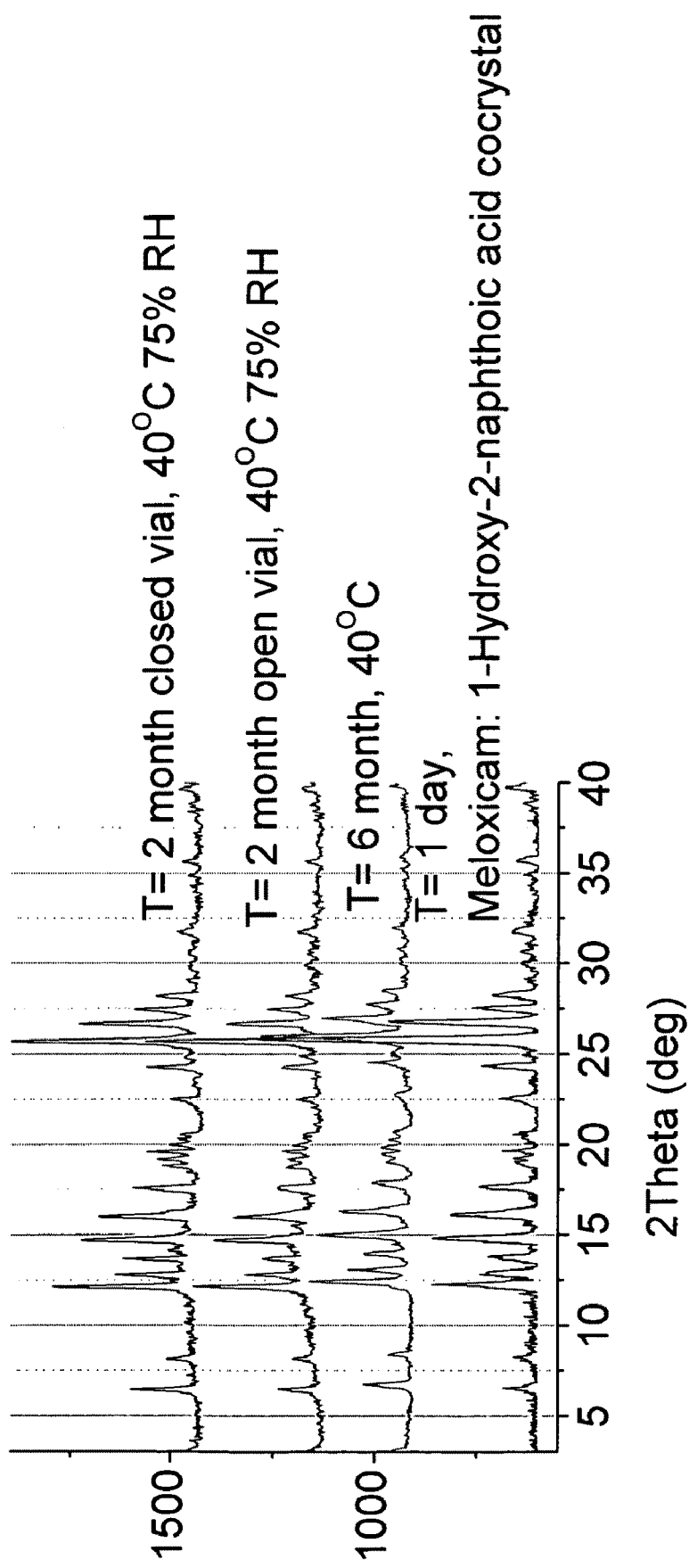

FIG. 59. PXRD diffractograms of accelerated stability testing of meloxicam and 1-hydroxy-2-naphthoic acid cocrystals. All 6 months tests were open vial tests.

Figure 60:
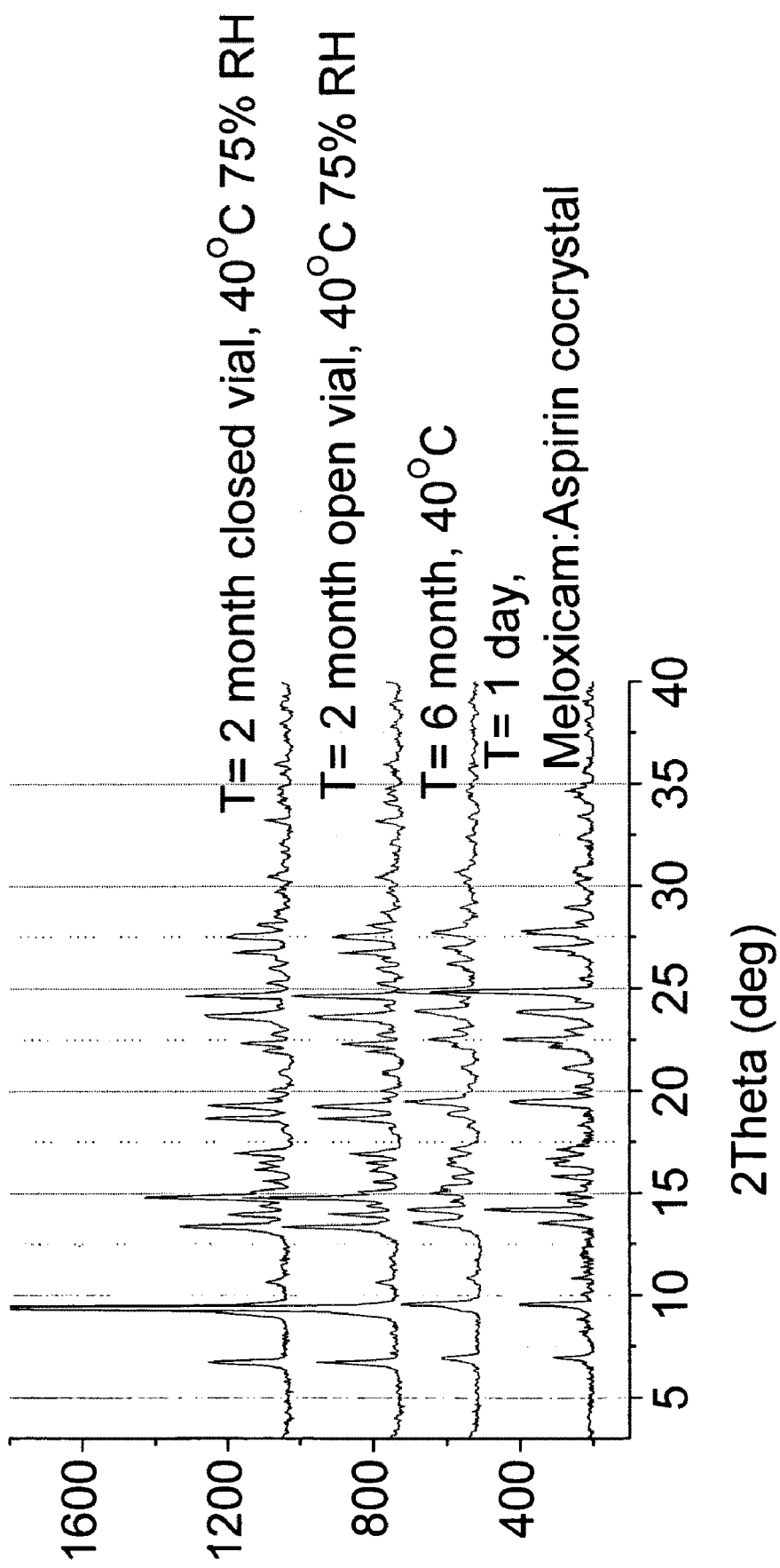

FIG. 60. PXRD diffractograms of accelerated stability testing of meloxicam and aspirin cocrystals. All 6 months tests were open vial tests.

Figure 61:
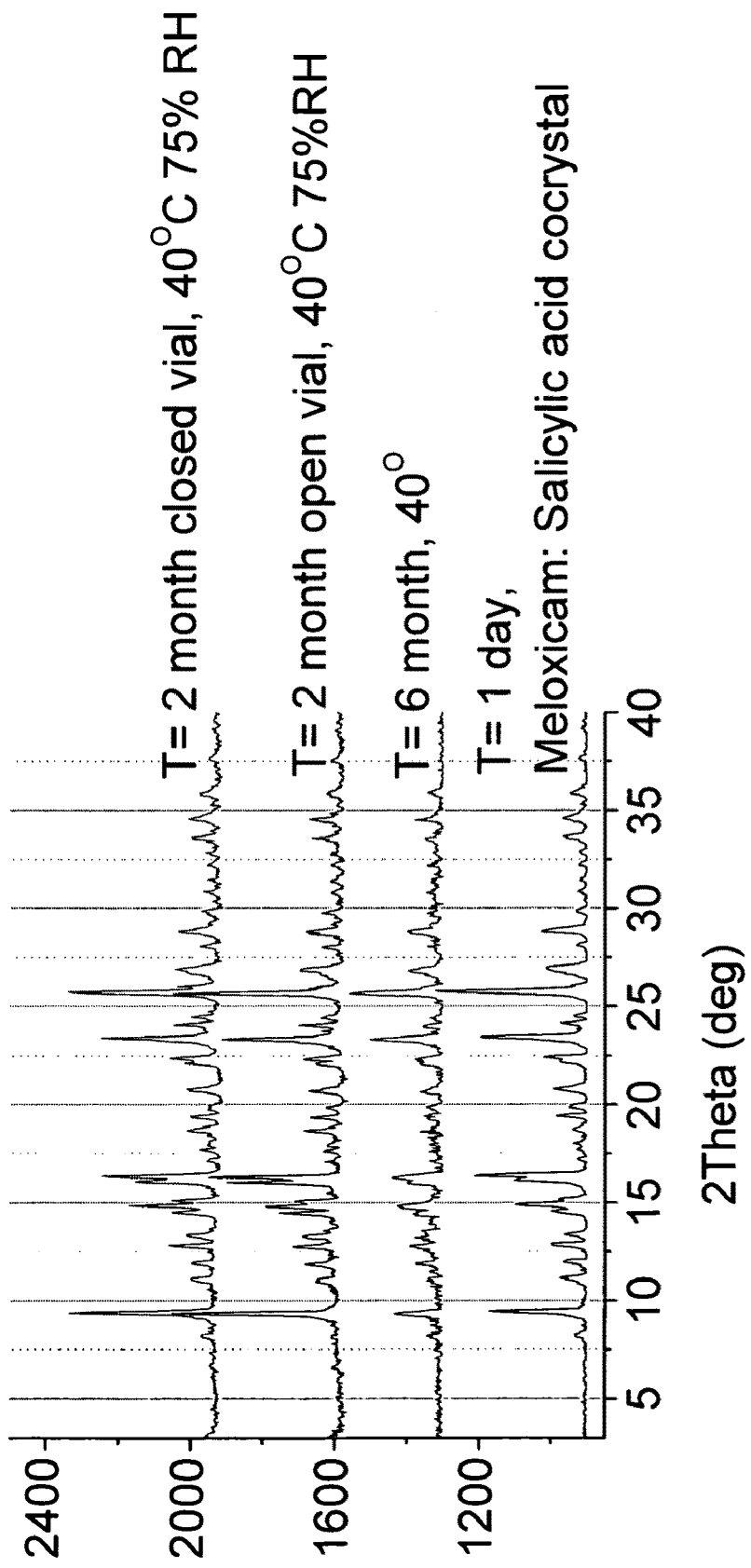

FIG. 61. PXRD diffractograms of accelerated stability testing of meloxicam and salicylic acid cocrystals, form III. All 6 months tests were open vial tests.

Figure 62:
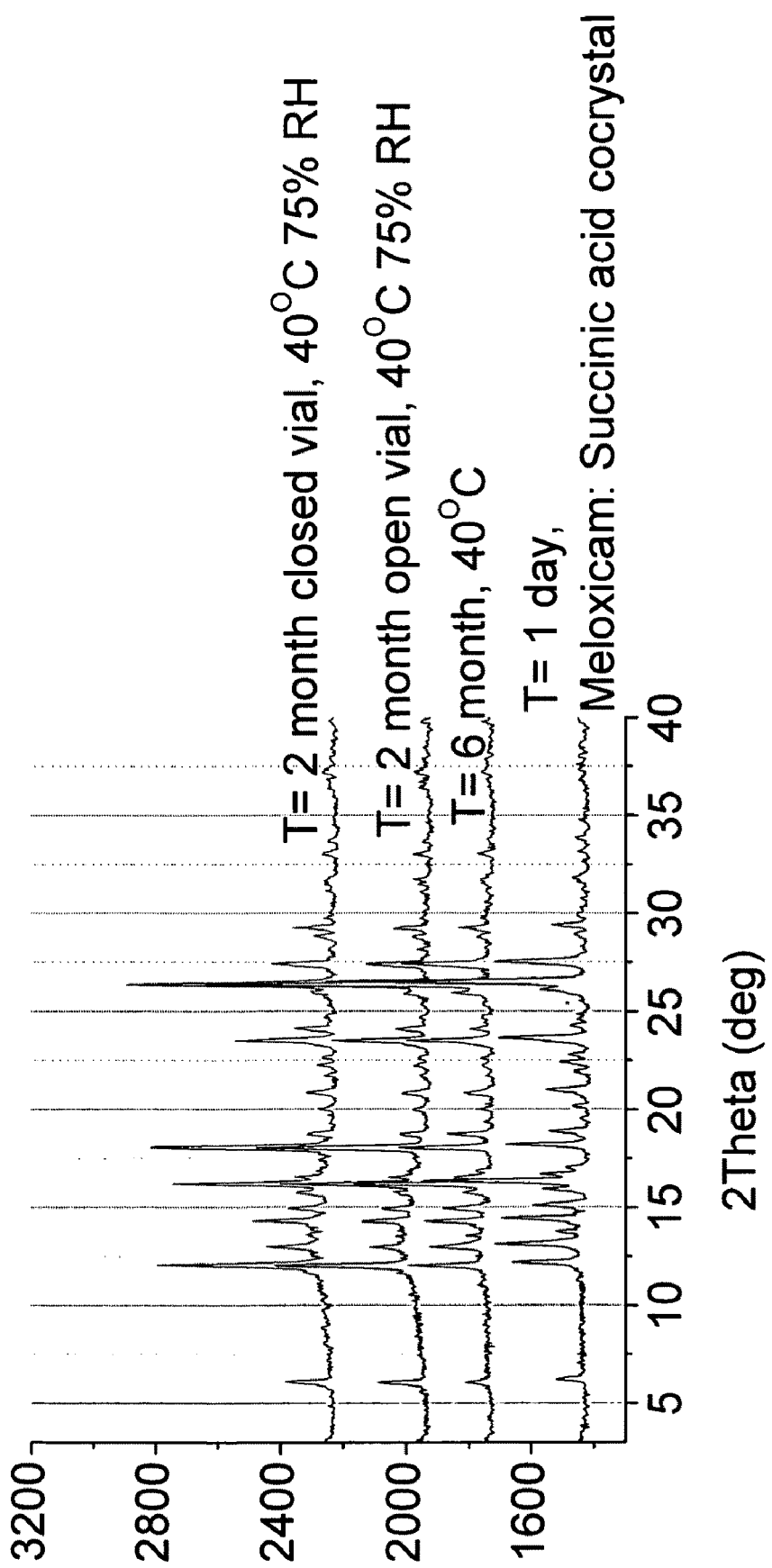

FIG. 62. PXRD diffractograms of accelerated stability testing of meloxicam and succinic acid cocrystals. All 6 months tests were open vial tests.

Figure 63:
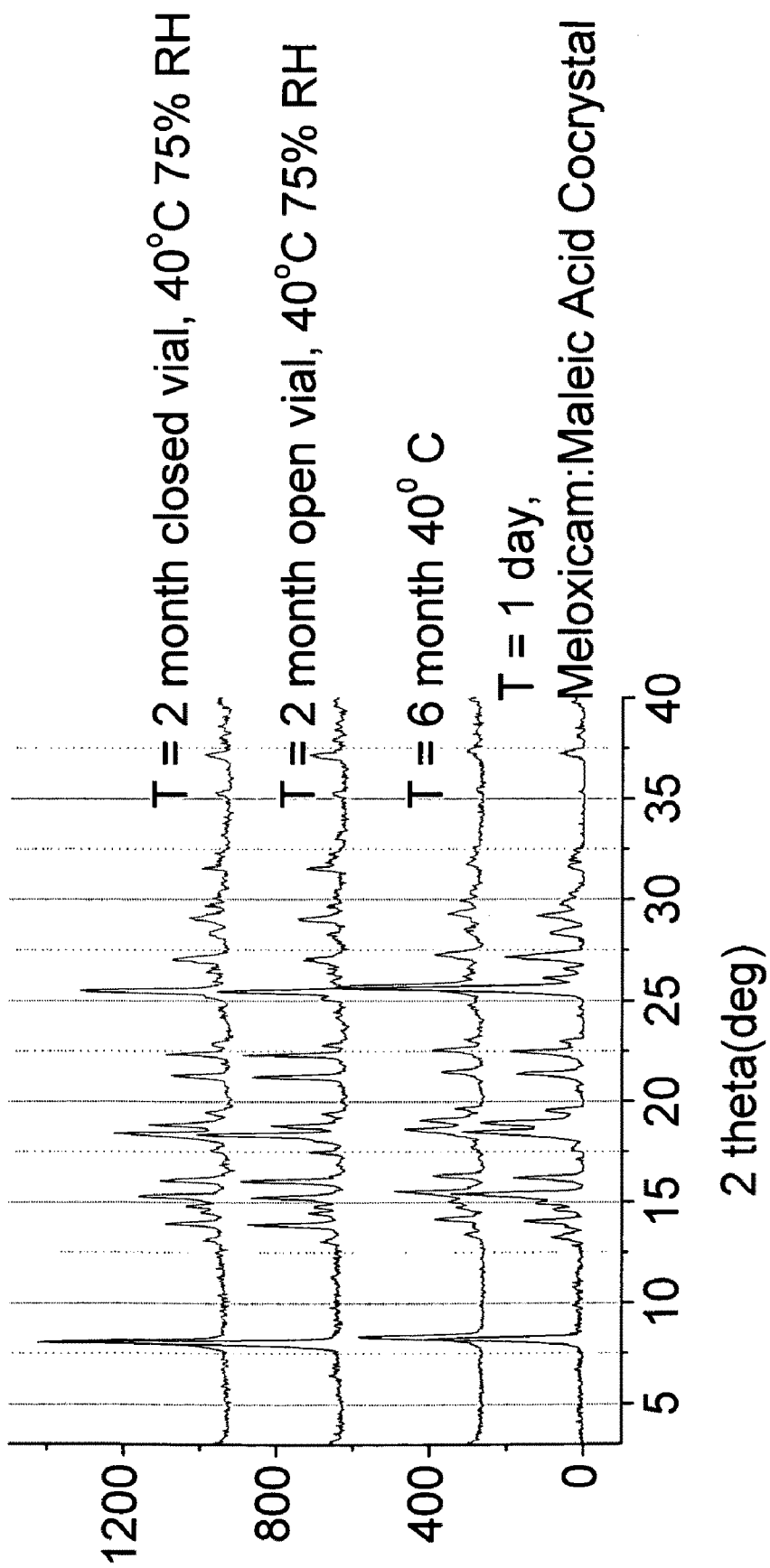

FIG. 63. PXRD diffractograms of accelerated stability testing of meloxicam and maleic acid cocrystals. All 6 months tests were open vial tests.

Figure 64:
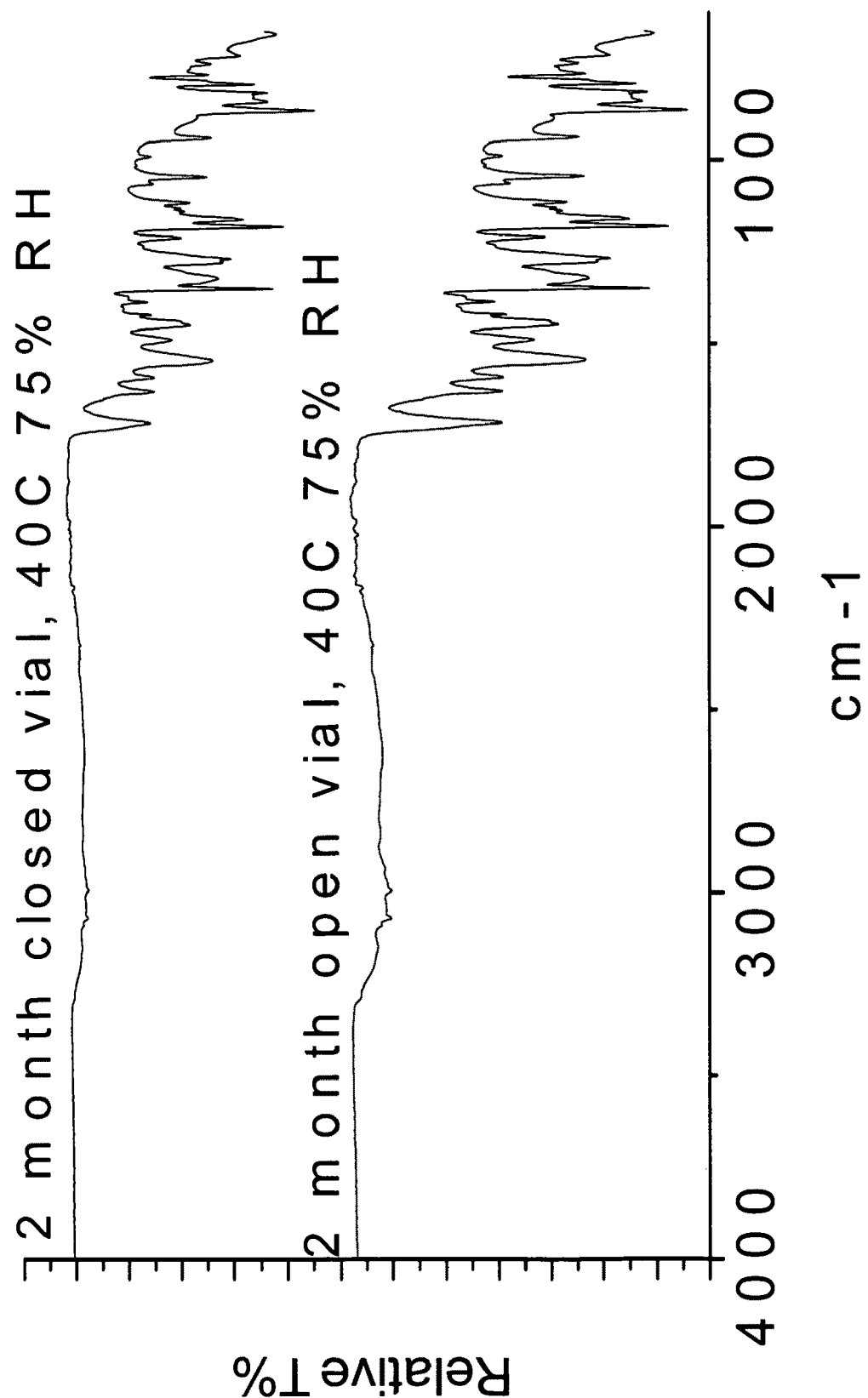

FIG. 64. FTIR spectra of two month accelerated stability testing of cocrystals of meloxicam and maleic acid cocrystals with open or closed vials.

Figure 65:
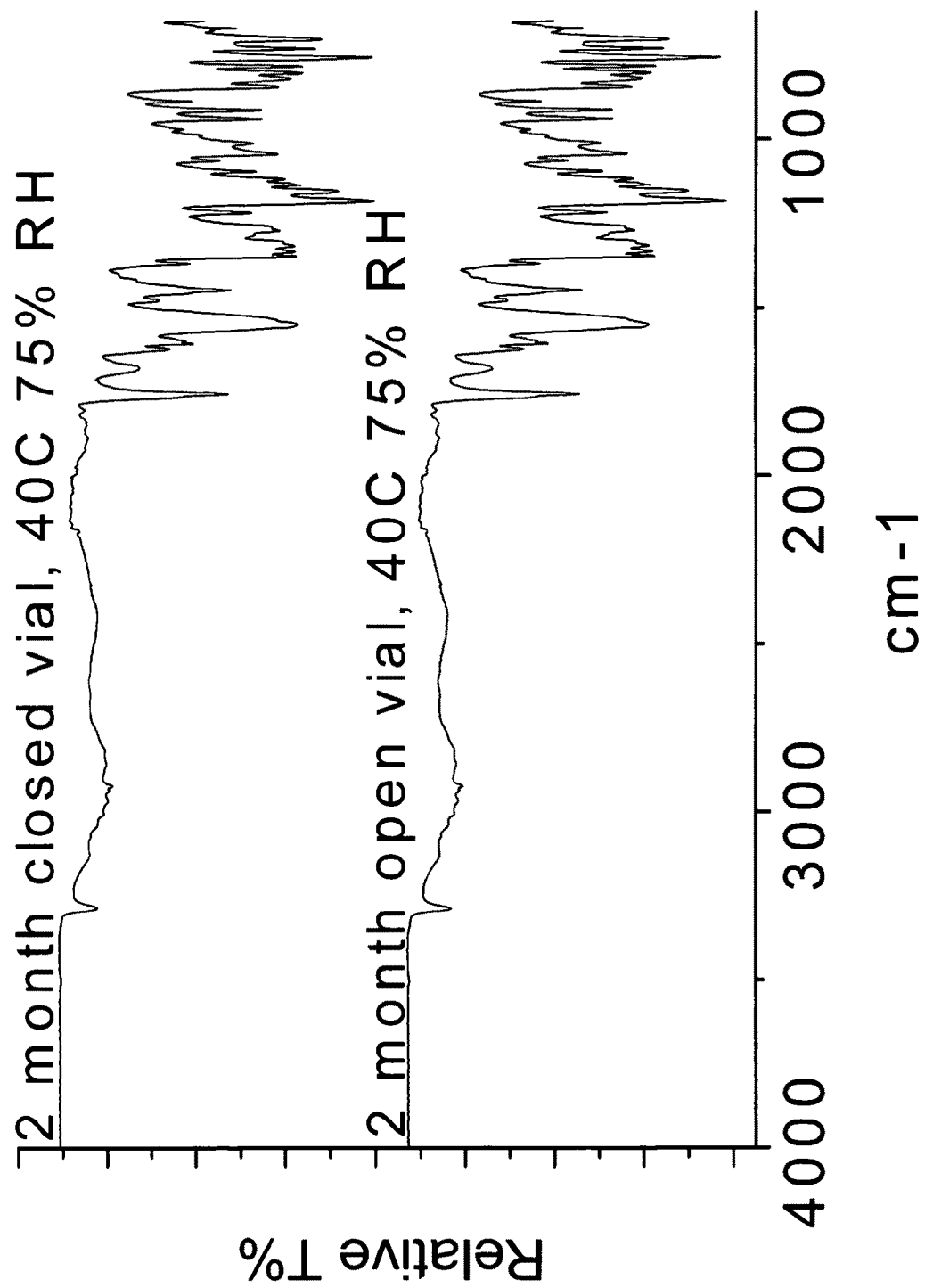

FIG. 65. FTIR spectra of two month accelerated stability testing of cocrystals of meloxicam and aspirin cocrystals with open or closed vials.

Figure 66:
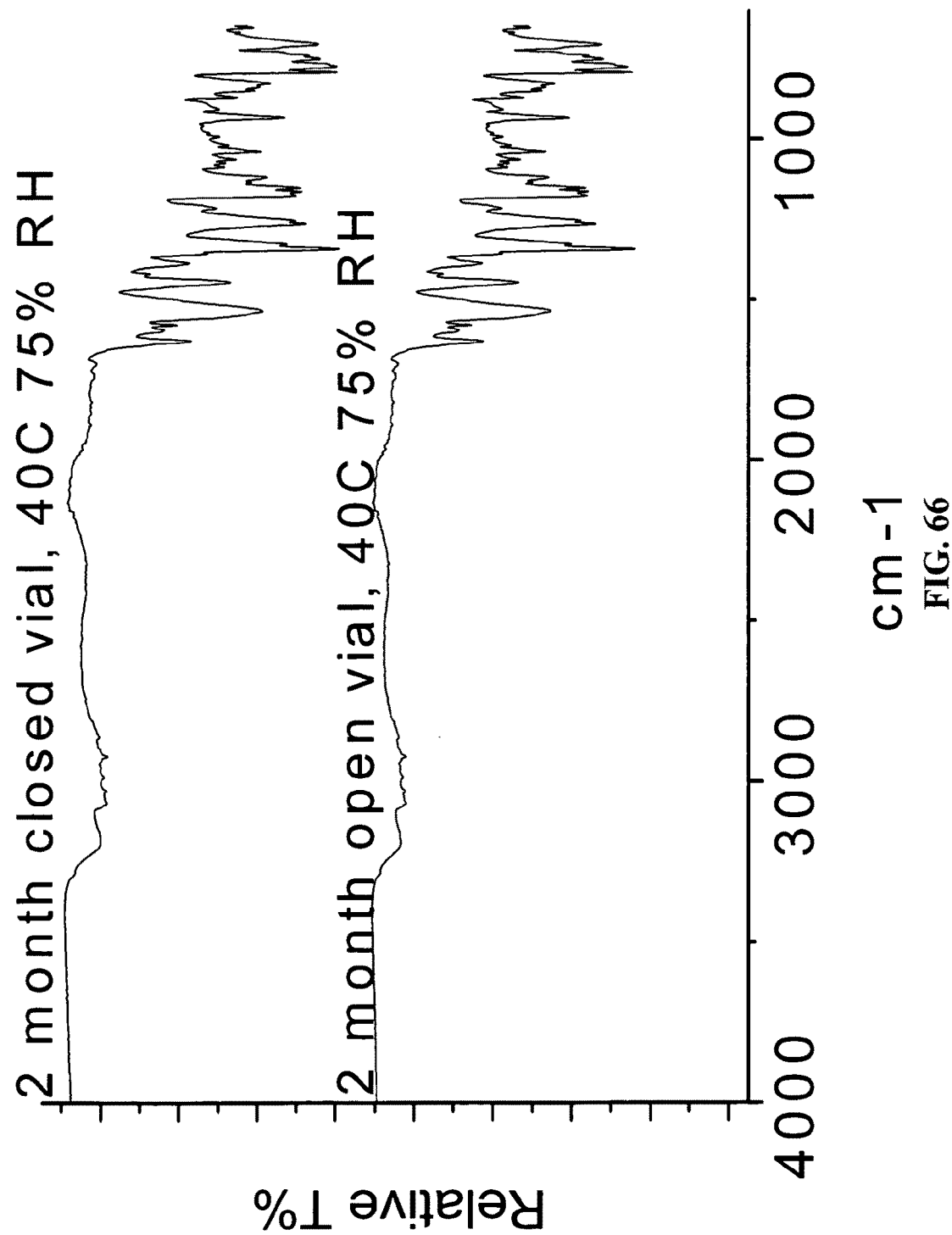

FIG. 66. FTIR spectra of two month accelerated stability testing of cocrystals of meloxicam and 1-hydroxy-2-naphthoicacid cocrystals with open or closed vials.

Figure 67:
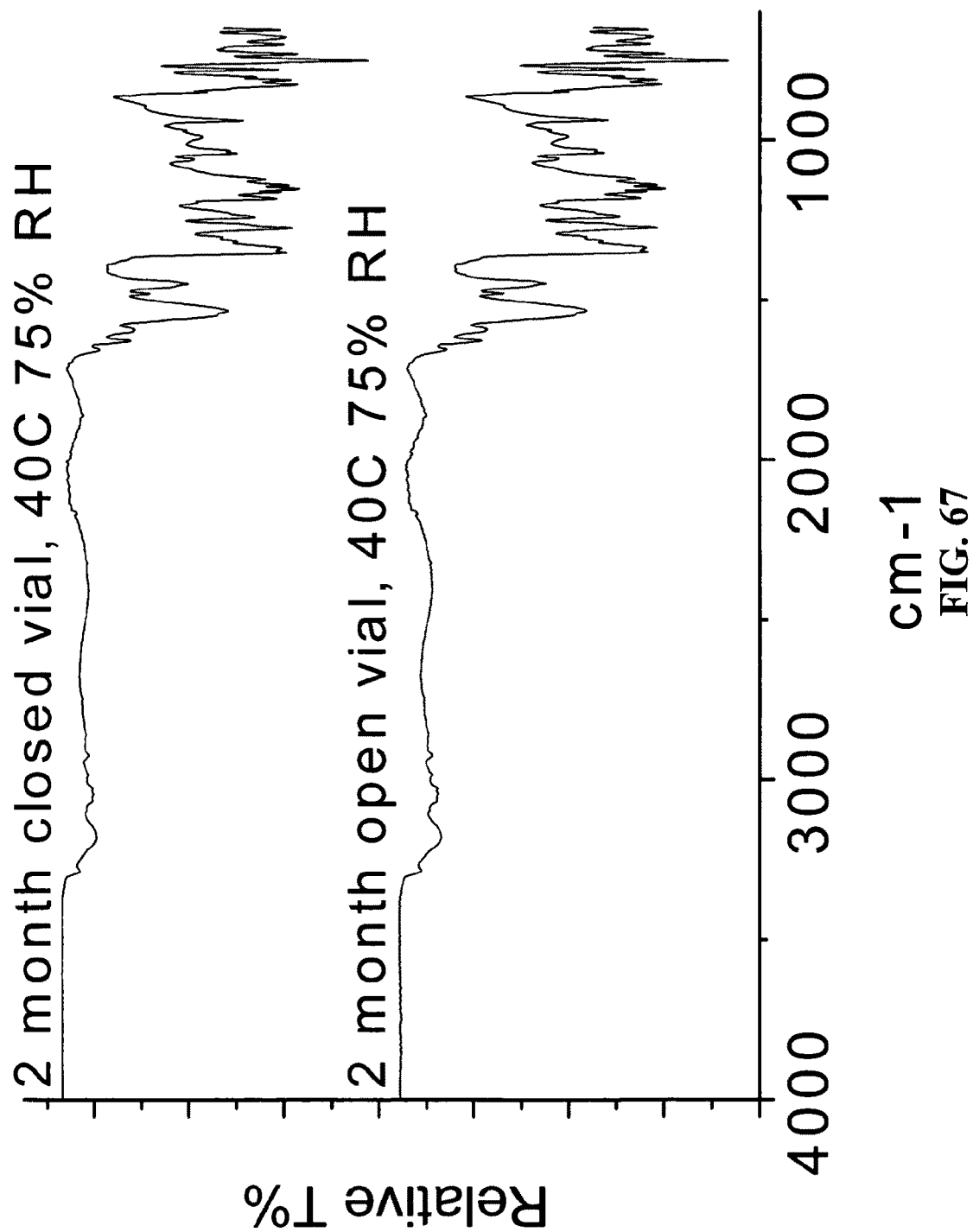

FIG. 67. FTIR spectra of two month accelerated stability testing of cocrystals of meloxicam and salicylic acid cocrystals, form III with open or closed vials.

Figure 68:
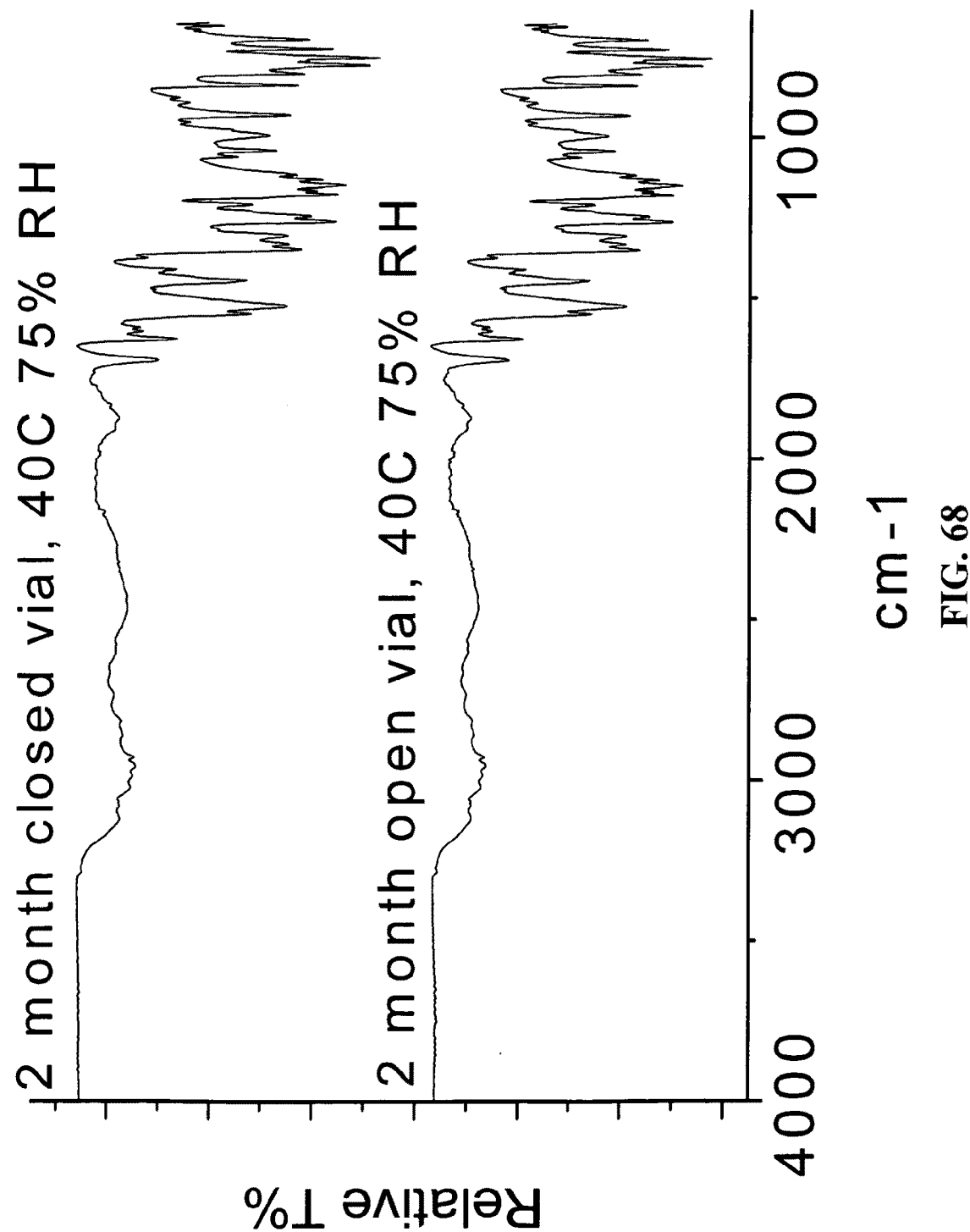

FIG. 68. FTIR spectra of two month accelerated stability testing of cocrystals of meloxicam and succinic acid cocrystals with open or closed vials.

Figure 69:
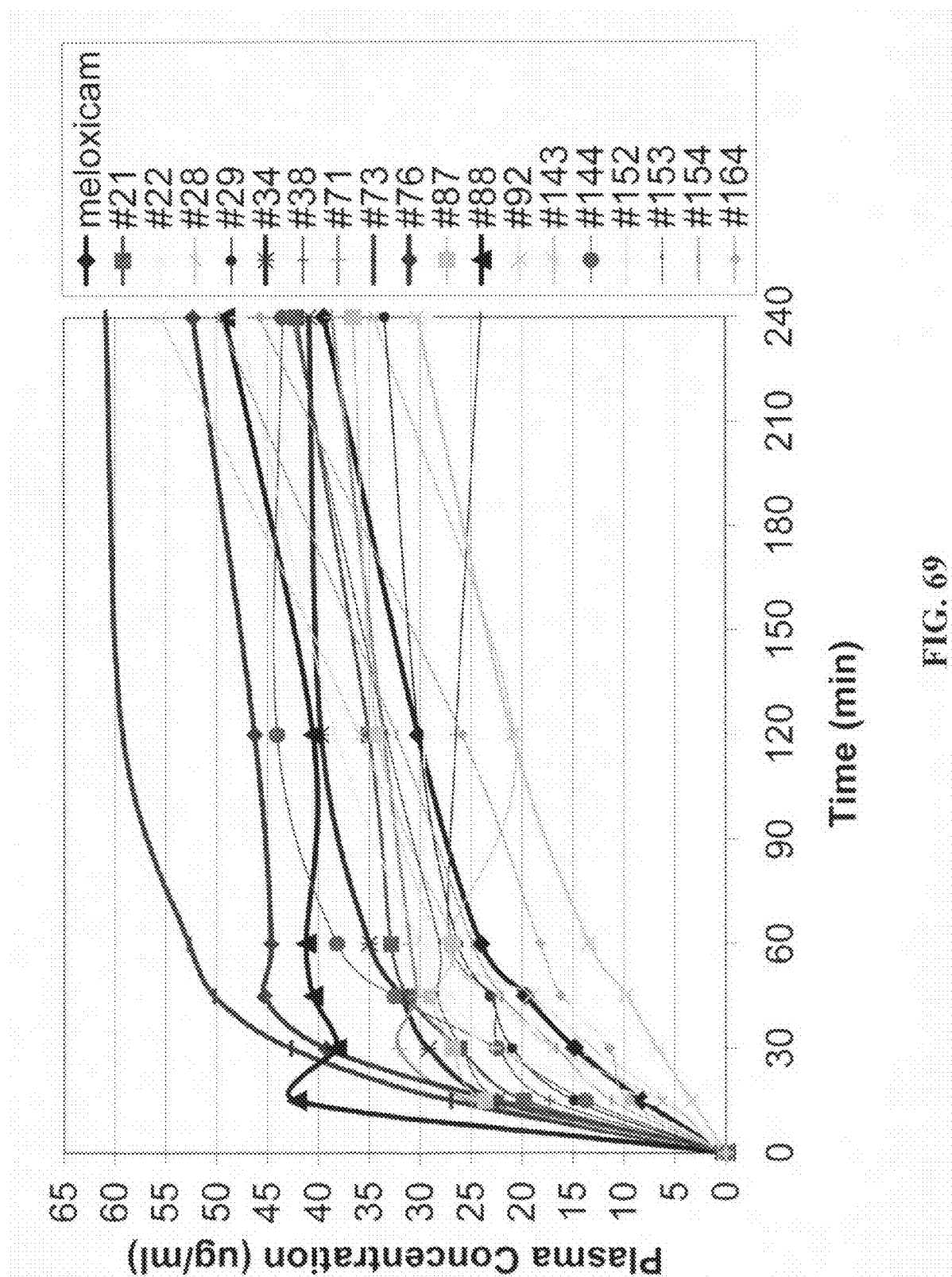

FIG. 69. Absorption profile of selected meloxicam cocrystals and pure meloxicam in rat.

Figure 70:
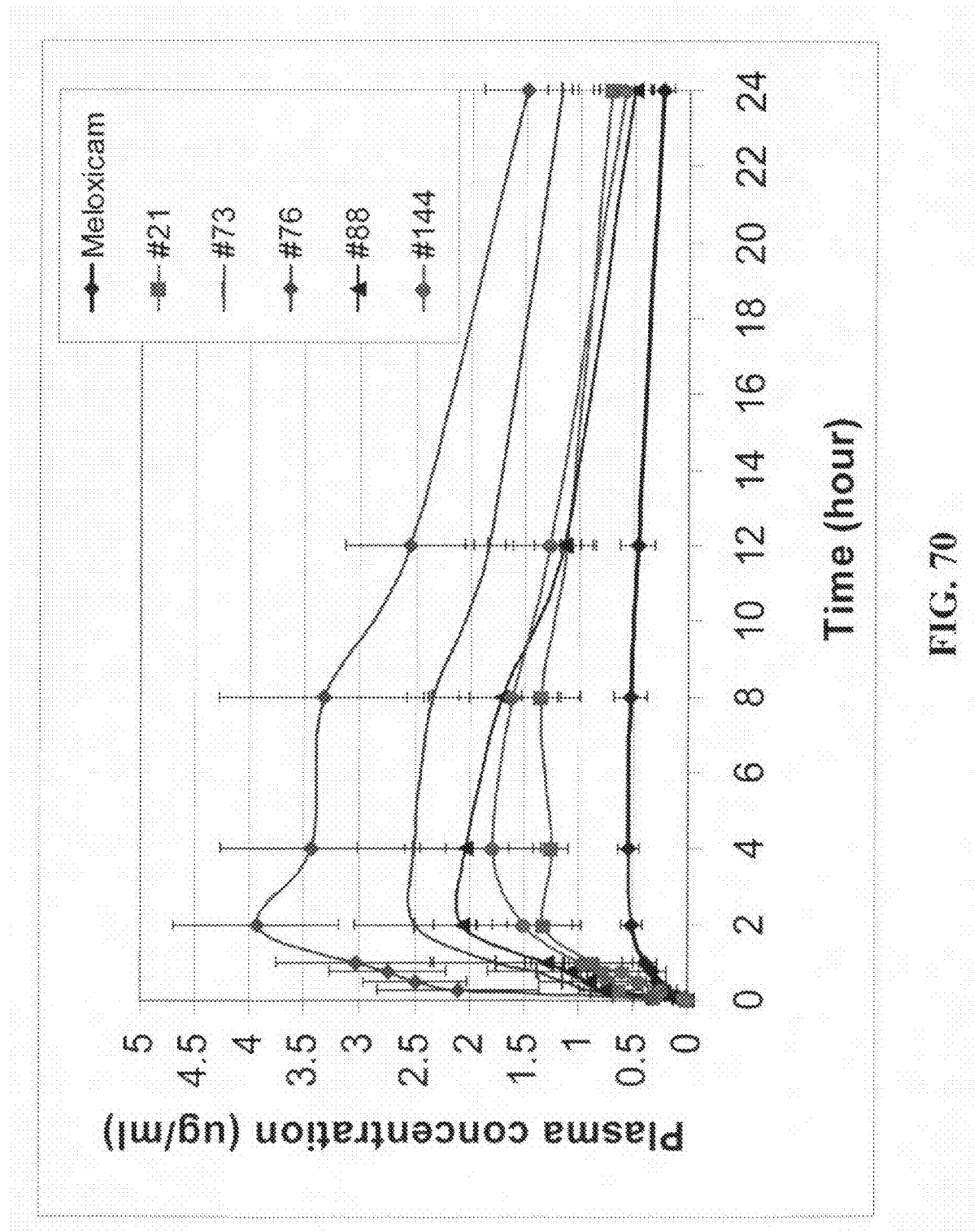

FIG. 70. Absorption profiles of selected meloxicam cocrystals and on the market (pure) meloxicam in male rats.

DETAILED DESCRIPTION OF THE INVENTION

In general, active pharmaceutical ingredients (APIs) in pharmaceutical compositions can be prepared in a variety of different forms. Such compounds can be prepared so as to have a variety of different chemical forms including chemical derivatives, solvates, hydrates, cocrystals and/or salts. Such compounds can also be prepared to have different physical forms. For example, they may be amorphous, may have different crystalline polymorphs, or may exist in different solvated or hydrated states. The discovery of new crystalline forms of a pharmaceutically useful compound may provide an opportunity to improve the performance characteristics of a pharmaceutical product. Additionally it expands the array of resources available for designing, for example, a pharmaceutical dosage form of a drug with a targeted release profile or other desired characteristics.

A specific characteristic that can be targeted includes the crystal form of an active pharmaceutical compound. By altering the crystal form it therefore becomes possible to vary the physical properties of the target molecule. For example, crystalline polymorphs typically have different aqueous solubility from one another, such that a more thermodynamically stable polymorph is less soluble than a less thermodynamically stable polymorph. In addition to water solubility, pharmaceutical polymorphs can also differ in properties such as shelf-life, bioavailability, morphology, vapor pressure, density, color, and compressibility. Accordingly, it is desirable to enhance the properties of an active pharmaceutical compound by forming molecular complexes such as a cocrystal, a salt, a solvate or hydrate with respect to aqueous solubility, rate of dissolution bioavailability, $C_{max}$, $T_{max}$, physico-chemical stability, down-stream processibility (e.g. flowability compressibility, degree of brittleness, particle size manipulation), crystallization of amorphous compounds, decrease in polymorphic form diversity, toxicity, taste, production costs, and manufacturing methods.

For oral delivery, it is frequently advantageous to have novel crystalline forms of drug materials that possess improved properties, including increased aqueous solubility and stability. It is also desirable in general to increase the dissolution rate of such solid forms, increase bioavailability, and provide a more rapid onset to quicken the therapeutic effect. It is also useful to have a crystal form of meloxicam which, when administered to a subject, reaches a peak plasma level faster and has a longer lasting therapeutic plasma concentration, when compared to other forms on a dose-for-dose basis.

Cocrystals, salts, solvates and hydrates of meloxicam of the present invention give rise to improved properties of meloxicam. For example, a new crystal form of meloxicam is particularly advantageous if it can improve the aqueous solubility of meloxicam. Additionally, the crystal properties conferred upon the new crystal forms of meloxicam are also useful when the bioavailability of meloxicam is improved and its plasma concentration and/or serum concentration improved. This is particularly advantageous for orally delivered meloxicam formulations. A number of novel meloxicam crystalline forms in addition to those disclosed in our provisional application (U.S. Provisional Application No. 61/011,902 filed on Jan. 22, 2008, and incorporated herein by reference in its entirety) have been synthesized, characterized, and reported herein. A selection of cocrystals here and in our previous application mentioned above has been fed orally to rats and their concentration in plasma measured. They clearly showed an improved rate of dissolution, plasma concentration and bioavailability compared to that of pure meloxicam. The techniques and approaches set forth in the present disclosure can further be used by the person of ordinary skill in the art to carry out an in-vivo study in rats and prepare obvious variants thereof, said variants considered to be part of the inventive disclosure.

API:

Meloxicam as a starting material used in all experiments in this disclosure was supplied by Jai Radhe Sales, India with purity of 99.5% and used without further purification All other pure chemicals (Analytical Grade) were supplied by Sigma-Aldrich and used without further purification.

Test Subjects:

Male Sprague-Dawley rats, 250-300 g, received with a surgically implanted jugular catheter in place from (Harlan or Taconic Laboratories, USA). Animals were housed one per polycarbonate cage utilizing individual cage cards, with free access to food and water in accordance with NIH guidelines. Animals were quarantined at least 24 hrs after arrival prior to use and patency of the implanted catheter determined on the day of the test. Environmental controls for the animal room were set to maintain 18 to 26° C., a relative humidity of 30 to 70%, a minimum of 10 air changes/hour, and a 12-hour light/12-hour dark cycle. Rats historically have been used in safety evaluation and PK screening studies and are recommended by appropriate regulatory agencies. In addition, rats have also been established as an appropriate species for assessing the absorption of meloxicam. The dose was 1 mg/kg of pure meloxicam and 1 mg/kg of meloxicam in meloxicam cocrystals (dose is measured as meloxicam, not as the cocrystal meloxicam form). Each rat was weighed and the dose volume adjusted accordingly so that the effect of weight variability on results of study was eliminated and that each rat received 1 mg/kg dose.

Dose Preparation:

Powders of novel meloxicam cocrystals and the commercially available meloxicam were passed between two sieves 53-75 micron (i.e. only the fraction of powder between the sieves was used in this study) to reduce the effect of particle size on rate of dissolution of test meloxicam and meloxicam cocrystals. The dose was prepared by suspending the sieved powders in 1 ml of 5% PEG 400 with 95% methylcellulose solution (weight percentage); methylcellulose solution is prepared by dissolving 0.5% methylcellulose in water (weight percentage). All meloxicam samples are delivered by feeding needle (gavage) through oral and esophagus to stomach of the rat. The reason for such dosing route is that rat has been validated as an appropriate model for human oral absorption of meloxicam.

In addition, IV comparator group of 5 rats was used to calculate MAT (mean absorption time) and ka (absorption rate constant) parameters since such parameters cannot be determined for the oral groups. IV dose was prepared in PEG400:DMSO formulation to ensure a soluble formulation of meloxicam.

Sampling:

200 micro liters of blood withdrawn from the indwelling intravenous catheter at 5 minutes, 15 minutes, 30 minutes, 45 minutes, 1, 2, 4, 8, 12 and 24 hours to provide sufficient amount of serum for analysis. 5 rats were used per meloxicam cocrystal formulation and pure meloxicam. The cocrystal formers for each cocrystal used in this experiment is provided in Table 1, below. Results are provided in Tables 2, 3 and 4, below.

TABLE 1

List of cocrystal formers to synthesize meloxicam cocrystals.

| Number | Cocrystal Former |
|---|---|
| 21 | Maleic acid |
| 22 | Malonic acid |
| 28 | Glycolic acid |
| 29 | Gentisic acid |
| 34 | 4-Hydroxybenzoic acid |
| 38 | (+)-camphoric acid |
| 71 | L-Malic acid |
| 73 | Aspirin |
| 76 | 1-Hydroxy-2-naphthoic acid |
| 87 | Salicylic acid (Form I) |
| 88 | Salicylic acid (Form III) |
| 92 | Glutaric acid |
| 143 | Fumaric acid |
| 144 | Succinic acid |
| 152 | Adipic acid |
| 153 | Benzoic acid |
| 154 | DL-Malic acid |
| 164 | Hydrocinnamic acid |

TABLE 2

Rat plasma concentrations for pure and cocrystal meloxicam.
Cocrystal drug (meloxicam) plasma concentration (μg/ml)

| Time (min) | 0 | 15 | 30 | 45 | 60 | 120 | 240 |
|---|---|---|---|---|---|---|---|
| Pure drug plasma conc. (μg/ml) | 0 | 8.19 | 14.83 | 19.63 | 24.03 | 30.19 | 39.40 |
| 21 | 0.3 | 19.77 | 26.13 | 31.19 | 32.84 | 35.02 | 42.12 |
| 22 | 0 | 7.51 | 22.15 | 27.00 | 29.33 | 29.57 | 29.23 |
| 28 | 0 | 6.25 | 16.88 | 22.66 | 27.26 | 20.77 | 34.50 |
| 29 | 0 | 14.89 | 20.96 | 23.15 | 26.32 | 30.13 | 33.45 |
| 34 | 0 | 22.38 | 29.17 | 31.91 | 34.99 | 39.69 | 40.86 |
| 38 | 0 | 17.27 | 22.26 | 22.85 | 27.00 | 26.46 | 24.03 |
| 71 | 0 | 24.98 | 32.05 | 30.38 | 30.95 | 33.58 | 38.59 |
| 73 | 0 | 26.94 | 42.67 | 50.18 | 52.67 | 59.23 | 60.85 |
| 76 | 0 | 22.41 | 39.24 | 45.29 | 44.60 | 46.24 | 52.24 |
| 87 | 0 | 23.61 | 26.76 | 28.85 | 26.79 | 34.16 | 36.54 |
| 88 | 0 | 42.10 | 38.19 | 40.48 | 41.18 | 40.50 | 49.13 |

TABLE 2-continued

Rat plasma concentrations for pure and cocrystal meloxicam.
Cocrystal drug (meloxicam) plasma concentration (μg/ml)

| Time (min) | 0 | 15 | 30 | 45 | 60 | 120 | 240 |
|---|---|---|---|---|---|---|---|
| 92 | 0 | 5.61 | 13.16 | 19.11 | 27.72 | 35.94 | 55.35 |
| 143 | 0 | 3.33 | 6.69 | 9.69 | 13.39 | 20.93 | 30.23 |
| 144 | 0 | 13.76 | 22.43 | 32.54 | 38.13 | 44.02 | 43.47 |
| 152 | 0 | 9.72. | 22.85 | 28.37 | 30.09 | 38.23 | 47.85 |
| 153 | 0 | 21.94 | 25.88 | 28.30 | 28.11 | 33.31 | 42.51 |
| 154 | 0 | 11.19 | 16.59 | 21.96 | 24.90 | 32.31 | 49.72 |
| 164 | 0 | 9.53 | 11.42 | 16.19 | 18.24 | 25.918 | 45.70 |

TABLE 3

Meloxicam plasma concentration values (N = 5)
following 1 mg/kg oral administration to male rats.

| Time (hour) | Pure meloxicam plasma conc. (μg/ml) | Cocrystal meloxicam plasma concentration (μg/ml) | | | | |
|---|---|---|---|---|---|---|
| | | 21 | 73 | 76 | 88 | 144 |
| 0.0833 | 0.02 | 0.3 | 0.13 | 0.34 | 0.145 | 0.03 |
| 0.25 | 0.19 | 0.62 | 0.87 | 2.1 | 0.7675 | 0.23 |
| 0.5 | 0.28 | 0.72 | 1.14 | 2.49 | 0.8975 | 0.45 |
| 0.75 | 0.32 | 0.78 | 1.37 | 2.74 | 1.0625 | 0.6 |
| 1 | 0.39 | 0.86 | 1.74 | 3.04 | 1.2825 | 0.96 |
| 2 | 0.51 | 1.31 | 2.49 | 3.94 | 2.06 | 1.5 |
| 4 | 0.54 | 1.25 | 2.51 | 3.43 | 2.0425 | 1.78 |
| 8 | 0.53 | 1.34 | 2.34 | 3.33 | 1.7 | 1.6 |
| 12 | 0.46 | 1.11 | 1.83 | 2.55 | 1.1425 | 1.26 |
| 24 | 0.24 | 0.7 | 1.16 | 1.48 | 0.5 | 0.58 |

TABLE 4

Mean pharmacokinetic values (N = 5) of meloxicam and meloxicam cocrystals
following 1 mg/kg oral administration to male rats, where MRT = Mean
residence time, MAT = Mean absorption time, ka = Absorption rate constant,
$C_{max}$ = Peak plasma concentration, $AUC_{24}$ = area under the plasma
concentration-time curve at 24 h, F = Bioavailability, nc = Not calculated

| Treatment | Route | Time to Reach 0.59 μg/ml * (min) | MRT (h) | MAT (h) | ka (1/h) | Cmax (μg/mL) | AUC (μg-h/mL) | F (%) |
|---|---|---|---|---|---|---|---|---|
| Meloxicam | Oral | 270.0 | 21.80 | 7.10 | 0.141 | 0.59 | 10.0 | 15.7 |
| Cocrystal 76 | Oral | 6.5 | 21.30 | 6.60 | 0.152 | 4.15 | 62.5 | 98.3 |
| Cocrystal 73 | Oral | 10.6 | 24.56 | 9.86 | 0.101 | 2.70 | 44.1 | 69.4 |
| Cocrystal 88 | Oral | 11.3 | 16.25 | 1.55 | 0.645 | 2.23 | 29.6 | 46.5 |
| Cocrystal 21 | Oral | 13.4 | 35.10 | 20.40 | 0.049 | 1.49 | 25.3 | 39.8 |
| Cocrystal 144 | Oral | 45.1 | 18.06 | 3.36 | 0.298 | 1.78 | 28.4 | 44.7 |
| Meloxicam | IV | nc | 14.70 | nc | nc | nc | 63.6 | nc |

* = Calculated based upon interpolation of time vs. concentration data

Analytical Techniques:

The analytical methods used to observe the crystalline forms include FTIR (fourier transform infra red spectroscopy), (PXRD) powder x-ray diffraction and DSC (differential scanning calorimetry). The particular methodology used in such analytical techniques should be viewed as illustrative, and not limiting in the context of data collection. For example, the particular instrumentation used to collect data may vary; routine operator error or calibration standards may vary; sample preparation method may vary (for example, the use of the KBr disk or Nujol mull technique for FTIR analysis).

Powder X-Ray Diffraction (PXRD): All meloxicam cocrystal products were observed by a D-8 Bruker X-ray Powder Diffractograph (Bruker, USA) using Cu Kα (λ=1.540562 Å), 40 kV, 40 mA. The data was collected over an angular range of 3° to 40° 2θ in continuous scan mode using a step size of 0.05° 2θ and a scan speed of 1.0°/min.

Differential Scanning Calorimetry (DSC): All meloxicam cocrystals were analyzed by the Perkin-Elmer Diamond system (Perkin Elmer, USA), using standard pans and generally heated at a rate of 10° C./min (scan rate).

Fourier Transform Infrared Spectroscopy (FTIR): FTIR analysis was performed on a Perkin Elmer Spectrum 100 FTIR spectrometer (Perkin Elmer, USA) equipped with a solid-state ATR accessory.

Sample Analysis:

Samples were thawed on the day of analysis and processed using analytical procedures developed to optimize for meloxicam detection. Briefly, using a gradient elution with a Waters Symmetry $C_{18}$ column (Waters Inc. USA), LCMS with selective reaction monitoring, protein precipitation of the plasma sample using acetonitrile where an LOQ of 50 ng/ml was achieved. Pharmacokinetic parameters were calculated from individual animal samples using appropriate software (PK Solutions 2.0, Summit Research Services, Montrose, Calif., USA). The analysis of meloxicam blood concentration was performed by LC fitted with MS detector using the internal standard method to quantify results which can be used by the person of ordinary skill in the art.

Process Scale-Up:

In addition to the 1 g level of meloxicam cocrystal formulations of meloxicam:salicylic acid form III, meloxicam:1-hydroxy-2-naphthoic acid, meloxicam:aspirin, meloxicam:maleic acid and meloxicam:succinic acid prepared through dry, solvent drop grinding, heating, solvent evaporation, solution and slurry crystallization, it was possible to scale this process of 1 g to 70 g level, single batch of meloxicam cocrystals. The results of the analysis of the 70 g single batch samples by PXRD, FTIR and DSC were the same as that obtained for 1 g level. This suggests that scaling up of this process was achievable with little or no difficulty.

Accordingly, in the first aspect, the present invention includes cocrystals of meloxicam and adipic, benzoic, fumaric, glutaric, 4-hydroxybenzoic acid, malic, maleic, succinic, salicylic, acetylsalicylic, 1-hydroxy-2-naphthoic, malonic, glycolic, 2,5-dihydroxybenzoic and camphoric acid as well as maltol, ethyl maltol, and hydrocinnamic acid which are capable of cocrystallizing from the solid-state, for example, through dry or solvent grinding, heating or solvent evapouration of their solution in single or mixture solvent systems.

Another aspect of the invention provides cocrystals of; meloxicam:fumaric acid by dissolving both compounds in (tetrahydrofuran) THF:IPA (isopropyl alcohol) (3:1 v/v) and allowing the solvent mixtures to evaporate.

Another aspect of the invention provides cocrystals of, meloxicam:fumaric acid from dissolving both compounds in dioxane:methanol, (3:1 v/v) and allowing the solvent mixtures to evaporate.

Another aspect of the invention provides cocrystals of meloxicam: 1-hydroxy-2-naphthoic acid by dissolving both compounds in THF:IPA (3:1 v/v) and allowing the solvent mixtures to evaporate.

Another aspect of the invention provides cocrystals of meloxicam: 1-hydroxy-2-naphthoic acid by dissolving both compounds in dioxane:methanol (3:1 v/v) and allowing the solvent mixtures to evaporate.

Another aspect of the invention provides cocrystals of meloxicam and adipic, benzoic, fumaric, malic, maleic, succinic, saliycylic, acetyl salicylic, 1-hydroxy 2-naphthoic, malonic, glycolic, 2,5-dihydroxybenzoic, camphoric acid, maltol, ethyl maltol, and hydrocinnamic acid suitable for a pharmaceutical formulation than can be delivered via different routes to the human body.

Another aspect of this disclosure provides different polymorphic forms of meloxicam and (+) camphoric acid cocrystal. This was achieved by different methods including changing the solvent used for grinding.

Another aspect of this disclosure provides different polymorphic forms of meloxicam and salicylic acid cocrystal. This was achieved by different methods including changing the solvent used for grinding Another aspect of the invention provides cocrystals of form III of meloxicam:salicylic acid by dissolving and slurry both compounds in a small volume of THF, ethyl acetate and acetone.

Another aspect of this disclosure provides cocrystals of meloxicam and adipic, benzoic, fumaric, glutaric, 4-hydroxybenzoic acid, malic, maleic, succinic, saliycylic, acetylsalicylic, 1-hydroxy 2-naphthoic, malonic, glycolic, 2,5-dihydroxybenzoic and camphoric acid, maltol, ethyl maltol, and hydrocinnamic acid that have been observed by their x-ray powder diffraction patterns and FTIR spectra Another aspect of the invention provides 1 g of cocrystals of meloxicam:salicylic acid, form III by dissolving and slurry both compounds in a small volume of THF, ethyl acetate and acetone, preferably ethyl acetate Another aspect of the invention provides 1 g of cocrystals of meloxicam: 1-hydroxy 2-naophthoic acid from slurry of both compounds in a small volume of THF, ethyl acetate and acetone, preferably ethyl acetate.

Another aspect of the invention provides 1 g of cocrystals of meloxicam:aspirin from a slurry of both compounds in a small volume of THF, ethyl acetate and acetone, preferably ethyl acetate.

Another aspect of the invention provides 1 g of cocrystals of meloxicam:maleic acid from slurry of both compounds in a small volume of THF, ethyl acetate and acetone, most preferably ethyl acetate.

Another aspect of the invention provides 1 g of cocrystals of meloxicam:succinic acid from slurry of both compounds in a small volume of THF, ethyl acetate and acetone, preferably ethyl acetate.

Another aspect of the invention provides a method of producing tens of grams levels (e.g. 70 g) of cocrystals of meloxicam:succinic acid from slurry of both compounds in relatively small volumes of THF and ethyl acetate, preferably ethyl acetate and a small amount of this batch has been used to conduct the PK study in animals (male rats).

Another aspect of the invention provides a method of producing tens of grams levels (e.g. 70 g) of cocrystals of meloxicam:maleic acid from slurry of both compounds in relatively small volumes of THF and ethyl acetate, preferably ethyl acetate and a small amount of this batch has been used to conduct the PK study in animals (male rats).

Another aspect of the invention provides a method of producing tens of grams levels (e.g. 70 g) of cocrystals of meloxicam: 1-hydroxy-2-naphthoic acid from slurry of both compounds in relatively small volumes of THF and ethyl acetate, preferably ethyl acetate and a small amount of this batch has been used to conduct the PK study in animals (male rats).

Another aspect of the invention provides a method of producing tens of grams levels (e.g. 70 g) of cocrystals of meloxicam:salicylic acid form III from slurry of both compounds in relatively small volumes of THF and ethyl acetate, preferably ethyl acetate and a small amount of this batch has been used to conduct the PK study in animals (male rats).

Another aspect of the invention provides a method of producing tens of grams levels (e.g. 70 g) of cocrystals of meloxicam:aspirin from slurry of both compounds in relatively small volumes of THF and ethyl acetate, preferably ethyl acetate and a small part of this batch has been used to study the PK profiles of meloxicam in animals (male rats).

Another aspect of the invention provides a method for comparing the 1 g and 70 g batches of meloxicam:succinic acid using different analytical techniques (e.g. PXRD, FTIR, DSC . . . etc) to show the similarity between the two different scale batches.

Another aspect of the invention provides a method for comparing the 1 g and 70 g batches of meloxicam:maleic acid using different analytical techniques (e.g. PXRD, FTIR, DSC . . . etc) to show the similarity between the two different scale batches.

Another aspect of the invention provides a method for comparing the 1 g and 70 g batches of meloxicam:salicylic acid form III using different analytical techniques (e.g. PXRD, FTIR, DSC . . . etc) to show the similarity between the two different scale batches.

Another aspect of the invention provides a method for comparing the 1 g and 70 g batches of meloxicam: 1-hydroxy-2-naphthoic acid using different analytical techniques (e.g. PXRD, FTIR, DSC . . . etc) to show the similarity between the two different scale batches.

Another aspect of the invention provides a method for comparing the 1 g and 70 g batches of meloxicam:aspirin using different analytical techniques (e.g. PXRD, FTIR, DSC . . . etc) to show the similarity between the two different scale batches.

Another aspect of the invention suggests that the 1 g batch was no different from the 70 g batch of cocrystals of meloxicam:succinic acid, meloxicam:maleic acid, meloxicam:salicylic acid meloxicam: 1-hydroxy-2-naphthoic acid and meloxicam:aspirin.

Another aspect of the invention suggests that scaling up of meloxicam cocrystals from 1 g to 70 g is achievable.

Another aspect of the invention provides cocrystals of meloxicam and aspirin, 1-hydroxy-2-naphthoic acid, succinic acid, maleic acid and salicylic acid suitable for a pharmaceutical formulation than can be delivered via different routes to the human body.

Another aspect of the invention provides data (PXRD profiles) that the cocrystals of meloxicam, salicylic, maleic, succinic, 1-hydroxy-2-naphthoic acid and aspirin are stable for 6 months during accelerated stability testing (2 months heated at 40° C., 75% RH open and closed vials, and 6 months heated at 40° C. open vial).

Another aspect of the invention provides data (FTIR profiles) that the cocrystals of meloxicam, salicylic, maleic, succinic, 1-hydroxy-2-naphthoic acid and aspirin are stable for 2 months during accelerated stability testing (2 months heated at 40° C., 75% RH) whether the vials kept in were open or closed.

The cocrystal formers listed in Table 2 of this disclosure and meloxicam novel cocrystal forms generated from them have already been reported in our provisional application (61/011,902 filed on 22 Jan. 2008)

Another aspect of the invention provides a 4 hr in-vivo study of meloxicam in blood of animal species, rats in this case. Where oral delivery of novel meloxicam cocrystal forms has led to dramatic increase in the drug concentration in rat's blood compared with that of the pure, commercially available meloxicam.

Another aspect of the invention provides a 4 hr in-vivo study of meloxicam in blood of animal species, male rats in this case, where powders of novel meloxicam cocrystals and the commercially available meloxicam were passed between two sieves 53-75 micron to reduce the effect of particle size on rate of dissolution before being suspended and orally delivered to male rats.

Another aspect of the invention provides a 4 hr in-vivo study of meloxicam in blood of animal species, male rats in this case, where novel meloxicam cocrystal and the commercially available meloxicam were suspended in 1 ml of 5% PEG 400 and 95% methylcellulose solution.

Another aspect of the invention for a 4 hr in-vivo study provides data points of level of absorption of meloxicam in which each data point for the novel meloxicam cocrystals is the average meloxicam level of 5 rats. Each data point of the pure commercially available meloxicam is the average of 10 rats in total.

Another aspect of the invention provides a 24 hr in-vivo study of meloxicam in blood of animal species, male rats in this case, where delivery of novel meloxicam cocrystal and the commercially available meloxicam were carried out using feeding needle (gavage).

Another aspect of the invention provides a 24 hr in-vivo study of meloxicam in blood of animal species, male rats in this case, where powders of novel meloxicam cocrystals and the commercially available meloxicam were passed between two sieves 53-75 micron to reduce the effect of particle size on rate of dissolution before being suspended and orally delivered to male rats.

Another aspect of the invention provides a 24 hr in-vivo study of meloxicam in blood of animal species, male rats in this case, where novel meloxicam cocrystal and the commercially available meloxicam were suspended in 1 ml of 5% PEG 400 and 95% methylcellulose solution.

Another aspect of the invention provides a 24 hr in-vivo study of meloxicam in blood of animal species, male rats in this case. Where oral delivery of novel meloxicam cocrystal forms has led to dramatic increase in the drug concentration in rat's blood compared with that of the pure, commercially available meloxicam.

Another aspect of this invention provides 24 hr in-vivo data about meloxicam cocrystals reaching the Cmax of the commercially available meloxicam in much shorter periods of time; minutes rather than hours.

Another aspect of the invention provides 24 hr in-vivo data points of level of absorption of meloxicam in which each data point for the novel meloxicam cocrystals is the average meloxicam level of 5 rats. Each data point of the pure commercially available meloxicam is also the average of 5 rats.

EXAMPLES

The following examples illustrate the invention without intending to limit the scope of the invention.

Example 1

Preparation of Meloxicam:Fumaric Acid Cocrystal (2:1)

176 mg of meloxicam was ground with 29 mg of fumaric acid and 400 µL of THF was added to the solid mixture. The solids gathered after grinding were stored in screw cap vials for subsequent analysis.

Example 2

Preparation of Meloxicam:Fumaric Acid Cocrystal (2:1)

176 mg of meloxicam was ground with 29 mg of fumaric acid and 400 µL of chloroform was added to the solid mixture. The solids gathered after grinding were stored in screw cap vials for subsequent analysis.

Example 3

Preparation of Meloxicam:Fumaric Acid Cocrystal (2:1)

88 mg of meloxicam was dissolved in 8 ml of THF:IPA (3:1 v/v) mixture, 15 mg of fumaric acid was added to the solution to form a single solution. The solution was then allowed to stand for several hours to effect the slow evaporation of solvent. The solids gathered were stored in screw cap vials for subsequent analysis.

Example 4

Preparation of Meloxicam:Fumaric Acid Cocrystal (2:1)

88 mg of meloxicam was dissolved in 8 ml of dioxane:methanol (3:1 v/v) mixture, 15 mg of fumaric acid was added to the solution to form a single solution. The solution was then allowed to stand for several hours to effect the slow evaporation of solvent. The solids gathered were stored in screw cap vials for subsequent analysis.

Example 5

Preparation of Meloxicam:Succinic Acid Cocrystal (2:1)

176 mg of meloxicam was ground with 30 mg of succinic acid and 400 µL of THF was added to the solid mixture. The solids gathered after grinding were stored in screw cap vials for subsequent analysis.

Example 6

Preparation of Meloxicam:Succinic Acid Cocrystal (2:1)

176 mg of meloxicam was ground with 30 mg of succinic acid and 400 µL of chloroform was added to the solid mixture. The solids gathered after grinding were stored in screw cap vials for subsequent analysis.

Example 7

Preparation of Meloxicam:Adipic Acid Cocrystal (2:1)

176 mg of meloxicam was ground with 37 mg of adipic acid and 400 µL of THF was added to the solid mixture. The solids gathered after grinding were stored in screw cap vials for subsequent analysis.

Example 8

Preparation of Meloxicam:Adipic Acid Cocrystal (2:1)

176 mg of meloxicam was ground with 37 mg of adipic acid and 400 µL of chloroform was added to the solid mixture. The solids gathered after grinding were stored in screw cap vials for subsequent analysis.

Example 9

Preparation of Meloxicam:Benzoic Acid Cocrystal (1:1)

176 mg of meloxicam was ground with 61 mg of benzoic acid and 400 µL of THF was added to the solid mixture. The solids gathered after grinding were stored in screw cap vials for subsequent analysis.

Example 10

Preparation of Meloxicam:Benzoic Acid Cocrystal (1:1)

176 mg of meloxicam was ground with 61 mg of benzoic acid and 400 µL of chloroform was added to the solid mixture. The solids gathered after grinding were stored in screw cap vials for subsequent analysis.

Example 11

Preparation of Meloxicam:DL-Malic Acid Cocrystal (2:1)

176 mg of meloxicam was ground with 33 mg of DL-malic acid and 400 µL of THF was added to the solid mixture. The solids gathered after grinding were stored in screw cap vials for subsequent analysis.

Example 12

Preparation of Meloxicam:DL-Malic Acid Cocrystal (2:1)

176 mg of meloxicam was ground with 33 mg of DL-malic acid and 400 µL of chloroform was added to the solid mixture. The solids gathered after grinding were stored in screw cap vials for subsequent analysis.

Example 13

Preparation of Meloxicam: L-Malic Acid Cocrystal (2:1)

176 mg of meloxicam was ground with 33 mg of L-malic acid and 400 µL of THF was added to the solid mixture. The solids gathered after grinding were stored in screw cap vials for subsequent analysis.

Example 14

Preparation of Meloxicam: L-Malic Acid Cocrystal (2:1)

176 mg of meloxicam was ground with 33 mg of L-malic acid and 400 µL of chloroform was added to the solid mixture. The solids gathered after grinding were stored in screw cap vials for subsequent analysis.

Example 15

Preparation of Meloxicam: Glutaric Acid Cocrystal (1:1)

176 mg of meloxicam was ground with 66 mg of glutaric acid and 400 µL of THF was added to the solid mixture. The solids gathered after grinding were stored in screw cap vials for subsequent analysis.

Example 16

Preparation of Meloxicam: Glutaric Acid Cocrystal (1:1)

176 mg of meloxicam was ground with 66 mg of glutaric acid and 400 µL of chloroform was added to the solid mixture. The solids gathered after grinding were stored in screw cap vials for subsequent analysis.

Example 17

Preparation of Meloxicam: Aspirin Cocrystal (1:1)

176 mg of meloxicam was ground with 90 mg of aspirin and 400 µL of THF was added to the solid mixture. The solids gathered after grinding were stored in screw cap vials for subsequent analysis.

Example 18

Preparation of Meloxicam: Aspirin Cocrystal (1:1)

176 mg of meloxicam was ground with 90 mg of aspirin and 400 µL of chloroform was added to the solid mixture. The solids gathered after grinding were stored in screw cap vials for subsequent analysis.

Example 19

Preparation of Meloxicam: Salicylic Acid Cocrystal Form I (1:1)

176 mg of meloxicam was ground with 69 mg of salicyclic acid and 400 µL of THF was added to the solid mixture. The solids gathered after grinding were stored in screw cap vials for subsequent analysis.

Example 20

Preparation of Meloxicam: Salicyclic Acid Cocrystal Form II (1:1)

176 mg of meloxicam was ground with 90 mg of salicyclic acid and 400 µL of chloroform was added to the solid mixture. The solids gathered after grinding were stored in screw cap vials for subsequent analysis.

Example 21

Preparation of Meloxicam: 1-hydroxy-2-naphthoic Acid Cocrystal (1:1)

176 mg of meloxicam was ground with 94 mg of 1-hydroxy-2-naphthoic acid and 400 µL of THF was added to the solid mixture. The solids gathered after grinding were stored in screw cap vials for subsequent analysis.

Example 22

Preparation of Meloxicam: 1-hydroxy-2-naphthoic Acid Cocrystal (1:1)

176 mg of meloxicam was ground with 94 mg of 1-hydroxy-2-naphthoic acid and 400 µL of chloroform was added to the solid mixture. The solids gathered after grinding were stored in screw cap vials for subsequent analysis.

Example 23

Preparation of Meloxicam: 1-hydroxy-2-naphthoic Acid Cocrystal (1:1)

88 mg of meloxicam was dissolved in 8 ml of THF:isoproponal (3:1 v/v) mixture, 47 mg of 1-hydroxy-2-naphthoic acid was added to the solution to form a single solution. The solution was then allowed to stand for several hours to effect the slow evaporation of solvent. The solids gathered were stored in screw cap vials for subsequent analysis.

Example 24

Preparation of Meloxicam: 1-hydroxy-2-naphthoic Acid Cocrystal (1:1)

88 mg of meloxicam was dissolved in 5 ml of dioxane:methanol (3:1 v/v) mixture, 47 mg of 1-hydroxy-2-naphthoic acid was added to the solution to form a single solution. The solution was then allowed to stand for several hours to effect the slow evaporation of solvent. The solids gathered were stored in screw cap vials for subsequent analysis.

Example 25

Preparation of Meloxicam: Maleic Acid Cocrystal (1:1)

176 mg of meloxicam was ground with 58 mg of maleic acid and 400 µL of THF was added to the solid mixture. The solids gathered after grinding were stored in screw cap vials for subsequent analysis.

Example 26

Preparation of Meloxicam: Maleic Acid Cocrystal (1:1)

176 mg of meloxicam was ground with 58 mg of maleic acid and 400 µL of chloroform was added to the solid mixture. The solids gathered after grinding were stored in screw cap vials for subsequent analysis.

Example 27

Preparation of Meloxicam: 4-hydroxybenzoic Acid Cocrystal (1:1)

176 mg of meloxicam was ground with 69 mg of 4-hydroxybenzoic acid and 400 µL of THF was added to the solid mixture. The solids gathered after grinding were stored in screw cap vials for subsequent analysis.

Example 28

Preparation of Meloxicam: Malonic Acid Cocrystal (1:1)

176 mg of meloxicam was ground with 52 mg of malonic acid and 400 µL of THF was added to the solid mixture. The solids gathered after grinding were stored in screw cap vials for subsequent analysis.

Example 29

Preparation of Meloxicam: Malonic Acid Cocrystal (1:1)

176 mg of meloxicam was ground with 52 mg of malonic acid and 400 µL of chloroform was added to the solid mixture. The solids gathered after grinding were stored in screw cap vials for subsequent analysis.

Example 30

Preparation of Meloxicam: Glycolic Acid Cocrystal (1:1)

176 mg of meloxicam was ground with 38 mg of glycolic acid and 400 µL of THF was added to the solid mixture. The solids gathered after grinding were stored in screw cap vials for subsequent analysis.

Example 31

Preparation of Meloxicam: Glycolic Acid Cocrystal (1:1)

176 mg of meloxicam was ground with 38 mg of glycolic acid and 400 µL of chloroform was added to the solid mixture. The solids gathered after grinding were stored in screw cap vials for subsequent analysis.

Example 32

Preparation of Meloxicam: 2,5-dihydroxybenzoic Acid Form 1 Cocrystal (1:1)

176 mg of meloxicam was ground with 77 mg of 2,5-dihydroxybenzoic acid and 400 µL of THF was added to the solid mixture. The solids gathered after grinding were stored in screw cap vials for subsequent analysis.

Example 33

Preparation of Meloxicam: 2,5-dihydroxybenzoic Acid Form 2 Cocrystal (1:1)

176 mg of meloxicam was ground with 77 mg of 2,5-dihydroxybenzoic acid and 400 µL of chloroform was added to the solid mixture. The solids gathered after grinding were stored in screw cap vials for subsequent analysis.

Example 34

Preparation of Meloxicam: (+) Camphoric Acid Form 1 Cocrystal (3:2)

176 mg of meloxicam was ground with 100 mg of (+) camphoric acid and 400 µL of THF was added to the solid mixture. The solids gathered after grinding were stored in screw cap vials for subsequent analysis.

Example 35

Preparation of Meloxicam: (+) Camphoric Acid Form 2 Cocrystal (3:2)

176 mg of meloxicam was ground with 100 mg of (+) camphoric acid and 400 µL of chloroform was added to the solid mixture. The solids gathered after grinding were stored in screw cap vials for subsequent analysis.

Example 36

Preparation of Meloxicam:Maltol Cocrystal (1:1)

175 mg of meloxicam was ground with 62.8 mg of maltol and 400 µL of ethyl acetate was added to the solid mixture. The solids gathered after grinding were stored in screw cap vials for subsequent analysis.

Example 37

Preparation of Meloxicam:Salicylic Acid Cocrystal Form III (1:1)

876 mg of meloxicam and 350 mg of salicylic acid was slurried in 2 ml of THF overnight. The solids gathered after filtration were dried and stored in a screw cap vials for subsequent analysis.

Example 38

Preparation of Meloxicam:Salicylic Acid Cocrystal Form III (1:1)

875 mg of meloxicam and 351 mg of salicylic acid was slurried in 4 ml of ethyl acetate overnight. The solids gathered after filtration were dried and stored in a screw cap vials for subsequent analysis.

Example 39

Preparation of Meloxicam:Salicylic Acid Cocrystal Form III (1:1)

877 mg of meloxicam and 356 mg of salicylic acid was slurried in 2 ml of acetone overnight. The solids gathered after filtration were dried and stored in a screw cap vials for subsequent analysis.

Example 40

Preparation of Meloxicam:Ethyl Maltol Cocrystal (1:1)

181 mg of meloxicam was ground with 81 mg of ethyl maltol and 200 µL of chloroform was added to the solid mixture. The solids gathered after grinding were stored in screw cap vials for subsequent analysis.

Example 41

Preparation of Meloxicam:Hydrocinnamic Acid Cocrystal (1:1)

176 mg of meloxicam was ground with 75 mg of hydrocinnamic acid and 400 µL of THF was added to the solid mixture. The solids gathered after grinding were stored in screw cap vials for subsequent analysis.

Example 42

Preparation of Meloxicam:Maleic Acid Cocrystal 52.6 g of meloxicam and 17.4 g of maleic acid were mixed in a beaker and 150 ml of pure ethyl acetate was then added to the mixture. The beaker was sealed and stirred for 12 hours with a magnetic stirrer set at 200 rpm. The resultant slurry was then filtered and solids washed with pure ethyl acetate. The solid crystalline material was then dried in an oven set at 40° C. for 24 hours. The particulate material was gathered and stored in screw cap containers for subsequent analysis.

Example 43

Preparation of Meloxicam:Aspirin Cocrystal 46.3 g of meloxicam was mixed with 23.7 g of aspirin in a beaker and 150 ml of pure ethyl acetate was then added to the mixture. The beaker was sealed and stirred for 12 hours with a magnetic stirrer set at 200 rpm. The resultant slurry was then filtered and solids washed with pure ethyl acetate. The solid crystalline material was then dried in an oven set at 40° C. for 24 hours. The particulate material was gathered and stored in screw cap containers for subsequent analysis.

Example 44

Preparation of Meloxicam:Salicylic Acid Form III Cocrystal 21.5 g of meloxicam and 9.3 g of salicylic acid was slurried in 90 ml of ethyl acetate for 12 hours in a sealed beaker magnetically stirred at 200 rpm for 12 hours. The slurry was then filtered and solids washed with pure ethyl acetate. The solid crystalline material was then dried in an oven set at 40°

C. for 24 hours. The particulate material was gathered and stored in screw cap containers for subsequent analysis.

Example 45

Preparation of Meloxicam:1-hydroxy-2-naphthoic Acid Cocrystal 45.6 g of meloxicam and 24.4 g of 1-hydroxy-2-naphthoic acid was slurried for 12 hours in 300 ml of ethyl acetate in a sealed beaker. The slurry was stirred for 12 hours with magnetic stirrer at 200 rpm. The resultant slurry was then filtered and solids washed with pure ethyl acetate. The solid crystalline material was then dried in an oven set at 40° C. for 24 hours. The particulate material was gathered and stored in screw cap containers for subsequent analysis.

Example 46

Preparation of Meloxicam:Succinic Acid Cocrystal 59.9 g of meloxicam and 10.1 g of succinic acid were mixed in a beaker and 150 ml of pure ethyl acetate was then added to the mixture. The beaker was sealed and stirred for 12 hours with a magnetic stirrer set at 200 rpm. The resultant slurry was then filtered and solids washed with pure ethyl acetate. The solid crystalline material was then dried in an oven set at 40° C. for 24 hours. The particulate material was gathered and stored in screw cap containers for subsequent analysis.

We claim:

1. A crystalline form of meloxicam, which has improved bioavailability, an enhanced rate of dissolution and shorter time to $C_{max}$ in blood when compared to the bioavailability, rate of dissolution, and time to $C_{max}$, of marketed pure meloxicam, selected from the group consisting of co-crystal meloxicam:fumaric acid, co-crystal meloxicam:succinic acid, co-crystal meloxicam:adipic acid; co-crystal meloxicam:benzoic acid, co-crystal meloxicam:DL-malic acid, co-crystal meloxicam:L-malic acid, co-crystal meloxicam:glutaric acid, co-crystal meloxicam:acetylsalicylic acid, co-crystal meloxicam:salicylic acid form I, co-crystal meloxicam:salicylic acid form II, co-crystal meloxicam:salicylic acid form III, co-crystal meloxicam:1-hydroxy-2-naphthoic acid, co-crystal meloxicam:maleic acid, co-crystal meloxicam:4-hydroxybenzoic acid, co-crystal meloxicam: malonic acid, co-crystal meloxicam:glycolic acid, co-crystal meloxicam:2,5-dihydroxybenzoic acid form I, co-crystal meloxicam:2,5-dihydroxybenzoic acid form II, co-crystal meloxicam:camphoric acid form I, co-crystal meloxicam: camphoric acid form II, co-crystal meloxicam:maltol, co-crystal meloxicam :ethyl maltol, and co-crystal meloxicam: hydrocinnamic acid.

2. The crystalline form of meloxicam of claim 1, wherein said crystalline form is co-crystal meloxicam:fumaric acid which: a) has a PXRD diffraction pattern with peaks at about 12.13, 14.75, 16.52, 18.14, 22.21, 23.53 and 26.86+/−0.2 degrees two-theta; and/or b) has a PXRD diffraction pattern as depicted in FIG. 1.

3. The crystalline form of meloxicam of claim 1, wherein said crystalline form is co-crystal meloxicam:succinic acid which: a) has a PXRD diffraction pattern with peaks at about 13.22, 14.50, 16.41, 18.30, 23.68, 26.59 and 27.67+/−0.2 degrees two-theta; and/or b) has a PXRD diffraction pattern as depicted in FIG. 3.

4. The crystalline form of meloxicam of claim 1, wherein said crystalline form is co-crystal meloxicam:adipic acid which: a) has a PXRD diffraction pattern with peaks at about 8.56, 9.38, 12.67, 17.50, 24.13, 26.77, and 27.46 +/−0.2 degrees two-theta; and/or b) has a PXRD diffraction pattern as depicted in FIG. 5.

5. The crystalline form of meloxicam of claim 1, wherein said crystalline form is co-crystal meloxicam:benzoic acid which: a) has a PXRD diffraction pattern with peaks at about 9.61, 14.06, 15.00, 16.01, 17.21, 18.20 and 26.47+/−0.2 degrees two-theta; and/or b) has a PXRD diffraction pattern as depicted in FIG. 7.

6. The crystalline form of meloxicam of claim 1, wherein said crystalline form is co-crystal meloxicam:DL-malic acid which: a) has a PXRD diffraction pattern with peaks at about 13.39, 14.87, 16.55, 18.39, 23.78, 26.80 and 27.91+/−0.2 degrees two-theta; and/or b) has a PXRD diffraction pattern as depicted in FIG. 9.

7. The crystalline form of meloxicam of claim 1, wherein said crystalline form is co-crystal meloxicam:L-malic acid which: a) has a PXRD diffraction pattern with peaks at about 13.14, 14.57, 16.25, 23.51, 24.66, 26.53 and 27.66+/−0.2 degrees two-theta; and/or b) has a PXRD diffraction pattern as depicted in FIG. 11.

8. The crystalline form of meloxicam of claim 1, wherein said crystalline form is co-crystal meloxicam:glutaric acid which: a) has a PXRD diffraction pattern with peaks at about 5.16, 13.85, 15.26, 16.13, 19.64, 26.17 and 27.58+/−0.2 degrees two-theta; and/or b) has a PXRD diffraction pattern as depicted in FIG. 13.

9. The crystalline form of meloxicam of claim 1, wherein said crystalline form is co-crystal meloxicam:acetylsalicylic acid which: a) has a PXRD diffraction pattern with peaks at about 9.57, 13.55, 14.18, 19.49, 22.51, 23.86 and 24.88 +/−0.2 degrees two-theta; and/or b) has a PXRD diffraction pattern as depicted in FIG. 15.

10. The crystalline form of meloxicam of claim 1, wherein said crystalline form is co-crystal meloxicam:salicylic acid form I which: a) has a PXRD diffraction pattern with peaks at about 12.08, 13.85, 14.75, 16.10, 25.24, 25.87 and 27.00 +/−0.2 degrees two-theta; and/or b) has a PXRD diffraction pattern as depicted in FIG. 17.

11. The crystalline form of meloxicam of claim 1, wherein said crystalline form is co-crystal meloxicam:salicylic acid form II which: a) has a PXRD diffraction pattern with peaks at about 6.27, 15.02, 15.47, 19.70, 25.66, 26.23 and 27.49 +/−0.2 degrees two-theta; and/or b) has a PXRD diffraction pattern as depicted in FIG. 19.

12. The crystalline form of meloxicam of claim 1, wherein said crystalline form is co-crystal meloxicam:salicylic acid form III which: a) has a PXRD diffraction pattern with peaks at about 9.57, 13.55, 14.18, 19.49, 22.51, 23.86 and 24.88 +/−0.2 degrees two-theta; and/or b) has a PXRD diffraction pattern as depicted in FIG. 41.

13. The crystalline form of meloxicam of claim 1, wherein said crystalline form is co-crystal meloxicam:1-hydroxy-2-naphthoic acid which: a) has a PXRD diffraction pattern with peaks at about 6.67, 12.35, 14.92, 16.25, 17.75, 25.93 and 26.88+/−0.2 degrees two-theta; and/or b) has a PXRD diffraction pattern as depicted in FIG. 21.

14. The crystalline form of meloxicam of claim 1, wherein said crystalline form is co-crystal meloxicam:maleic acid which: a) has a PXRD diffraction pattern with peaks at about 8.27, 15.50, 16.35, 18.59, 21.43, 22.58 and 25.69+/−0.2 degrees two-theta; and/or b) has a PXRD diffraction pattern as depicted in FIG. 23.

15. The crystalline form of meloxicam of claim 1, wherein said crystalline form is co-crystal meloxicam:4-hydroxybenzoic acid which: a) has a PXRD diffraction pattern with peaks at about 6.88, 7.92, 13.34, 17.87, 19.41, 25.36 and 26.86 +/−0.2 degrees two-theta; and/or b) has a PXRD diffraction pattern as depicted in FIG. 25.

16. The crystalline form of meloxicam of claim 1, wherein said crystalline form is co-crystal meloxicam:malonic acid which: a) has a PXRD diffraction pattern with peaks at about 9.74, 11.88, 14.06, 15.02, 19.34, 22.27 and 26.83+/−0.2 degrees two-theta; and/or b) has a PXRD diffraction pattern as depicted in FIG. 27.

17. The crystalline form of meloxicam of claim 1, wherein said crystalline form is co-crystal meloxicam:glycolic acid which: a) has a PXRD diffraction pattern with peaks at about 10.91, 14.18, 14.87, 15.56, 19.28, 21.37 and 26.38+/−0.2 degrees two-theta; and/or b) has a PXRD diffraction pattern as depicted in FIG. 29.

18. The crystalline form of meloxicam of claim 1, wherein said crystalline form is co-crystal meloxicam:2,5-dihydroxybenzoic acid form I which: a) has a PXRD diffraction pattern with peaks at about 9.77, 14.96, 18.84, 22.85, 24.43, 25.12 and 29.02+/−0.2 degrees two-theta; and/or b) has a PXRD diffraction pattern as depicted in FIG. 31.

19. The crystalline form of meloxicam of claim 1, wherein said crystalline form is co-crystal meloxicam:2,5-dihydroxybenzoic acid form II which: a) has a PXRD diffraction pattern with peaks at about 9.86, 15.05, 19.07, 19.79, 22.99, 25.27 and 26.32+/−0.2 degrees two-theta; and/or b) has a PXRD diffraction pattern as depicted in FIG. 33.

20. The crystalline form of meloxicam of claim 1, wherein said crystalline form is co-crystal meloxicam:camphoric acid form I which: a) has a PXRD diffraction pattern with peaks at about 7.68, 11.35, 13.64, 15.47, 26.23 and 26.83+/−0.2 degrees two-theta; and/or b) has a PXRD diffraction pattern as depicted in FIG. 35.

21. The crystalline form of meloxicam of claim 1, wherein said crystalline form is co-crystal meloxicam:camphoric acid form II which: a) has a PXRD diffraction pattern with peaks at about 5.19, 9.95, 11.41, 13.50, 15.38, 16.70, 26.23 and 36.21+/−0.2 degrees two-theta; and/or b) has a PXRD diffraction pattern as depicted in FIG. 37.

22. The crystalline form of meloxicam of claim 1, wherein said crystalline form is co-crystal meloxicam:maltol which: a) has a PXRD diffraction pattern with peaks at about 9.41, 12.83, 14.87, 16.37, 23.39, 25.78 and 28.88+/−0.2 degrees two-theta; and/or b) has a PXRD diffraction pattern as depicted in FIG. 39.

23. The crystalline form of meloxicam of claim 1, wherein said crystalline form is co-crystal meloxicam:ethyl maltol which: a) has a PXRD diffraction pattern with peaks at about 6.67, 12.35, 14.92, 16.25, 17.75, 25.93 and 26.88+/−0.2 degrees two-theta; and/or b) has a PXRD diffraction pattern as depicted in FIG. 43.

24. The crystalline form of meloxicam of claim 1, wherein said crystalline form is co-crystal meloxicam:hydrocinnamic acid which: a) has a PXRD diffraction pattern with peaks at about 8.27, 15.50, 16.35, 18.59, 21.43, 22.58 and 25.69 +/−0.2 degrees two-theta; and/or b) has a PXRD diffraction pattern as depicted in FIG. 45.

25. A solid pharmaceutical composition comprising an effective amount of one or more of the crystalline forms of meloxicam of claim 1 and a pharmaceutically acceptable excipient.

\* \* \* \* \*

UNITED STATES PATENT AND TRADEMARK OFFICE
CERTIFICATE OF CORRECTION

Page 1 of 1

PATENT NO. : 8,124,603 B2
APPLICATION NO. : 12/321525
DATED : February 28, 2012
INVENTOR(S) : Hanna et al.

It is certified that error appears in the above-identified patent and that said Letters Patent is hereby corrected as shown below:

In the Claims

Column 24, line 50 (Claim 12, line 4) delete "9.57, 13.55, 14.18, 19.49, 22.51, 23.86 and 24.88" and replace with --9.413, 12.830, 14.869, 16.368, 23.386, 25.781, and 28.875--.
Column 25, line 30 (Claim 20, line 4) insert --4.107,-- before "7.68".
Column 26, lines 9-10 (Claim 22, lines 3-4) delete "9.41, 12.83, 14.87, 16.37, 23.39, 25.78 and 28.88" and replace with --3.950, 7.398, 10.940, 14.451, 16.069, 26.201, and 26.950--.
Column 26, line 16 (Claim 23, line 4) delete "6.67, 12.35, 14.92, 16.25, 17.75, 25.93 and 26.88" and replace with --3.758, 7.165, 10.541, 13.940, 15.262, 19.678, and 25.211--.
Column 26, line 22 (Claim 24, line 4) delete "8.27, 15.50, 16.35, 18.59, 21.43, 22.58 and 25.69" and replace with --4.243, 8.321, 13.692, 15.798, 19.965, 23.223, and 26.471--.

Signed and Sealed this
Twenty-fourth Day of September, 2013

Teresa Stanek Rea
*Deputy Director of the United States Patent and Trademark Office*